(12) United States Patent
Kungl

(10) Patent No.: US 7,585,937 B2
(45) Date of Patent: Sep. 8, 2009

(54) GAG BINDING PROTEINS

(75) Inventor: Andreas J. Kungl, Graz (AT)

(73) Assignee: Protaffin Biotechnologie AG, Graz (AT)

( * ) Notice: Subject to any disclaimer, the term of this patent is extended or adjusted under 35 U.S.C. 154(b) by 260 days.

(21) Appl. No.: 11/422,169

(22) Filed: Jun. 5, 2006

(65) Prior Publication Data

US 2008/0112926 A1 May 15, 2008

Related U.S. Application Data

(63) Continuation of application No. PCT/EP2004/013670, filed on Dec. 2, 2004.

(30) Foreign Application Priority Data

Dec. 4, 2003 (AT) .............................. A 1952/2003

(51) Int. Cl.
*C07K 14/54* (2006.01)

(52) U.S. Cl. ...................... 530/324; 530/300

(58) Field of Classification Search ........................ None
See application file for complete search history.

(56) References Cited

FOREIGN PATENT DOCUMENTS

| WO | WO 92/07935 | * | 5/1992 |
| WO | WO 96/34965 | * | 11/1996 |
| WO | WO 02/20715 | | 3/2002 |

OTHER PUBLICATIONS

Butcher et al, (1997) FEBS Letters, vol. 409, No. 2, pp. 183-187.*
Mikayama et al. Proc. Natl. Acad. Sci. USA vol. 90, pp. 10056-10060.*
Voet et al. Biochemistry John Wiley & Sons, Inc., pp. 126-128 and 228-234.*
Butcher et al (1997), FEBS Letters, vol. 409, No. 2, pp. 183-187.*
Brander, Klonierung, Expression und Reinigung bindungsmodifizierter Interleukin-8 Mutanten, Zur Erlangung des akademischen Grades einer, Magistra Pharmaciae, an der Naturwissenschaftlichen Fakultät der, Karl-Franzens-Universität Graz (2002) (with English Abstract).
Butcher et al., FEBS Letters 409: 183-187 (1997).
Ecker, Österreichische Apotheker-Zeitung 57(14): 658-660 (2003).
Jayaraman et al. FEBS Letters 482: 154-158 (2000).
Jinno-Oue et al., Journal of Virology 75(24): 12439-12445 (2001).
Hileman et al., BioEssays 20: 156-167 (1998).
Lortat-Jacob et al., PNAS 99(3): 1229-1234 (2002).
Yang et al., Journal of Cellular Biochemistry 56: 455-468 (1994).
Verrecchio et al., The Journal of Biological Chemistry 275(11): 7701-7707 (2000).
Wong et al., The Journal of Biological Chemistry 273(29): 18617-18622 (1998).
Barbara Brandner; Translation of "'Klonierung, Expression und Reinigung bindungsmodifizierter Interleukin-8 Mutanten' [Cloning, expression and purification of binding-modified interleukin-8 mutations]"; Jan. 24, 2009; 90 pages; Master of Pharmacy at the Natural Sciences Faculty of Karl-Franzens University; Graz, Austria.

* cited by examiner

*Primary Examiner*—Prema Mertz
(74) *Attorney, Agent, or Firm*—Proskauer Rose LLP

(57) ABSTRACT

A method is provided for introducing a GAG binding site into a protein comprising the steps:
   identifying a region in a protein which is not essential for structure maintenance
   introducing at least one basic amino acid into said site and/or deleting at least one bulky and/or acidic amino acid in said site,
whereby said GAG binding site has a GAG binding affinity of $Kd \leq 10\,\mu M$, preferably $1\,\mu M$, still preferred $\leq 0.1\,\mu M$, as well as modified GAG binding proteins.

**16 Claims, 4

| sec. structure | IL-8Δ6 E70R | IL-8Δ6 E70R HS | IL-8Δ6 F17RF21R E70K | IL-8Δ6 F17RF21R E70K HS |
|---|---|---|---|---|
| α-helix [%] | 24,9 | 37 | 17,4 | 28,7 |
| β-sheet [%] | 23,6 | 23 | 29,8 | 22 |
| turns [%] | 20,9 | 27,3 | 25,9 | 29,7 |
| others [%] | 40,7 | 12,7 | 26,9 | 19,6 | ary
GAG BINDING PROTEINS

This application is a continuation of PCT/EP2004/013670 filed on Dec. 2, 2004. The entire contents of the above-identified application are hereby incorporated by reference.

The present invention relates to methods and tools for the inhibition of the interaction of chemokines and their high-affinity receptors on leukocytes and methods for the therapeutic treatment of inflammatory diseases.

Chemokines, originally derived from chemoattractant cytokines, actually comprise more than 50 members and represent a family of small, inducible, and secreted proteins of low molecular weight (6-12 kDa in their monomeric form) that play a decisive role during immunosurveillance and inflammatory processes. Depending on their function in immunity and inflammation, they can be distinguished into two classes. Inflammatory chemokines are produced by many different tissue cells as well as by immigrating leukocytes in response to bacterial toxins and inflammatory cytokines like IL-1, TNF and interferons. Their main function is to recruit leukocytes for host defense and in the process of inflammation. Homing chemokines, on the other hand, are expressed constitutively in defined areas of the lymphoid tissues. They direct the traffic and homing of lymphocytes and dendritic cells within the immune system. These chemokines, as illustrated by BCA-1, SDF-1 or SLC, control the relocation and recirculation of lymphocytes in the context of maturation, differentiation, activation and ensure their correct homing within secondary lymphoid organs.

Despite the large number of representatives, chemokines show remarkably similar structural folds although the sequence homology varies between 20 to 70 percent. Chemokines consist of roughly 70-130 amino acids with four conserved cysteine residues. The cysteines form two disulphide bonds (Cys 1→Cys 3, Cys 2→Cys 4) which are responsible for their characteristic three-dimensional structure. Chemotactic cytokines consist of a short amino terminal domain (3-10 amino acids) preceding the first cysteine residue, a core made of β-strands and connecting loops found between the second and the fourth cysteine residue, as well as a carboxy-terminal α-helix of 20-60 amino acids. The protein core has a well ordered structure whereas the N- and C-terminal parts are disordered. As secretory proteins they are synthesised with a leader sequence of 20-25 amino acids which is cleaved off before release.

The chemokines have been subdivided into four families on the basis of the relative position of their cysteine residues in the mature protein. In the α-chemokine subfamily, the first two of the four cysteines are separated by a single amino acid (CXC), whereas in the β-chemokines the corresponding cysteine residues are adjacent to each other (CC). The α-chemokines can be further classified into those that contain the ELR sequence in the N-terminus, thereby being chemotactic for neutrophils (IL-8 for example), and those that lack the ELR motif and act on lymphocytes (I-TAC for example). Structurally the β-chemokines can be subdivided into two families: the monocyte-chemoattractant protein eotaxin family, containing the five monocyte chemoattractant proteins (MCP) and eotaxin which are approximately 65 percent identical to each other, and the remaining β-chemokines. As with the CXC-family, the N-terminal amino acids preceding the CC-residues are critical components for the biologic activity and leukocyte selectivity of the chemokines. The β-chemokines, in general, do not act on neutrophils but attract monocytes, eosinophils, basophils and lymphocytes with variable selectivity.

Only a few chemokines do not fit into the CC- or the CXC-family. Lymphotactin is so far the only chemokine which shows just two instead of the four characteristic cysteines in its primary structure, and is thus classified as γ- or C-chemokine. On the other hand, by concluding this classification, fractalkine has to be mentioned as the only representative of the δ- or CXXXC-subfamily with three amino acids separating the first two cysteines. Both of them, Lymphotaxin and fractalkine, induce chemotaxis of T-cells and natural killer cells.

Chemokines induce cell migration and activation by binding to specific cell surface, seven transmembrane-spanning (7TM) G-protein-coupled receptors on target cells. Eighteen chemokine receptors have been cloned so far including six CXC, ten CC, one CX3C and one XC receptor. Chemokine receptors are expressed on different types of leukocytes, some of them are restricted to certain cells (e.g. CXCR1 is restricted to neutrophils) whereas others are more widely expressed (e.g. CCR2 is expressed on monocytes, T cells, natural killer cells and basophils). Similar to chemokines, the receptors can be constitutively expressed on certain cells, whereas some are inducible. Some of them can even be down-regulated making the cells unresponsive to a certain chemokine but remaining responsive to another. Most receptors recognise more than one chemokine and vice versa but recognition is restricted to chemokines of the corresponding subfamily (see Table 1).

TABLE 1

| | Chemokine | Receptor | Chemotactic for | Inflammatory Diseases |
|---|---|---|---|---|
| CXC-Chemokine (+ELR-motif) | IL-8 | CXCR1 CXCR2 | Neutrophils | Acute respiratory distress syndrome [71]; Bacterial pneumonia [72]; Rheumathoid arthritis [73]; Inflammatory bowel disease [74]; Psoriasis [75]; Bacterial meningitis [76] |
| CC-Chemokine | MCP-1 | CCR2 | Basophils; Monocytes; Activated T cells; Dentritic cells; Natural killer cells | Asthma [77]; Glomerulonephritis [78]; Atheroscleosis [79]; Inflammatory bowel disease [80]; |

TABLE 1-continued

| Chemokine | Receptor | Chemotactic for | Inflammatory Diseases |
|---|---|---|---|
| RANTES | CCR1 | Eosinophils; Monocytes; Activated T cells; Dentritic cells | Psoriasis [81]; Bacterial and viral meningitis [82, 83] Asthma [84]; Glomerulonephritis [85] |
| | CCR3 | Eosinophils; Basophils; Dentritic cells | |
| | CCR5 | Monocytes; Activated T cells; Dentritic cells; Natural killer cells | |

Chemokines have two main sites of interaction with their receptors, one in the amino-terminal domain and the other within an exposed loop of the backbone that extends between the second and the third cysteine residue. Both sites are kept in close proximity by the disulphide bonds. The receptor recognises first the binding site within the loop region which appears to function as a docking domain. This interaction restricts the mobility of the chemokine thus facilitating the proper orientation of the amino-terminal domain. Studies have been performed with mutant chemokines that still bound effectively to their receptors but did not signal. These mutants were obtained by amino acid deletion or modification within the N-termini of, for example, IL-8, RANTES and MCP-1.

Multiple intracellular signalling pathways occur after receptor activation as a result of chemokine binding. Chemokines also interact with two types of nonsignalling molecules. One is the DARC receptor which is expressed on erythrocytes and on endothelial cells and which binds CC- as well as CXC-chemokines to prevent them from circulation. The second type are heparan sulphate glycosaminoglycans (GAGs) which are part of proteoglycans and which serve as co-receptors of chemokines. They capture and present chemokines on the surface of the homing tissue (e.g. endothelial cells) in order to establish a local concentration gradient. In an inflammatory response, such as in rheumatoid arthritis, leukocytes rolling on the endothelium in a selectin-mediated process are brought into contact with the chemokines presented by the proteoglycans on the cell surface. Thereby, leukocyte integrins become activated which leads to firm adherence and extravasation. The recruited leukocytes are activated by local inflammatory cytokines and may become desensitised to further chemokine signalling because of high local concentration of chemokines. For maintaining a tissue bloodstream chemokine gradient, the DARC receptor functions as a sink for surplus chemokines.

Heparan sulphate (HS) proteoglycans, which consist of a core protein with covalently attached glycosaminoglycan sidechains (GAGs), are found in most mammalian cells and tissues. While the protein part determines the localisation of the proteoglycan in the cell membrane or in the extracellular matrix, the glycosaminoglycan component mediates interactions with a variety of extracellular ligands, such as growth factors, chemokines and adhesions molecules. The biosynthesis of proteoglycans has previously been extensively reviewed. Major groups of the cell surface proteoglycans are the syndecan family of transmembrane proteins (four members in mammals) and the glypican family of proteins attached to the cell membrane by a glycosylphosphatidylinositol (GPI) tail (six members in mammals). While glypicans are expressed widely in the nervous system, in kidney and, to a lesser extent, in skeletal and smooth muscle, syndecan-1 is the major HSPG in epithelial cells, syndecan-2 predominates in fibroblasts and endothelial cells, syndecan-3 abounds in neuronal cells and syndecan-4 is widely expressed. The majority of the GAG chains added to the syndecan core proteins through a tetrasaccharide linkage region onto particular serines are HS chains. Although the amino acid sequences of the extracellular domains of specific syndecan types are not conserved among different species, contrary to the transmembrane and the cytoplasmic domains, the number and the positions of the GAG chains are highly conserved. The structure of the GAGs, however, is species-specific and is, moreover, dependent upon the nature of the HSPG-expressing tissue.

Heparan sulphate (HS) is the most abundant member of the glycosaminoglycan (GAG) family of linear polysaccharides which also includes heparin, chondroitin sulphate, dermatan sulphate and keratan sulphate. Naturally occurring HS is characterised by a linear chain of 20-100 disaccharide units composed of N-acetyl-D-glucosamine (GlcNAc) and D-glucuronic acid (GlcA) which can be modified to include N- and O-sulphation (6-O and 3-O sulphation of the glucosamine and 2-O sulphation of the uronic acid) as well as epimerisation of $\beta$-D-gluronic acid to $\alpha$-L-iduronic acid (IdoA).

Clusters of N- and O-sulphated sugar residues, separated by regions of low sulphation, are assumed to be mainly responsible for the numerous protein binding and regulatory properties of HS. In addition to the electrostatic interactions of the HS sulphate groups with basic amino acids, van der Waals and hydrophobic interactions are also thought to be involved in protein binding. Furthermore, the presence of the conformationally flexible iduronate residues seems to favour GAG binding to proteins. Other factors such as the spacing between the protein binding sites play also a critical role in protein-GAG binding interactions: For example $\gamma$-interferon dimerisation induced by HS requires GAG chains with two protein binding sequences separated by a 7 kDa region with low sulphation. Additional sequences are sometimes required for full biological activity of some ligands: in order to support FGF-2 signal transduction, HS must have both the minimum binding sequence as well as additional residues that are supposed to interact with the FGF receptor.

Heparin binding proteins often contain consensus sequences consisting of clusters of basic amino acid residues. Lysine, arginine, asparagine, histidine and glutamine are frequently involved in electrostatic contacts with the sulphate and carboxyl groups on the GAG. The spacing of the basic amino acids, sometimes determined by the proteins 3-D structure, are assumed to control the GAG binding specificity and affinity. The biological activity of the ligand can also be affected by the kinetics of HS-protein interaction. Reducing the dimension of growth factor diffusion is one of the suggested HSPG functions for which the long repetitive character of the GAG chains as well as their relatively fast on and off rates of protein binding are ideally suited. In some cases, kinetics rather than thermodynamics drives the physiological function of HS-protein binding. Most HS ligands require GAG sequences of well-defined length and structure. Heparin, which is produced by mast cells, is structurally very similar to heparan sulphate but is characterised by higher levels of post-polymerisation modifications resulting in a uniformly high degree of sulphation with a relatively small degree of structural diversity. Thus, the highly modified blocks in heparan sulphate are sometimes referred to as "heparin-like". For this reason, heparin can be used as a perfect HS analogue for protein biophysical studies as it is, in addition, available in larger quantities and therefore less expensive than HS. Different cell types have been shown to synthesise proteoglycans with different glycosaminoglycan structure which changes during pathogenesis, during development or in response to extracellular signals such as growth factors. This structural diversity of HSPGs leads to a high binding versatility emphasizing the great importance of proteoglycans.

Since the demonstration that heparan sulphate proteoglycans are critical for FGF signalling, several investigations were performed showing the importance of chemokine-GAG binding for promoting chemokine activity. First, almost all chemokines studied to date appear to bind HS in vitro, suggesting that this represents a fundamental property of these proteins. Second, the finding that in vivo T lymphocytes secrete CC-chemokines as a complex with glycosaminoglycans indicates that this form of interaction is physiologically relevant. Furthermore, it is known that the association of chemokines with HS helps to stabilise concentration gradients across the endothelial surface thereby providing directional information for migrating leukocytes. HS is also thought to protect chemokines from proteolytic degradation and to induce their oligomerisation thus promoting local high concentrations in the vicinity of the G-coupled signalling receptors. The functional relevance of oligomerisation, however, remains controversial although all chemokines have a clear structural basis for multimerisation. Dimerisation through association of the β-sheets is observed for all chemokines of the CXC-family (e.g. IL-8), contrary to most members of the CC-chemokine family (e.g. RANTES), which dimerise via their N-terminal strands.

A wealth of data has been accumulated on the inhibition of the interaction of chemokines and their high-affinity receptors on leukocytes by low molecular weight compounds. However, there has been no breakthrough in the therapeutic treatment of inflammatory diseases by this approach.

Interleukin-8 (IL-8) is a key molecule involved in neutrophil attraction during chronic and acute inflammation. Several approaches have been undertaken to block the action of IL-8 so far, beginning with inhibition of IL-8 production by for example glucocorticoids, Vitamin D3, cyclosporin A, transforming growth factor β, interferons etc., all of them inhibiting IL-8 activity at the level of production of IL-8 mRNA. A further approach previously used is to inhibit the binding of IL-8 to its receptors by using specific antibodies either against the receptor on the leukocyte or against IL-8 itself in order to act as specific antagonists and therefore inhibiting the IL-8 activity.

The aim of the present invention is therefore to provide an alternative strategy for the inhibition or disturbance of the interaction of chemokines/receptors on leukocytes. Specifically the action of IL-8, RANTES or MCP-1 should be targeted by such a strategy.

Subject matter of the present invention is therefore a method to produce new GAG binding proteins as well as alternative GAG binding proteins which show a high(er) affinity to a GAG co-receptor (than the wild type). Such modified GAG binding proteins can act as competitors with wild-type GAG binding proteins and are able to inhibit or down-regulate the activity of the wild-type GAG binding protein, however without the side effects which occur with the known recombinant proteins used in the state of the art. The molecules according to the present invention do not show the above mentioned disadvantages. The present modified GAG binding proteins can be used in drugs for various therapeutical uses, in particular—in the case of chemokines—for the treatment of inflammation diseases without the known disadvantages which occur in recombinant chemokines known in the state of the art. The modification of the GAG binding site according to the present invention turned out to be a broadly applicable strategy for all proteins which activity is based on the binding event to this site, especially chemokines with a GAG site. The preferred molecules according to the present invention with a higher GAG binding affinity proved to be specifically advantageous with respect to their biological effects, especially with respect to their anti-inflammatory activity by their competition with wild type molecules for the GAG site.

Therefore, the present invention provides a method for introducing a GAG binding site into a protein characterised in that it comprises the steps:
identifying a region in a protein which is not essential for structure maintenance
introducing at least one basic amino acid into said site and/or deleting at least one bulky and/or acidic amino acid in said site, whereby said GAG binding site has a GAG binding affinity of $K_d \leq 10$ μM, preferably $\leq 1$ μM, still preferred $\leq 0.1$ μM. By introducing at least one basic amino acid and/or deleting at least one bulky and/or acidic amino acid in said region, a novel, improved "artificial" GAG binding site is introduced in said protein. This comprises the new, complete introduction of a GAG binding site into a protein which did not show a GAG binding activity before said modification. This also comprises the introduction of a GAG binding site into a protein which already showed GAG binding activity. The new GAG binding site can be introduced into a region of the protein which did not show GAG binding affinity as well as a region which did show GAG binding affinity. However, with the most preferred embodiment of the present invention, a modification of the GAG binding affinity of a given GAG binding protein is provided, said modified protein's GAG binding ability is increased compared to the wild-type protein. The present invention relates to a method of introducing a GAG binding site into a protein, a modified GAG binding protein as well as to an isolated DNA molecule, a vector, a recombinant cell, a pharmaceutical composition and the use of said modified protein.

Figures 1, 2:
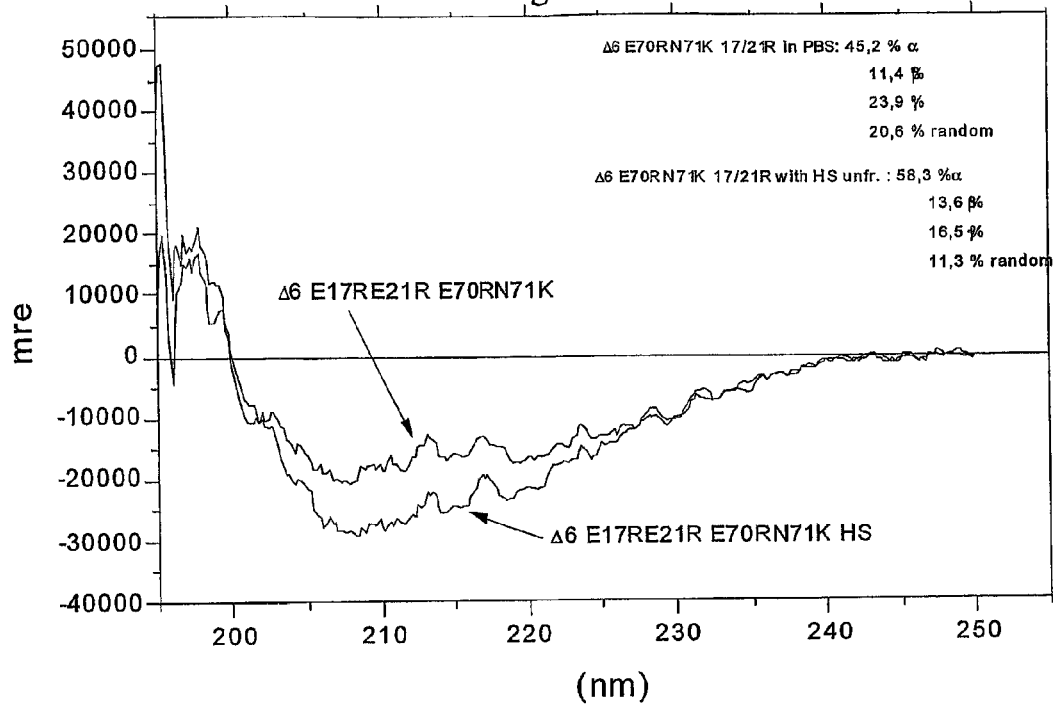
FIG. 1 shows a CD spectra.
FIG. 2 shows secondary structure contents of various mutants.

The term "introducing at least one basic amino acid" relates to the introduction of additional amino acids as well as the substitution of amino acids. The main purpose is to increase the relative amount of basic amino acids, preferably Arg, Lys, H is, Asn and/or Gln, compared to the total amount of amino acids in said site, whereby the resulting GAG binding site should preferably comprise at least 3 basic amino acids, still preferred 4, most preferred 5 amino acids.

The GAG binding site is preferably at a solvent exposed position, e.g. at a loop. This will assure an effective modification.

Whether or not a region of a protein is essential for structure maintenance, can be tested for example by computational methods with specific programmes known to the person skilled in the art. After modification of the protein, the conformational stability is preferably tested in silico.

The term "bulky amino acid" refers to amino acids with long or sterically interfering side chains; these are in particular Trp, Ile, Leu, Phe, Tyr. Acidic amino acids are in particular Glu and Asp. Preferably, the resulting GAG binding site is free of bulky and acidic amino acids, meaning that all bulky and acidic amino acids are removed.

The GAG binding affinity is determined—for the scope of protection of the present application—over the dissociation constant $K_d$. One possibility is to determine the dissociation constant ($K_d$) values of any given protein by the structural change in ligand binding. Various techniques are well known to the person skilled in the art, e.g. isothermal fluorescence titrations, isothermal titration calorimetry, surface plasmon resonance, gel mobility assay, and indirectly by competition experiments with radioactively labelled GAG ligands. A further possibility is to predict binding regions by calculation with computational methods also known to the person skilled in the art, whereby several programmes may be used.

A protocol for introducing a GAG binding site into a protein is for example as follows:
Identify a region of the protein which is not essential for overall structural maintenance and which might be suitable for GAG binding
Design a new GAG binding site by introducing (replacement or insertion) basic Arg, Lys, His, Asp and Gln residues at any position or by deleting amino acids which interfere with GAG binding
Check the conformational stability of the resulting mutant protein in silico
Clone the wild-type protein cDNA (alternatively: purchase the cDNA)
Use this as template for PCR-assisted mutagenesis to introduce the above mentioned changes into the amino acid sequence
Subclone the mutant gene into a suitable expression system (prokaryotic or eukaryotic dependent upon biologically required post-translational modifications)
Expression, purification and characterisation of the mutant protein in vitro
Criterion for an introduced GAG binding affinity: $K_d^{GAG}$ (mutant)<10 μM.

Examples of said engineered proteins with new GAG binding sites are for example the Fc part of IgG as well as the complement factors C3 and C4 modified as follows:

```
Fc:  (439)KSLSLS(444)-> KSKKLS     (SEQ ID NOS 1 & 2)

C3:  (1297)WIASHT(1302)-> WKAKHK   (SEQ ID NOS 3 & 4)

C4:  (1)MLDAERLK(8)-> MKKAKRLK     (SEQ ID NOS 5 & 6)
```

A further aspect of the present invention is a protein obtainable by the inventive method as described above. The inventive protein therefore comprises a—compared to the wild-type protein—new GAG binding site as defined above and will therefore act as competitor with natural GAG binding proteins, in particular since the GAG binding affinity of the inventive protein is very high, e.g. $K_d \leq 10$ μM.

A further aspect of the present invention is a modified GAG binding protein, whereby a GAG binding region in said protein is modified by substitution, insertion, and/or deletion of at least one amino acid in order to increase the relative amount of basic amino acids in said GAG binding region, and/or reduce the amount of bulky and/or acidic amino acids in said GAG binding region, preferably at a solvent exposed position, and in that the GAG binding affinity of said protein is increased compared to the GAG binding affinity of a respective wild-type protein.

It has been surprisingly shown that by increasing the relative amount of basic amino acids, in particular Arg, Lys, His, Asn and Gln, in the GAG binding region, the modified GAG binding protein shows increased GAG binding affinity compared to the wild-type proteins, in particular when the relative amount of basic amino acids is increased at a solvent exposed position, since a positively charged area on the protein surface has shown to enhance the binding affinity. Preferably, at least 3, still preferred 4, most preferred 5, basic amino acids are present in the GAG binding region.

The term "GAG binding protein" relates to any protein which binds to a GAG co-receptor. Whether or not a protein binds to a GAG co-receptor can be tested with the help of known protocols as mentioned above. Hileman et al. (BioEssays 20 (1998), 156-167) disclose consensus sites in glycosaminoglycan binding proteins. The information disclosed in this article is also useful as starting information for the present invention. The term "protein" makes clear that the molecules provided by the present invention are at least 80 amino acids in length. This is required for making them suitable candidates for the present anti-inflammation strategy. Smaller molecules interacting with a GAG binding site and being physiologically or pathologically relevant due to such an interaction are not known and therefore not relevant for the present invention. Preferably, the molecules according to the present invention are composed of at least 90, at least 100, at least 120, at least 150, at least 200, at least 300, at least 400 or at least 500 amino acid residues.

In the scope of the present application the term "GAG binding region" is defined as a region which binds to GAG with a dissociation constant ($K_d$-value) of under 100 μM, preferably under 50 μM, still preferred under 20 μM, as determined by isothermal fluorescence titration (see examples below).

Any modifications mentioned in the present application can be carried out with known biochemical methods, for example site-directed mutagenesis. It should also be noted that molecular cloning of GAG binding sites is, of course, prior art (see e.g. WO96/34965 A, WO 92/07935 A, Jayaraman et al. (FEBS Letters 482 (2000), 154-158), WO02/20715

A, Yang et al. (J. Cell. Biochem. 56 (1994), 455-468), wherein molecular shuffling or de novo synthesis of GAG regions are described; Butcher et al., (FEBS Letters 4009 (1997), 183-187) (relates to artificial peptides, not proteins); Jinno-Oue et al, (J. Virol. 75 (2001), 12439-12445) de novo synthesis)).

The GAG binding region can be modified by substitution, insertion and/or deletion. This means that a non-basic amino acid may be substituted by a basic amino acid, a basic amino acid may be inserted into the GAG binding region or a non-basic amino acid may be deleted. Furthermore, an amino acid which interferes with GAG binding, preferably all interfering amino acids binding is deleted. Such amino acids are in particular bulky amino acids as described above as well as acidic amino acids, for example Glu and Asp. Whether or not an amino acid interferes with GAG binding may be examined with for example mathematical or computational methods. The result of any of these modifications is that the relative amount of basic amino acids in said GAG binding region is increased, whereby "relative" refers to the amount of basic amino acids in said GAG binding region compared to the number of all amino acids in said GAG binding region. Furthermore, amino acids which interfere sterically or electrostatically with GAG binding are deleted.

Whether or not an amino acid is present in a solvent exposed position, can be determined for example with the help of the known three dimensional structure of the protein or with the help of computational methods as mentioned above.

Whether or not the GAG binding affinity of said modified protein is increased compared to the GAG binding affinity of the respective wild-type protein, can be determined as mentioned above with the help of, for example, fluorescence titration experiments which determine the dissociation constants. The criterion for improved GAG binding affinity will be $K_d$ (mutant)<$K_d$ (wild-type), preferably by at least 100%. Specifically improved modified proteins have—compared with wild-type $K_d$—a GAG binding affinity which is higher by a factor of minimum 5, preferably of minimum 10, still preferred of minimum 100. The increased GAG binding affinity will therefore preferably show a $K_d$ of under 10 µM, preferred under 1 µM, still preferred under 0.1 µM.

By increasing the GAG binding affinity the modified protein will act as a specific antagonist and will compete with the wild-type GAG binding protein for the GAG binding.

Preferably, at least one basic amino acid selected from the group consisting of Arg, Lys, and His is inserted into said GAG binding region. These amino acids are easily inserted into said GAG binding region, whereby the term "inserted" relates to an insertion as such as well as substituting any non-basic amino acid with arginine, lysine or histidine. Of course, it is possible to insert more than one basic amino acid whereby the same basic amino acid may be inserted or also a combination of two or three of the above mentioned amino acids.

Still preferred, the protein is a chemokine, preferably IL-8, RANTES or MCP-1. Chemokines are known to have a site of interaction with co-receptor GAG whereby this chemokine binding is often a condition for further receptor activation as mentioned above. Since chemokines are often found in inflammatory diseases, it is of major interest to block the chemokine receptor activation. Such chemokines are preferably IL-8, RANTES or MCP-1, which are well characterised molecules and of which the GAG binding regions are well known (see, for example, Lortat-Jacob et al., PNAS 99 (3) (2002), 1229-1234). By increasing the amount of basic amino acids in the GAG binding region of these chemokines, their binding affinity is increased and therefore the wild-type chemokines will bind less frequently or not at all, depending on the concentration of the modified protein in respect to the concentration of the wild-type protein.

According to an advantageous aspect, said GAG binding region is a C terminal α-helix. A typical chemical monomer is organised around a triple stranded anti-parallel β-sheet overlaid by a C-terminal α-helix. It has been shown that this C-terminal α-helix in chemokines is to a major part involved in the GAG binding, so that modification in this C-terminal α-helix in order to increase the amount of basic amino acids results in a modified chemokine with an increased GAG binding affinity.

Advantageously, positions 17, 21, 70, and/or 71 in IL-8 are substituted by Arg, Lys, His, Asn and/or Gln. Here it is possible that only one of these aforementioned sites is modified. However, also more than one of these sites may be modified as well as all, whereby all modifications may be either Arg or Lys or His or Asn or Gln or a mixture of those. In IL-8 these positions have shown to highly increase the GAG binding affinity of IL-8 and therefore these positions are particularly suitable for modifications.

Preferably the increased binding affinity is an increased binding affinity to heparan sulphate and/or heparin. Heparan sulphate is the most abundant member of the GAG family of linear polysaccharides which also includes heparin. Heparin is structurally very similar to heparan sulphate characterised by higher levels of post-polymerisation modifications resulting in a uniformly high degree of sulphation with a relatively small degree of structural diversity. Therefore, the highly modified blocks in heparan sulphate are sometimes referred to as heparin-like and heparin can be used as a heparan sulphate analogue for protein biophysical studies. In any case, both, heparan sulphate and heparin are particularly suitable.

Still preferred, a further biologically active region is modified thereby inhibiting or down-regulating a further biological activity of said protein. This further biological activity is known for most GAG binding proteins, for example for chemokines. This will be the binding region to a receptor, for example to the 7TM receptor. The term "further" defines a biologically active region which is not the GAG binding region which, however, binds to other molecules, cells or receptors and/or activates them. By modifying this further biologically active region the further biological activity of this protein is inhibited or down-regulated and thereby a modified protein is provided which is a strong antagonist to the wild-type protein. This means that on the one hand the GAG binding affinity is higher than in the wild-type GAG binding protein, so that the modified protein will to a large extent bind to the GAG instead of the wild-type protein. On the other hand, the further activity of the wild-type protein which mainly occurs when the protein is bound to GAG, is inhibited or down-regulated, since the modified protein will not carry out this specific activity or carries out this activity to a lesser extent. With this modified protein an effective antagonist for wild-type GAG binding proteins is provided which does not show the side effects known from other recombinant proteins as described in the state of the art. This further biologically active region can for example be determined in vitro by receptor competition assays (using fluorescently labelled wt chemokines, calcium influx, and cell migration (performed on native leukocytes or on 7TM stably-transfected cell lines). Examples of such further biologically active regions are, in addition to further receptor binding sites (as in the growth factor family), enzymatic sites (as in hydrolases, lyases, sulfotransferases, N-deacetylases, and copolymerases), protein interaction sites (as in antithrombin III), and membrane binding domains (as in the herpes simplex virus gD protein). With this preferred embodiment of double-modified proteins therefore dominant (concerning GAG binding) negative (concerning receptor) mutants are provided which are specifically advantageous with respect to the objectives set for the present invention.

Still preferred, said further biologically active region is modified by deletion, insertion, and/or substitution, preferably with alanine, a sterically and/or electrostatically similar residue. It is, of course, possible to either delete or insert or substitute at least one amino acid in said further biologically active region. However, it is also possible to provide a combination of at least two of these modifications or all three of them. By substituting a given amino acid with alanine or a sterically/electronically similar residue—"similar" meaning similar to the amino acid being substituted—the modified protein is not or only to a lesser extent modified sterically/electrostatically. This is particularly advantageous, since other activities of the modified protein, in particular the affinity to the GAG binding region, are not changed.

Advantageously, said protein is a chemokine and said further biological activity is leukocyte activation. As mentioned above, chemokines are involved in leukocyte attraction during chronic and acute inflammation. Therefore, by inhibiting or down-regulating leukocyte activation inflammation is decreased or inhibited which makes this particular modified protein an important tool for studying, diagnosing and treating inflammatory diseases.

According to an advantageous aspect, said protein is IL-8 and said further biologically active region is located within the first 10 N-terminal amino acids. The first N-terminal amino acids are involved in leukocyte activation, whereby in particular Glu-4, Leu-5 and Arg-6 were identified to be essential for receptor binding and activation. Therefore, either these three or even all first 10 N-terminal amino acids can be substituted or deleted in order to inhibit or down-regulate the receptor binding and activation.

A further advantageous protein is an IL-8 mutant with the first 6 N-terminal amino acids deleted. As mentioned above, this mutant will not or to a lesser extent bind and activate leukocytes, so that it is particularly suitable for studying, diagnosing and treating inflammatory diseases.

Preferably, said protein is an IL-8 mutant selected from the group consisting of del6F17RE70KN71R, del6F17RE70RN71K and del6E70KN71K. These mutants have shown to be particularly advantageous, since the deletion of the first 6 N-terminal amino acids inhibits or down-regulates receptor binding and activation. Furthermore, the two phenylalanines in position 17 and 21 were found to make first contact with the receptor on its N-terminal extracellular domain to facilitate the later activation of the receptor. In order to prevent any neutrophil contact, these two amino acids 17 and 21 are exchanged, whereby they are exchanged to basic amino acids, since they are in close proximity to the GAG binding motif of the C-terminal $\alpha$-helix as can be seen on a three dimensional model of a protein. By exchanging the position 17 and/or 21 to either arginine or lysine the GAG binding affinity is therefore increased.

A further aspect of the present invention is an isolated polynucleic acid molecule which codes for the inventive protein as described above. The polynucleic acid may be DNA or RNA. Thereby the modifications which lead to the inventive modified protein are carried out on DNA or RNA level. This inventive isolated polynucleic acid molecule is suitable for diagnostic methods as well as gene therapy and the production of inventive modified protein on a large scale.

Still preferred, the isolated polynucleic acid molecule hybridises to the above defined inventive polynucleic acid molecule under stringent conditions. Depending on the hybridisation conditions complementary duplexes form between the two DNA or RNA molecules, either by perfectly being matched or also comprising mismatched bases (see Sambrook et al., Molecular Cloning: A laboratory manual, $2^{nd}$ ed., Cold Spring Harbor, N.Y. 1989). Probes greater in length than about 50 nucleotides may accommodate up to 25 to 30% mismatched bases. Smaller probes will accommodate fewer mismatches. The tendency of a target and probe to form duplexes containing mismatched base pairs is controlled by the stringency of the hybridisation conditions which itself is a function of factors, such as the concentration of salt or formamide in the hybridisation buffer, the temperature of the hybridisation and the post-hybridisation wash conditions. By applying well-known principles that occur in the formation of hybrid duplexes conditions having the desired stringency can be achieved by one skilled in the art by selecting from among a variety of hybridisation buffers, temperatures and wash conditions. Thus, conditions can be selected that permit the detection of either perfectly matched or partially mismatched hybrid duplexes. The melting temperature (Tm) of a duplex is useful for selecting appropriate hybridisation conditions. Stringent hybridisation conditions for polynucleotide molecules over 200 nucleotides in length typically involve hybridising at a temperature 15-25° C. below the melting temperature of the expected duplex. For oligonucleotide probes over 30 nucleotides which form less stable duplexes than longer probes, stringent hybridisation usually is achieved by hybridising at 5 to 10° C. below the Tm. The Tm of a nucleic acid duplex can be calculated using a formula based on the percent G+C contained in the nucleic acids and that takes chain lengths into account, such as the formula $Tm=81.5-16.6 (\log [Na^+)])+0.41 (\% G+C)-(600/N)$, where N=chain length.

A further aspect of the present invention relates to a vector which comprises an isolated DNA molecule according to the present invention as defined above. The vector comprises all regulatory elements necessary for efficient transfection as well as efficient expression of proteins. Such vectors are well known in the art and any suitable vector can be selected for this purpose.

A further aspect of the present application relates to a recombinant cell which is stably transfected with an inventive vector as described above. Such a recombinant cell as well as any therefrom descendant cell comprises the vector. Thereby a cell line is provided which expresses the modified protein either continuously or upon activation depending on the vector.

A further aspect of the present invention relates to a pharmaceutical composition which comprises a protein, a polynucleic acid or a vector according to the present invention as defined above and a pharmaceutically acceptable carrier. Of course, the pharmaceutical composition may further comprise additional substances which are usually present in pharmaceutical compositions, such as salts, buffers, emulgators, colouring agents, etc.

A further aspect of the present invention relates to the use of the modified protein, a polynucleic acid or a vector according to the present invention as defined above in a method for inhibiting or suppressing the biological activity of the respective wild-type protein. As mentioned above, the modified protein will act as an antagonist whereby the side effects which occur with known recombinant proteins will not occur with the inventive modified protein. In the case of chemokines this will be in particular the biological activity involved in inflammatory reactions.

Therefore, a further use of the modified protein, polynucleic acid or vector according to the present invention is in a method for producing a medicament for the treatment of an inflammatory condition. In particular, if the modified protein is a chemokine, it will act as antagonist without side effects and will be particularly suitable for the treatment of an inflammatory condition. Therefore, a further aspect of the present application is also a method for the treatment of an inflammatory condition, wherein a modified protein according to the present invention, the isolated polynucleic acid molecule or vector according to the present invention or a pharmaceutical composition according to the present invention is administered to a patient.

Preferably, the inflammatory condition is selected from a group comprising rheumatoid arthritis, psoriasis, osteoarthritis, asthma, Alzheimer's disease, and multiple sclerosis. Since the activation through chemokines can be inhibited with a modified protein according to the present invention, inflammatory reactions can be inhibited or down-regulated whereby the above mentioned inflammatory conditions can be prevented or treated.

Figure 3:
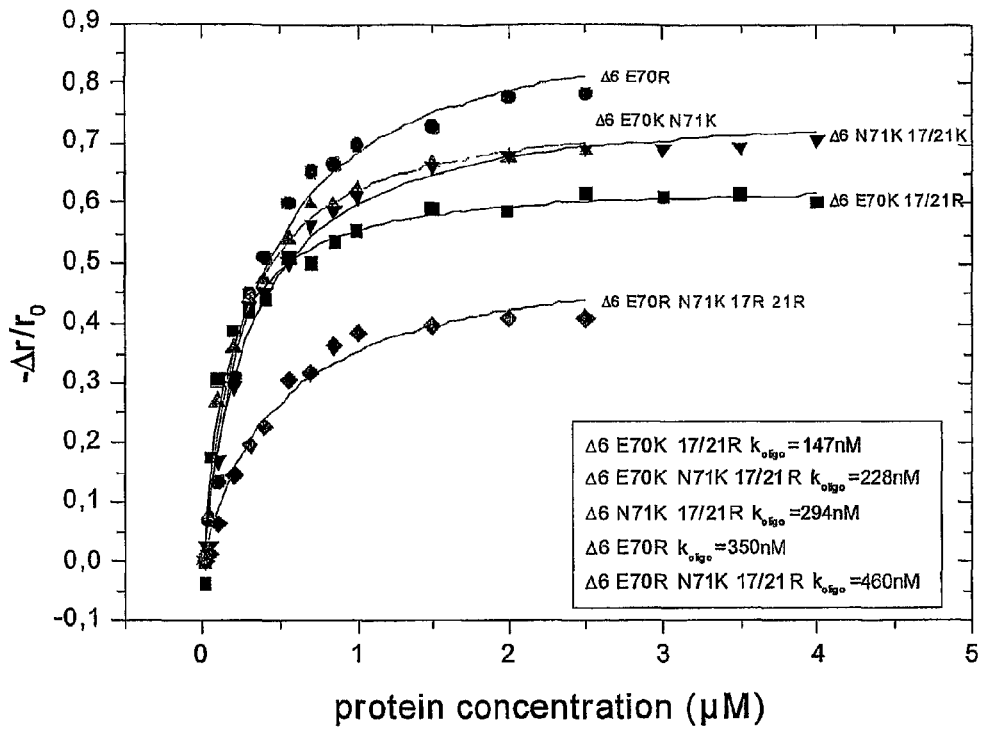
FIG. 3 shows graphics of results from fluorescence anisotropy tests of various mutants.
Figure 4:
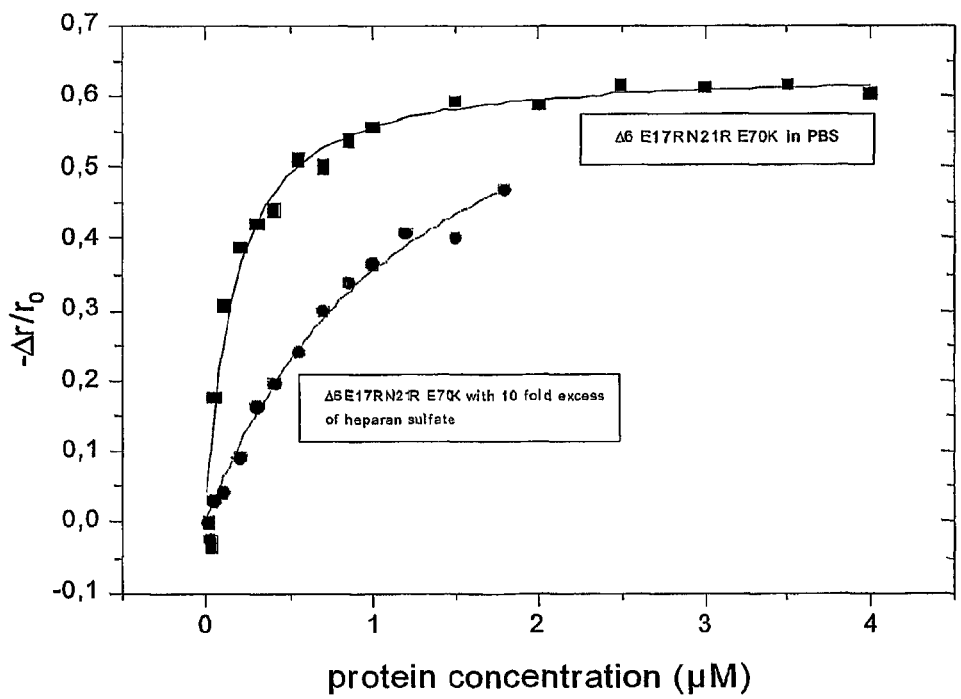
FIG. 4 shows graphics of results from fluorescence anisotropy tests of two mutants.
Figure 5:
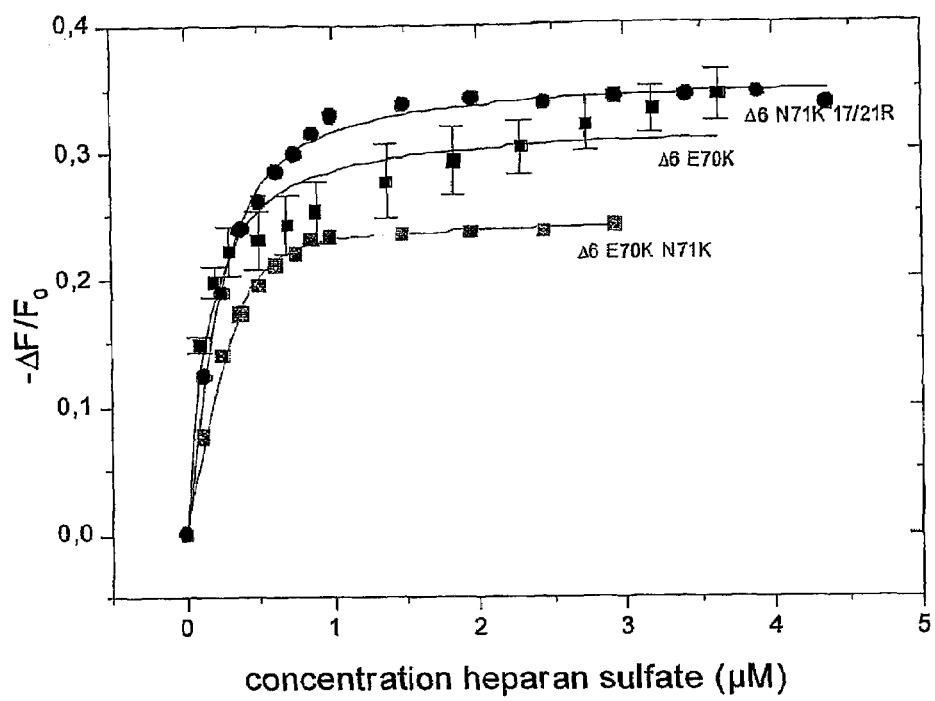
FIG. 5 shows the graphic of results from isothermal fluorescence titrations.
Figure 6:
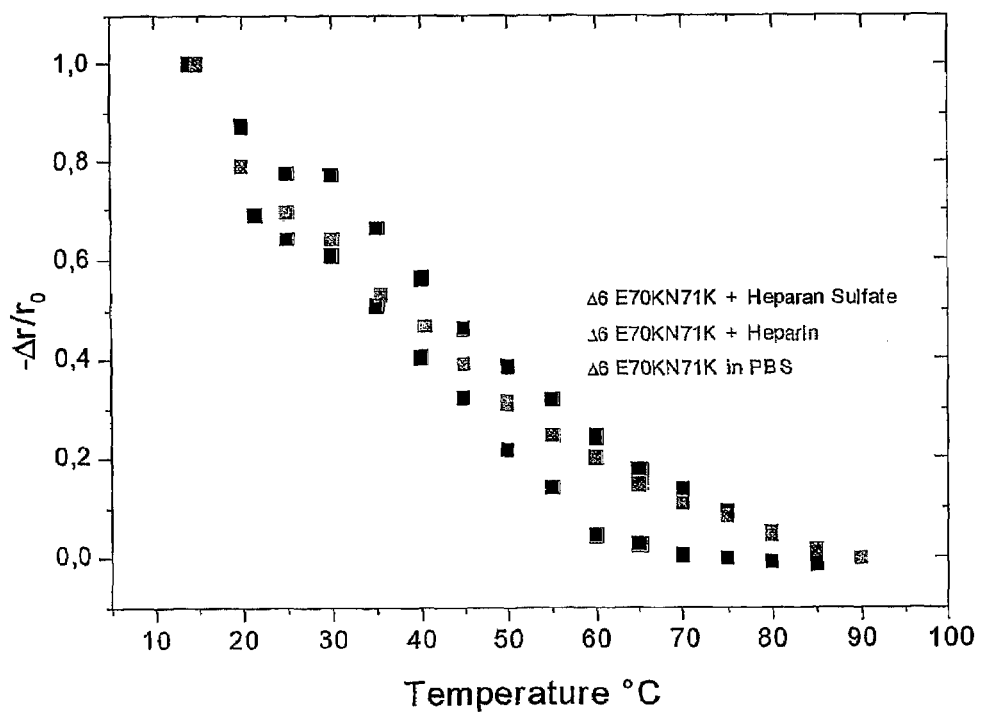
FIG. 6 shows the graphic of results from unfolding experiments of various mutants.
Figure 7:
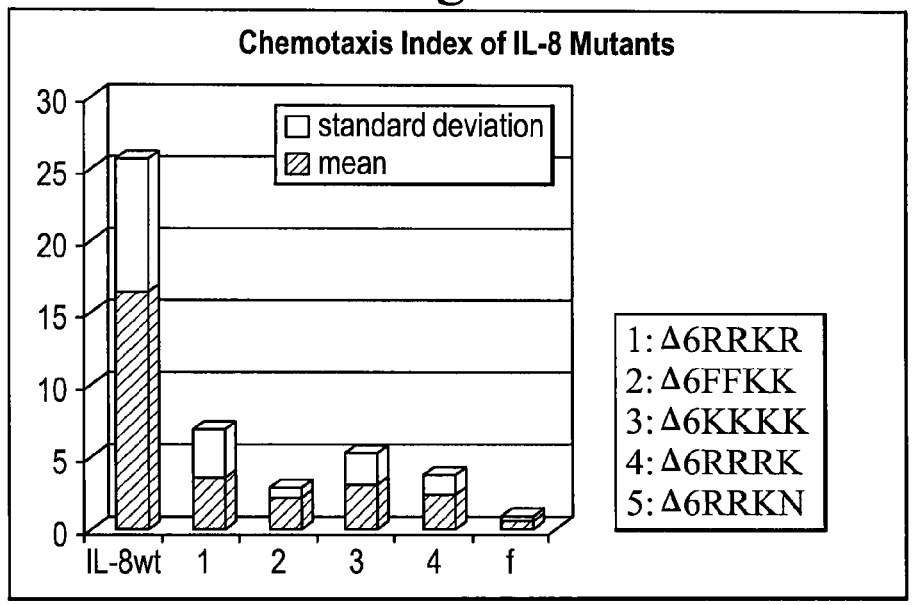
FIG. 7 shows chemotaxis index of IL-8 mutants.
Figure 8:
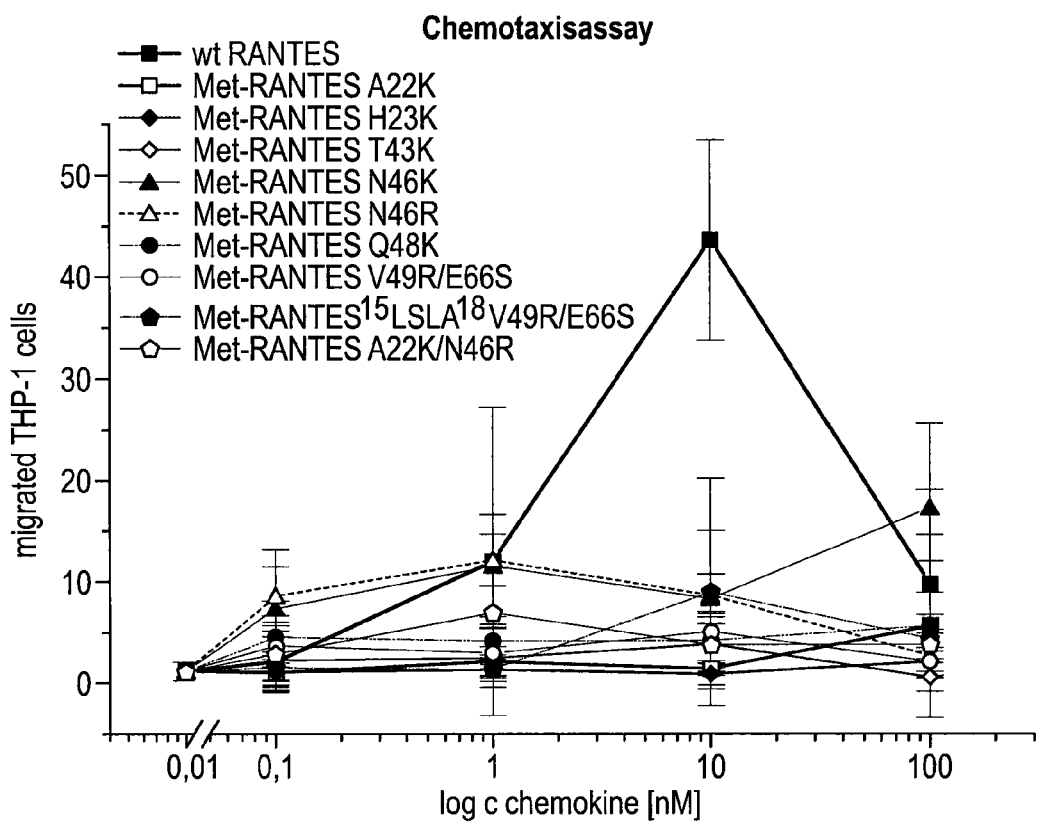
FIG. 8 shows the results of the RANTES chemotaxis assay."

The present invention is described in further detail with the help of the following examples and figures to which the invention is, however, not limited whereby FIG. 1 is a CD spectra; FIG. 2 shows secondary structure contents of various mutants; FIGS. 3 and 4 show graphics of results from fluorescence anisotropy tests of various mutants; FIG. 5 shows the graphic of results from isothermal fluorescence titrations; FIG. 6 shows the graphic of results from unfolding experiments of various mutants, FIG. 7 shows chemotaxis index of IL-8 mutants (SEQ ID NOS 1070-1074 are disclosed respectively in order of appearance), and FIG. 8 shows the results of the RANTES chemotaxis assay.

EXAMPLES

Example 1

Generation of Recombinant IL-8 Genes and Cloning of the Mutants

Polymerase chain reaction (PCR) technique was used to generate the desired cDNAs for the mutants by introducing the mutations using sense and antisense mutagenesis primers. A synthetic plasmid containing the cDNA for wtIL-8 was used as template, Clontech Advantage®2 Polymerase Mix applied as DNA polymerase and the PCR reaction performed using a Mastergradient Cycler of Eppendorf. The mutagenesis primers used are summarised in the table below beginning with

```
the forward sequences (5'to 3'):
                                            (SEQ ID NO: 7)
CACC ATG TGT CAG TGT ATA AAG ACA TAC TCC (primer for the mutation Δ6)

(SEQ ID NO: 8)
CACC ATG TGT CAG TGT ATA AAG ACA TAC TCC AAA CCT

AGG CAC CCC AAA AGG ATA (primer for the mutation Δ6 F17R F21R)

The reverse sequences are (5' to 3'):
                                            (SEQ ID NO: 9)
TTA TGA ATT CCT AGC CCT CTT (primer for the mutation E70R)
```

```
                                            (SEQ ID NO: 10)
TTA TGA ATT CTT AGC CCT CTT (primer for the mutation E70K)

(SEQ ID NO: 11)
TTA TGA CTT CTC AGC CCT CTT (primer for the mutation N71K)

(SEQ ID NO: 12)
TTA TGA CTT CTT AGC CCT CTT (primer for the mutation E70K N71K)

(SEQ ID NO: 13)
TTA TGA CTT CCT AGC CCT CTT (primer for the mutation E70R N71K)

(SEQ ID NO: 14)
TTA TGA CCT CTT AGC CCT CTT (primer for the mutation E70K N71R)

(SEQ ID NO: 15)
TTA TGA CCT CCT AGC CCT CTT (primer for the mutation E70R N71R)
```

The PCR products were purified, cloned into the pCR®T7/NT-TOPO®TA (Invitrogen) vector and transformed into TOP10F competent *E. coli* (Invitrogen). As a next step a confirmation of the sequence was carried out by double-stranded DNA sequencing using a ABI PRISM CE1 Sequencer.

Example 2

Expression and Purification of the Recombinant Proteins

Once the sequences were confirmed, the constructs were transformed into calcium-competent BL21(DE3) *E. coli* for expression. Cells were grown under shaking in 1 l Lennox Broth (Sigma) containing 100 µg/ml Ampicillin at 37° C. until an $OD_{600}$ of about 0.8 was reached. Induction of protein expression was accomplished by addition of isopropyl-β-D-thiogalactopyranoside (IPTG) to a final concentration of 1 mM. Four hours later the cells were harvested by centrifugation at 6000 g for 20 minutes. The cell pellet was then resuspended in a buffer containing 20 mM TRIS/HCl, 50 mM NaCl, pH 8, sonicated at 100 watts for 5×20 s and finally centrifuged again for 20 min at 10,000 g. Since the main fraction of the recombinant IL-8 proteins was found in inclusion bodies, denaturing conditions were chosen for further purification. So the cell pellet was resuspended in a buffer of 6M Gua/HCl and 50 mM MES, pH 6.5. The suspension was then stirred at 4° C. for 4 hours, followed by a dialysis step against 50 mM MES, pH 6.5. The resulting suspension was then centrifuged and filtered to be loaded on a strong cation exchange column (SP Sepharose® from Pharmacia Biotech). The elution was accomplished by a linear gradient from 0M-1M NaCl in a 50 mM MES buffer, pH 6.5 over 60 minutes. After lyophilisation of the fractions containing the desired protein, a second purification step was carried out by reversed-phase HPLC using a C18 column. In this case a non-linear gradient from 10%-90% Acetonitril was chosen to elute the desired protein. Refolding of the denatured protein was finally accomplished by the same cation exchange column under the same conditions as described above.

The protein was then checked for purity and identity by silver stain analysis in the first case and Western Blot analysis, using a specific monoclonal antibody against wtIL-8, in the second. Refolding of the proteins was also confirmed by Circular Dichroism (CD) measurements.

Example 3

Biophysical Characterisation of the Mutants 3.1 Circular Dicroism Measurements and Analysis In order to investigate secondary structure changes of the mutant protein in the presence and absence of heparan sulphate (HS), CD spectroscopy was carried out. Measurements were recorded on a Jasco J-710 spectropolarimeter over a range of 195-250 nm, and a cell of 0.1 cm path length was used. Spectra of the protein solutions with a concentration of 5 µM were recorded with a response time of 1 s, step resolution of 0.2 nm, speed of 50 nm/min, band width of 1 nm and a sensitivity of 20 mdeg. Three scans were averaged to yield smooth spectra. The protein spectra were then background-corrected relating to the CD-signal either of the buffer itself or buffer/HS. Secondary structure analysis of the protein in the presence and absence of HS was finally accomplished using the programme SELCON.

Since a great number of amino acids were changed in a number of novel combinations, it was tried to find out the dimension of the resulting secondary structure changes by circular dichroism methods.

Different structures were obtained depending on the mutations introduced. Except for one mutant expressed (Δ6 F17R F21R E70K N71R) which didn't show any structure, all mutants exhibited measurable α-helices, β-sheets and loops. Compared to IL-8 wt only one mutant (Δ6 E70R) showed nearly similar structure whereas the others differed mainly in their α-helix which ranged from 17.2% to 45.2% out of the total structure. Nevertheless, this fact suggests that the overall structure of IL-8 wt was maintained despite many changes within the proteins sequence. This could not have been previously predicted. Having already found that heparan sulphate oligosaccharides only, and not heparin, were able to affect IL-8 wt secondary structure, attention was focused on the effects induced by unfractionated heparan sulphate. All examined mutants showed structural changes upon HS binding which can be seen as evidence of complex formation.

To demonstrate the structural changes upon introduced mutations and heparan sulphate addition, some of the data obtained are summarised in the graphs above and below.

3.2 Fluorescence Measurements

For studying concentration and ligand dependent quaternary structure changes fluorescence spectroscopy was performed. Due to its high sensitivity, requiring only nanogram quantities of protein, fluorescence technique was the method of choice for carrying out the desired investigations. Measurements were undertaken using a Perkin-Elmer (Beaconsfield, England) LS50B fluorometer.

3.3 Fluorescence Anisotropy

By recording the concentration dependent fluorescence anisotropy of the chemokine resulting from the extrinsic chromophore bisANS it was aimed to find out the dimerisation constant of the mutants. Measurements were performed in PBS starting with high concentrations (up to 4 µM protein) followed by stepwise dilution. For each data point, the anisotropy signal (r) recorded at 507 nm was averaged over 60 sec.

IL-8 oligomerisation has been reported to relevantly influence the proteins GAG binding properties. Set at monomeric concentration, IL-8 bound size defined oligosaccharides 1000-fold tighter than at dimeric concentration. Therefore, the oligomerisation properties of IL-8 mutants were investigated by fluorescence anisotropy. Since the IL-8 intrinsic fluorophore (Trp57) was not sensitive enough for all of the mutants, the extrinsic fluorophore bis-ANS was used for these measurements. Again, as already noticed for the secondary structure, the mutant Δ6 E70R showed high resemblance also in the oligomerisation constant ($k_{oligo}$=350 nM) to IL-8 wt ($k_{oligo}$=379 nM). The mutant with the highest $k_{oligo}$ ($k_{oligo}$=460 nM), which therefore dimerised worst, was Δ6 F17RF21R E70RN71K. Previous studies identified the β-sheets to be mainly involved in the dimerisation process, a fact, which correlates with the results for this mutants' secondary structure, which showed a very low share of β-sheet of only 11.4%. The mutant with the lowest $k_{oligo}$ ($k_{oligo}$=147 nM), was found to be Δ6 F17RF21R E70K, which again showed the highest share of β-sheet structure (29.8%) of all mutants investigated. Also the impact of heparan sulphate addition was observed. As for IL-8 wt, where heparan sulphate caused a shift of the oligomerisation constant to much higher levels ($k_{oligo}$=1.075 µM), this was also found for the IL-8 mutants investigated. Δ6 F17RF21R E70K shifted from 0.147 µM to 1.162 µM, and the mutant Δ6 E70R from 0.350 µM to 1.505 µM in the presence of heparan sulphate. Some of the results obtained are demonstrated in FIGS. 3 and 4, whereby FIG. 3 shows the dependence of the fluorescence anisotropy of IL-8 mutants in PBS on the chemokine concentration and FIG. 4 shows the dependence of the fluorescence anisotropy of Δ6 F17RF21R E70K in PBS on the chemokine concentration in the presence (ten fold excess) and absence of HS ((pc=10 xy excess) protein concentration).

3.4 Isothermal Fluorescence Titration (IFT) Experiments

Dissociation constants ($K_d$ values) are a measure for the binding affinity of a ligand to a protein and therefore concentration-dependent change in the fluorescence emission properties of the protein (fluorescence quenching) upon ligand binding was used for the determination of $K_d$. Since these mutants contain an intrinsic tryptophan chromophore which is located at or near the proposed GAG binding site and therefore should be sensitive to structural changes upon ligand binding, IFT experiments seemed to be suitable for this kind of investigation. Fluorescence intensity titration was performed in PBS using a protein concentration of 700 nM. The emission of the protein solution upon excitation at 282 nm was recorded over a range of 300-400 nm following the addition of an aliquot of the respective GAG ligand and an equilibration period of 60 sec.

Binding to unfractionated heparin and heparan sulphate was investigated. The mutants were set at dimeric concentration to assure sufficient sensitivity. A quenching of Trp57 fluorescence intensity upon GAG binding was registered within a range of 25-35%. Significant improvement of ligand binding was observed, especially for heparin binding. Δ6 F17RN71R E70K ($K_d$=14 nM) and Δ6 F17RF21R N71K ($K_d$=14.6 nM) showed 2600-fold better binding, and Δ6 E70K N71K ($K_d$=74 nM) 1760-fold better binding compared to IL-8 wt ($K_d$=37 µM). Good results were also obtained for heparan sulphate binding. For Δ6 F17RN71R E70K a $K_d$ of 107 nM was found, for Δ6 F17RF21R N71K the $K_d$ was 95 nM and the mutant Δ6 E70K N71K showed a $K_d$ of 34 nM. As IL-8 wt binds with a $K_d$ of 4.2 µM, the $K_d$s found for the mutants represent an extraordinary improvement in binding, see FIG. 5.

3.5 Unfolding Experiments

In order to obtain information about the proteins stability and whether this stability would be changed upon GAG ligand binding, unfolding experiments were undertaken. As mentioned above fluorescence techniques are very sensitive for observing quaternary structure changes and therefore are also the method of choice to investigate thermal structural changes of the protein. Measurements were undertaken as described for the IFT in which not the ligand concentration was changed but the temperature. Protein structure was observed at a concentration of 0.7 µM from temperatures of 15-85° C. in the absence and the presence of a 10 fold excess of heparan sulphate or heparin.

The emission maximum of the proteins ranged from 340 nm to 357 nm, values which are typical for a solvent exposed tryptophan residue. Beginning with the unfolding experiments at 15° C., the emission maximum of the mutants varied between 340 nm-351 nm. Compared to IL-8 wt, whose emission maximum was observed at 340 nm, this means slightly higher values. Upon an increase in temperature, the intensity of emission maximum decreased, accompanied by a shift of the maximum to either a higher or lower wavelength. The emission maximum of Δ6 E70R and Δ6 E70K N71K shifted from 352.5 nm-357 nm and 343 nm-345 nm, which is typical for a further exposure of the Trp57 residue to the solvent trough temperature increase, but interestingly the mutants Δ6 F17RN71R E70K and Δ6 F17RF21R E70R N71K showed a blue shift, ranging from 350 nm-343 nm and, less pronounced, from 350 nm-348 nm (see FIG. 6). By slowly decreasing the temperature, the process of unfolding was partially reversible regarding both the wavelength shift and changes of intensity. Addition of a 5 fold excess of heparan sulphate led to an increase of stability of the proteins, probably through complex formation. This could be observed on the one hand by a shift of the melting point to higher temperature, and on the other hand by a significantly less pronounced shift of emission maximum upon temperature increase.

Example 4

Cell-Based Assay of the Receptor-"Negative" Function of the Dominant-Negative IL-8 Mutants In order to characterise the impaired receptor function of the IL-8 mutants with respect to neutrophil attraction, transfilter-based chemotaxis of neutrophils in response to IL-8 mutants was assayed in a microchemotaxis chamber equipped with a 5 µm PVP-free polycarbonate membrane.

Cell Preparation:

Briefly, a neutrophil fraction was prepared from freshly collected human blood. This was done by adding a 6% dextran solution to heparin-treated blood (1:2) which was then left for sedimentation for 45 min. The upper clear cell solution was collected and washed twice with HBSS w/o Ca and Mg. Cells were counted and finally diluted with HBSS at 2 Mio/ml cell suspension, taking into account that only 60% of the counted cells were neutrophils.

Chemotaxis Assay:

IL-8 mutants were diluted at concentrations of 10 µg/ml, 1 µg/ml and 0.1 µg/ml and put in triplicates in the lower compartment of the chamber (26 µl per well). The freshly prepared neutrophils were seeded in the upper chamber (50 µl per well) and incubated for 30 minutes at 37° C. in a 5% $CO_2$ humidified incubator. After incubation, the chamber was disassembled, the upper side of the filter was washed and wiped off and cells attached to the lower side were fixed with methanol and stained with Hemacolor solutions (Merck). Cells were then counted at 400× magnifications in 4 randomly selected microscopic fields per well. Finally, the mean of three independent experiments was plotted against the chemokine concentration. In FIG. 7, the chemotaxis index for various IL-8 mutants is shown. As expected, all mutants showed significantly decreased receptor binding activity.

Example 5

Generation of Recombinant RANTES Genes, Expression, Biophysical and Activity Characterisation of the Mutants The concept of dominant-negative "GAG-masking" chemokine mutants was also employed to RANTES, a chemokine involved in type IV hypersensitivity reactions like transplant rejection, atopic dermatitis as well as in other inflammatory disorders like arthritis, progressive glomerulonephritis and inflammatory lung disease.

The receptor binding capability was impaired by introducing into the wt protein an initiating methionine residue. Expression of the wt RANTES in *E. Coli* lead to the retention of this methionine residue, which renders wt RANTES to a potent inhibitor of monocyte migration, the so-called Met-RANTES. Different mutations enhancing the GAG binding affinity were introduced via PCR-based site-directed mutagenesis methods.

By these means 9 RANTES mutants have so far been cloned, expressed and purified, Met-RANTES A22K, Met-RANTES H23K, Met-RANTES T43K, Met-RANTES N46R, Met-RANTES N46K, Met-RANTES Q48K, Met-RANTES A22K/N46R, Met-RANTES V49R/E66S and Met-RANTES $^{15}$LSLA$^{18}$ V49R/E66S.

Isothermal fluorescence titration experiments were carried out to measure the relative affinity constants (Kd values) of the RANTES mutants for size defined heparin. As can be seen in the table all RANTES mutant proteins showed higher affinities for this heparin, with Met-RANTES A22K, Met-RANTES H23K, Met-RANTES T43K and Met-RANTES A22K/N46R showing the most promising results.

|                         | Kd in nM       |
|-------------------------|----------------|
| Wt Rantes               | 456.2 ± 8.5    |
| Met-Rantes V49R/E66S    | 345.5 ± 21.7   |
| Rantes 15LSLA18 V49R/66S| 297.3 ± 14.1   |
| Rantes N46R             | 367.7 ± 11.7   |
| Rantes N46K             | 257.4 ± 10.2   |
| Rantes H23K             | 202.5 ± 12.8   |
| Rantes Q48K             | 383.4 ± 39.6   |
| Rantes T43K             | 139.2 ± 30.1   |
| Rantes A22K             | 202.1 ± 9.8    |
| Rantes A22K/N46R        | 164.0 ± 16.6   |

RANTES Chemotaxis Assay

RANTES mutant directed cell migration was investigated using the 48-well Boyden chamber system equipped with 5 µm PVP-coated polycarbonate membranes. RANTES and RANTES mutant dilutions in RPMI 1640 containing 20 mM HEPES pH 7.3 and 1 mg/ml BSA were placed in triplicates in the lower wells of the chamber. 50 µl of THP-1 cell suspensions (promonocytic cell line from the European collection of cell cultures) in the same medium at 2×10$^6$ cells/ml were placed in the upper wells. After a 2 h incubation period at 37°

C. in 5% $CO_2$ the upper surface of the filter was washed in HBSS solution. The migrated cells were fixed in methanol and stained with Hemacolor solution (Merck). Five 400× magnifications per well were counted and the mean of three independently conducted experiments was plotted against the chemokine concentration in FIG. 8. The error bars represent the standard error of the mean of the three experiments. Again, as in the case of the IL-8 mutants, all RANTES mutants showed significantly reduced receptor binding activity.

Example 6

Proteins with GAG Binding Regions

By bioinformatical and by proteomical means GAG binding proteins were characterised together with their GAG binding regions. In the following tables 2 and 3 chemokines are shown with their GAG binding regions (table 2) and examples of other proteins are given also with their GAG binding regions (table 3).

TABLE 2

Chemokines and their GAG binding domains

CXC - chemokines

IL-8: $^{18}$HPK$^{20}$, (R47) $^{60}$RVVEKFLKR$^{68}$
(residues 60-68 of SEQ ID NO: 16)

(SEQ ID NO: 16)
SAKELRCQCIKTYSKPFHPKFIKELRVIESGPHCANTEIIVKLSDGRELC
LDPKENWVQRVVEKFLKRAENS

MGSA/GROα: $^{19}$HPK$^{21}$, $^{45}$KNGR$^{48}$
(residues 45-48 of SEQ ID NO: 17), $^{60}$KKIIEK$^{66}$
(residues 60-66 of SEQ ID NO: 17)

(SEQ ID NO: 17)
ASVATELRCQCLQTLQGIHPKNIQSVNVKSPGPHCAQTEVIATLKNGRKA
CLNPASPIVKKIIEKMLNSDKSN

MIP-2α/GROβ: $^{19}$HLK$^{21}$, K45, $^{60}$KKIIEKMLK$^{68}$
(residues 60-68 of SEQ ID NO: 18)

(SEQ ID NO: 18)
APLATELRCQCLQTLQGIHLKNIQSVKVKSPGPHCAQTEVIATLKNGQKA
CLNPASPMVKKIIEKMLKNGKSN

NAP-2: $^{15}$HPK$^{18}$, $^{42}$KDGR$^{45}$
(residues 42-45 of SEQ ID NO: 19), $^{57}$KKIVQK$^{62}$
(residues 57-62 of SEQ ID NO: 19)

(SEQ ID NO: 19)
AELRCLCIKTTSGIHPKNIQSLEVIGKGTHCNQVEVIATLKDGRKICLDP
DAPRIKKIVQKKLAGDESAD

PF-4: $^{20}$RPRH$^{23}$
(residues 20-23 of SEQ ID NO: 20), $^{46}$KNGR$^{49}$
(residues 46-49 of SEQ ID NO: 20), $^{61}$KKIIKK$^{66}$
(residues 61-66 of SEQ ID NO: 20)

(SEQ ID NO: 20)
EAEEDGDLQCLCVKTTSQVRPRHITSLEVIKAGPHCPTAQLIATLKNGRK
ICLDLQAPLYKKIIKKLLES

SDF-1α: K1, $^{24}$KHLK$^{27}$

TABLE 2-continued

Chemokines and their GAG binding domains (residues 24-27 of SEQ ID NO: 21), $^{41}$RLK$^{43}$ (SEQ ID NO: 21)
KPVSLSYRCPCRFFESHVARANVKHLKILNTPNCALQIVARLKNNNRQVC
IDPKLKWIQEYLEKALN CC - chemokines RANTES: ($^{17}$RPLPRAH$^{23}$ (residues 17-23 of SEQ ID NO: 22))

$^{44}$RKNR$^{47}$
(residues 44-47 of SEQ ID NO: 22)

(SEQ ID NO: 22)
SPYSSDTTPCCFAYIARPLPRAHIKEYFYTSGKCSNPAVFVTRKNRQVCA
NPEKKWVREYINSLEMS

MCP-2: $^{18}$RKIPIQR$^{24}$
(residues 18-24 of SEQ ID NO: 23), $^{46}$KRGK$^{49}$
(residues 46-49 of SEQ ID NO: 23)

(SEQ ID NO: 23)
QPDSVSIPITCCFNVINRKIPIQRLESYTRITNIQCPKEAVIFKTKRGKE
VCADPKERWVRDSMKHLDQIFQNLKP

MCP-3: $^{22}$KQR$^{24}$, $^{47}$KLDK$^{50}$
(residues 47-50 of SEQ ID NO: 24), $^{66}$KHLDKK$^{71}$
(residues 66-71 of SEQ ID NO: 24)

(SEQ ID NO: 24)
QPVGINTSTTCCYRFINKKIPKQRLESYRRTTSSHCPREAVIFKTKLDKE
ICADPTQKWVQDFMKHLDKKTQTPKL

MIP-1α: R17, $^{44}$KRSR$^{47}$
(residues 44-47 of SEQ ID NO: 25)

(SEQ ID NO: 25)
SLAADTPTACCFSYTSRQIPQNFIADYFETSSQCSKPGVIFLTKRSRQVC
ADPSEEWVQKYVSDLELSA

MIP-1β: R18, $^{45}$KRSK$^{48}$
(residues 45-48 of SEQ ID NO: 26)

(SEQ ID NO: 26)
APMGSDPPTACCFSYTARKLPRNFVVDYYETSSLCSQPAVVFQTKRSKQV
CADPSESWVQEYVYDLELN

MPIF-1: R18, $^{45}$KKGR$^{48}$
(residues 45-48 of SEQ ID NO: 27)

(SEQ ID NO: 27)
MDRFHATSADCCISYTPRSIPCSLLESYFETNSECSKPGVIFLTKKGRRF
CANPSDKQVQVCMRMLKLDTRIKTRKN

MIP-5/HCC-2: $^{40}$KKGR$^{43}$
(residues 40-43 of SEQ ID NO: 28)

(SEQ ID NO: 28)
HFAADCCTSYISQSIPCSLMKSYFETSSECSKPGVIFLTKKGRQVCAKPS
GPGVQDCMKKLKPYSI

TABLE 3

| | SEQ ID NO: | | |
|---|---|---|---|
| Peroxisome biogenesis factor 1 | 29 | 181 | TRRAKE 186 |
| | 30 | 367 | QKKIRS 372 |
| | 31 | 1263 | PKRRKN 1268 |
| | 32 | 181 | TRRAKE 186 |
| | 33 | 367 | QKKIRS 372 |
| | 34 | 1263 | PKRRKN 1268 |
| MLTK-beta | 35 | 415 | SKRRGKKV 422 |
| | 36 | 312 | ERRLKM 317 |
| | 37 | 416 | KRRGKK 421 |
| | 38 | 312 | ERRLKM 317 |
| | 39 | 416 | KRRGKK 421 |
| BHLH factor Hes4 | 40 | 43 | EKRRRARI 50 |
| | 41 | 43 | EKRRRA 48 |
| | 42 | 43 | EKRRRA 48 |
| Protocadherin 11 | 43 | 867 | MKKKKKKK 874 |
| | 44 | 867 | MKKKKK 872 |
| | 45 | 867 | MKKKKK 872 |
| | 46 | 899 | MKKKKKKK 906 |
| | 47 | 899 | MKKKKK 904 |
| | 48 | 899 | MKKKKK 904 |
| catenin (cadherin-associated protein) delta 1 | 49 | 315 | RRRLRS 320 |
| | 50 | 404 | VRKLKG 409 |
| | 51 | 460 | LRKARD 465 |
| | 52 | 545 | RRKLRE 550 |
| | 53 | 621 | AKKGKG 626 |
| | 54 | 787 | AKKLRE 792 |
| | 55 | 315 | RRRLRS 320 |
| | 56 | 404 | VRKLKG 409 |
| | 57 | 460 | LRKARD 465 |
| | 58 | 545 | RRKLRE 550 |
| | 59 | 621 | AKKGKG 626 |
| | 60 | 787 | AKKLRE 792 |
| Muscarinic acetylcholine receptor M5 | 61 | 221 | EKRTKD 226 |
| | 62 | 427 | TKRKRV 432 |
| | 63 | 514 | WKKKKV 519 |
| | 64 | 221 | EKRTKD 226 |
| | 65 | 427 | TKRKRV 432 |
| | 66 | 514 | WKKKKV 519 |
| Alpha-2A adrenergic receptor | 67 | 147 | PRRIKA 152 |
| | 68 | 224 | KRRTRV 229 |
| | 69 | 147 | PRRIKA 152 |
| | 70 | 224 | KRRTRV 229 |
| IL-5 promoter REII-region-binding protein | 71 | 440 | TKKKTRRR 447 |
| | 72 | 569 | GKRRRRRG 576 |
| | 73 | 38 | ARKGKR 43 |
| | 74 | 437 | GKKTKK 442 |
| | 75 | 444 | TRRRRA 449 |
| | 76 | 569 | GKRRRR 574 |
| | 77 | 38 | ARKGKR 43 |
| | 78 | 437 | GKKTKK 442 |
| | 79 | 444 | TRRRRA 449 |
| | 80 | 569 | GKRRRR 574 |
| Mitofusin 1 | 81 | 291 | ARKQKA 296 |
| | 82 | 395 | KKKIKE 400 |
| | 83 | 291 | ARKQKA 296 |
| | 84 | 395 | KKKIKE 400 |
| N-cym protein | 85 | 71 | VRRCKI 76 |
| | 86 | 71 | VRRCKI 76 |
| Smad ubiquitination regulatory factor 1 | 87 | 672 | ERRARL 677 |
| | 88 | 672 | ERRARL 677 |
| CUG-BP and ETR-3 like factor 5 | 89 | 468 | MKRLKV 473 |
| | 90 | 475 | LKRPKD 480 |
| | 91 | 468 | MKRLKV 473 |
| | 92 | 475 | LKRPKD 480 |

TABLE 3-continued

| | SEQ ID NO: | | |
|---|---|---|---|
| Ewings sarcoma EWS-Fli1 | 93 | 347 | QRKSKP 352 |
| | 94 | 347 | QRKSKP 352 |
| NUF2R | 95 | 455 | LKRKMFKM 462 |
| | 96 | 331 | LKKLKT 336 |
| | 97 | 347 | VKKEKL 352 |
| | 98 | 331 | LKKLKT 336 |
| | 99 | 347 | VKKEKL 352 |
| Kruppel-like zinc finger protein GLIS2 | 100 | 22 | EKRERT 27 |
| | 101 | 22 | EKRERT 27 |
| FKSG32 | 102 | 15 | LKRVRE 20 |
| | 103 | 431 | VRRGRI 436 |
| | 104 | 15 | LKRVRE 20 |
| | 105 | 431 | VRRGRI 436 |
| BARH-LIKE 1 PROTEIN | 106 | 175 | LKKPRK 180 |
| | 107 | 228 | NRRTKW 233 |
| | 108 | 175 | LKKPRK 180 |
| | 109 | 228 | NRRTKW 233 |
| Nucleolar GTP-binding protein 1 | 110 | 393 | SRKKRERD 400 |
| | 111 | 624 | GKRKAGKK 631 |
| | 112 | 48 | MRKVKF 53 |
| | 113 | 141 | IKRQKQ 146 |
| | 114 | 383 | ARRKRM 388 |
| | 115 | 393 | SRKKRE 398 |
| | 116 | 490 | KKKLKI 495 |
| | 117 | 543 | ARRSRS 548 |
| | 118 | 550 | TRKRKR 555 |
| | 119 | 586 | VKKAKT 591 |
| | 120 | 629 | GKKDRR 634 |
| | 121 | 48 | MRKVKF 53 |
| | 122 | 141 | IKRQKQ 146 |
| | 123 | 383 | ARRKRM 388 |
| | 124 | 393 | SRKKRE 398 |
| | 125 | 490 | KKKLKI 495 |
| | 126 | 543 | ARRSRS 548 |
| | 127 | 550 | TRKRKR 555 |
| | 128 | 586 | VKKAKT 591 |
| | 129 | 629 | GKKDRR 634 |
| EVG1 | 130 | 17 | RRRPKT 22 |
| | 131 | 138 | ERKRKA 143 |
| | 132 | 17 | RRRPKT 22 |
| | 133 | 138 | ERKRKA 143 |
| ASPL | 134 | 282 | PKKSKS 287 |
| | 135 | 282 | PKKSKS 287 |
| Zinc transporter 1 | 136 | 477 | EKKPRR 482 |
| | 137 | 477 | EKKPRR 482 |
| Uveal autoantigen | 138 | 603 | EKKGRK 608 |
| | 139 | 995 | ERKFKA 1000 |
| | 140 | 1023 | VKKNKQ 1028 |
| | 141 | 603 | EKKGRK 608 |
| | 142 | 995 | ERKFKA 1000 |
| | 143 | 1023 | VKKNKQ 1028 |
| RAB39 | 144 | 7 | VRRDRV 12 |
| | 145 | 7 | VRRDRV 12 |
| Down syndrome cell adhesion molecule | 146 | 320 | PRKVKS 325 |
| | 147 | 387 | VRKDKL 392 |
| | 148 | 320 | PRKVKS 325 |
| | 149 | 387 | VRKDKL 392 |
| Protein-tyrosine phosphatase, non-receptor type 12 | 150 | 139 | GRKKCERY 146 |
| | 151 | 59 | VKKNRY 64 |
| | 152 | 59 | VKKNRY 64 |

TABLE 3-continued

| | SEQ ID NO: | | |
|---|---|---|---|
| WD-repeat protein 11 | 153 | 752 | VRKIRF 757 |
| | 154 | 752 | VRKIRF 757 |
| Gastric cancer-related protein VRG107 | 155 | 20 | SRKRQTRR 27 |
| | 156 | 25 | TRRRRN 30 |
| | 157 | 25 | TRRRRN 30 |
| Early growth response protein 4 | 158 | 356 | ARRKGRRG 363 |
| | 159 | 452 | EKKRHSKV 459 |
| | 160 | 357 | RRKGRR 362 |
| | 161 | 357 | RRKGRR 362 |
| Vesicle transport-related protein | 162 | 309 | PKRKNKKS 316 |
| | 163 | 226 | DKKLRE 231 |
| | 164 | 310 | KRKNKK 315 |
| | 165 | 355 | VKRLKS 360 |
| | 166 | 226 | DKKLRE 231 |
| | 167 | 310 | KRKNKK 315 |
| | 168 | 355 | VKRLKS 360 |
| UPF3X | 169 | 140 | AKKKTKKR 147 |
| | 170 | 141 | KKKTKK 146 |
| | 171 | 217 | ERRRRE 222 |
| | 172 | 225 | RKRQRE 230 |
| | 173 | 233 | RRKWKE 238 |
| | 174 | 240 | EKRKRK 245 |
| | 175 | 296 | DKREKA 301 |
| | 176 | 373 | RRRQKE 378 |
| | 177 | 393 | MKKEKD 398 |
| | 178 | 426 | VKRDRI 431 |
| | 179 | 140 | AKKKTKKRD 148 |
| | 180 | 141 | KKKTKK 146 |
| | 181 | 217 | ERRRRE 222 |
| | 182 | 225 | RKRQRE 230 |
| | 183 | 233 | RRKWKE 238 |
| | 184 | 240 | EKRKRK 245 |
| | 185 | 296 | DKREKA 301 |
| | 186 | 373 | RRRQKE 378 |
| | 187 | 393 | MKKEKD 398 |
| | 188 | 426 | VKRDRI 431 |
| CGI-201 protein, type IV | 189 | 49 | ARRTRS 54 |
| | 190 | 49 | ARRTRS 54 |
| RING finger protein 23 | 191 | 98 | KRKIRD 103 |
| | 192 | 98 | KRKIRD 103 |
| FKSG17 | 193 | 72 | EKKARK 77 |
| | 194 | 95 | IRKSKN 100 |
| | 195 | 72 | EKKARK 77 |
| | 196 | 95 | IRKSKN 100 |
| P83 | 197 | 681 | ARKERE 686 |
| | 198 | 681 | ARKERE 686 |
| Ovarian cancer-related protein 1 | 199 | 62 | LKRDRF 67 |
| | 200 | 62 | LKRDRF 67 |
| MHC class II transactivator CIITA | 201 | 407 | HRRPRE 412 |
| | 202 | 741 | PRKKRP 746 |
| | 203 | 783 | DRKQKV 788 |
| | 204 | 407 | HRRPRE 412 |
| | 205 | 741 | PRKKRP 746 |
| | 206 | 783 | DRKQKV 788 |
| Platelet glycoprotein VI-2 | 207 | 275 | SRRKRLRH 282 |
| | 208 | 275 | SRRKRL 280 |
| | 209 | 275 | SRRKRL 280 |
| Ubiquitin-like 5 protein | 210 | 11 | GKKVRV 16 |
| | 211 | 11 | GKKVRV 16 |
| Protein kinase D2 | 212 | 191 | ARKRRL 196 |
| | 213 | 191 | ARKRRL 196 |
| Homeobox protein GSH-2 | 214 | 202 | GKRMRT 207 |
| | 215 | 252 | NRRVKH 257 |
| | 216 | 202 | GKRMRT 207 |
| | 217 | 252 | NRRVKH 257 |
| ULBP3 protein | 218 | 166 | ARRMKE 171 |
| | 219 | 201 | HRKKRL 206 |
| | 220 | 166 | ARRMKE 171 |
| | 221 | 201 | HRKKRL 206 |
| Type II iodothyronine deiodinase | 222 | 87 | SKKEKV 92 |
| | 223 | 87 | SKKEKV 92 |
| | 224 | 299 | SKRCKK 304 |
| | 225 | 299 | SKRCKK 304 |
| Sperm antigen | 226 | 160 | LKKYKE 165 |
| | 227 | 478 | IKRLKE 483 |
| | 228 | 160 | LKKYKEKRT 168 |
| | 229 | 160 | LKKYKE 165 |
| | 230 | 478 | IKRLKE 483 |
| UDP-GalNAc: polypeptide N-acetylgalactosaminyl-transferase | 231 | 4 | ARKIRT 9 |
| | 232 | 44 | DRRVRS 49 |
| | 233 | 138 | PRKCRQ 143 |
| | 234 | 4 | ARKIRT 9 |
| | 235 | 44 | DRRVRS 49 |
| | 236 | 138 | PRKCRQ 143 |
| NCBE | 237 | 62 | HRRHRH 67 |
| | 238 | 73 | RKRDRE 78 |
| | 239 | 1012 | SKKKKL 1017 |
| | 240 | 62 | HRRHRH 67 |
| | 241 | 73 | RKRDRE 78 |
| | 242 | 1012 | SKKKKL 1017 |
| WD repeat protein | 243 | 372 | LKKKEERL 379 |
| | 244 | 384 | EKKQRR 389 |
| | 245 | 400 | AKKMRP 405 |
| | 246 | 384 | EKKQRR 389 |
| | 247 | 400 | AKKMRP 405 |
| Phosphodiesterase 11A | 248 | 27 | MRKGKQ 32 |
| | 249 | 27 | MRKGKQ 32 |
| Probable cation-transporting ATPase 2 | 250 | 891 | ERRRRPRD 898 |
| | 251 | 306 | SRKWRP 311 |
| | 252 | 891 | ERRRRP 896 |
| | 253 | 306 | SRKWRP 311 |
| | 254 | 891 | ERRRRP 896 |
| HMG-box transcription factor TCF-3 | 255 | 420 | GKKKKRKR 427 |
| | 256 | 399 | ARKERQ 404 |
| | 257 | 420 | GKKKKR 425 |
| | 258 | 420 | GKKKKRKRE 428 |
| | 259 | 399 | ARKERQ 404 |
| | 260 | 420 | GKKKKR 425 |
| HVPS11 | 261 | 793 | VRRYRE 798 |
| | 262 | 793 | VRRYRE 798 |
| PIST | 263 | 165 | NKKEKM 170 |
| | 264 | 165 | NKKEKM 170 |
| FYN-binding protein | 265 | 473 | KKREKE 478 |
| | 266 | 501 | KKKFKL 506 |
| | 267 | 682 | LKKLKK 687 |
| | 268 | 696 | RKKFKY 701 |
| | 269 | 473 | KKREKE 478 |
| | 270 | 501 | KKKFKL 506 |
| | 271 | 682 | LKKLKK 687 |
| | 272 | 696 | RKKFKY 701 |
| C1orf25 | 273 | 620 | GKKQKT 625 |
| | 274 | 620 | GKKQKT 625 |

TABLE 3-continued

| | SEQ ID NO: | | |
|---|---|---|---|
| C1orf14 | 275 | 441 LRRRKGKR | 448 |
| | 276 | 70 LRRWRR | 75 |
| | 277 | 441 LRRRKG | 446 |
| | 278 | 70 LRRWRR | 75 |
| | 279 | 441 LRRRKG | 446 |
| T-box transcription factor TBX3 | 280 | 144 DKKAKY | 149 |
| | 281 | 309 GRREKR | 314 |
| | 282 | 144 DKKAKY | 149 |
| | 283 | 309 GRREKR | 314 |
| Mitochondrial 39S ribosomal protein L47 | 284 | 121 AKRQRL | 126 |
| | 285 | 216 EKRARI | 221 |
| | 286 | 230 RKKAKI | 235 |
| | 287 | 121 AKRQRL | 126 |
| | 288 | 216 EKRARI | 221 |
| | 289 | 230 RKKAKI | 235 |
| CGI-203 | 290 | 33 VRRIRD | 38 |
| | 291 | 33 VRRIRD | 38 |
| Jagged1 | 292 | 1093 LRKRRK | 1098 |
| | 293 | 1093 LRKRRK | 1098 |
| Secretory carrier-associated membrane protein 1 | 294 | 102 DRRERE | 107 |
| | 295 | 102 DRRERE | 107 |
| Vitamin D receptor-interacting protein complex component DRIP205 | 296 | 673 KKKKSSRL | 680 |
| | 297 | 672 TKKKKS | 677 |
| | 298 | 954 QKRVKE | 959 |
| | 299 | 978 GKRSRT | 983 |
| | 300 | 995 PKRKKA | 1000 |
| | 301 | 1338 GKREKS | 1343 |
| | 302 | 1482 HKKHKK | 1487 |
| | 303 | 1489 KKKVKD | 1494 |
| | 304 | 672 TKKKKS | 677 |
| | 305 | 954 QKRVKE | 959 |
| | 306 | 978 GKRSRT | 983 |
| | 307 | 995 PKRKKA | 1000 |
| | 308 | 1338 GKREKS | 1343 |
| | 309 | 1482 HKKHKK | 1487 |
| | 310 | 1489 KKKVKD | 1494 |
| Secretory carrier-associated membrane protein 2 | 311 | 100 ERKERE | 105 |
| | 312 | 100 ERKERE | 105 |
| Nogo receptor | 313 | 420 SRKNRT | 425 |
| | 314 | 420 SRKNRT | 425 |
| FLAMINGO 1 | 315 | 169 GRRKRN | 174 |
| | 316 | 2231 ARRQRR | 2236 |
| | 317 | 169 GRRKRN | 174 |
| | 318 | 2231 ARRQRR | 2236 |
| CC-chemokine receptor | 319 | 58 CKRLKS | 63 |
| | 320 | 58 CKRLKS | 63 |
| Prolactin regulatory element-binding protein | 321 | 271 HKRLRQ | 276 |
| | 322 | 271 HKRLRQ | 276 |
| Kappa B and V(D)J recombination signal sequences binding protein | 323 | 17 PRKRLTKG | 24 |
| | 324 | 713 RKRRKEKS | 720 |
| | 325 | 903 PKKKRLRL | 910 |
| | 326 | 180 HKKERK | 185 |
| | 327 | 629 TKKTKK | 634 |
| | 328 | 712 LRKRRK | 717 |
| | 329 | 903 PKKKRL | 908 |
| | 330 | 1447 QKRVKE | 1452 |
| | 331 | 1680 SRKPRM | 1685 |
| | 332 | 180 HKKERK | 185 |
| | 333 | 629 TKKTKK | 634 |
| | 334 | 712 LRKRRK | 717 |
| | 335 | 903 PKKKRL | 908 |
| | 336 | 1447 QKRVKE | 1452 |
| | 337 | 1680 SRKPRM | 1685 |
| Breast cancer metastasis-suppressor 1 | 338 | 200 SKRKKA | 205 |
| | 339 | 229 IKKARA | 234 |
| | 340 | 200 SKRKKA | 205 |
| | 341 | 229 IKKARA | 234 |
| Forkhead box protein P3 | 342 | 414 RKKRSQRP | 421 |
| | 343 | 413 FRKKRS | 418 |
| | 344 | 413 FRKKRS | 418 |
| FAS BINDING PROTEIN | 345 | 228 LKRKLIRL | 235 |
| | 346 | 391 RKKRRARL | 398 |
| | 347 | 358 ARRLRE | 363 |
| | 348 | 390 ERKKRR | 395 |
| | 349 | 629 CKKSRK | 634 |
| | 350 | 358 ARRLRE | 363 |
| | 351 | 390 ERKKRR | 395 |
| | 352 | 629 CKKSRK | 634 |
| Ubiquitin carboxyl-terminal hydrolase 12 | 353 | 228 HKRMKV | 233 |
| | 354 | 244 LKRFKY | 249 |
| | 355 | 228 HKRMKV | 233 |
| | 356 | 244 LKRFKY | 249 |
| KIAA0472 protein | 357 | 110 HRKPKL | 115 |
| | 358 | 110 HRKPKL | 115 |
| PNAS-101 | 359 | 68 LKRSRP | 73 |
| | 360 | 106 PRKSRR | 111 |
| | 361 | 68 LKRSRP | 73 |
| | 362 | 106 PRKSRR | 111 |
| PNAS-26 | 363 | 118 DRRTRL | 123 |
| | 364 | 118 DRRTRL | 123 |
| Myslin transcription factor 2 sodium/potassium-transporting ATPase gamma chain | 365 | 176 GRRKSERQ | 183 |
| | 366 | 47 SRRFRC | 52 |
| | 367 | 55 NKKRRQ | 60 |
| | 368 | 47 SRRFRC | 52 |
| | 369 | 55 NKKRRQ | 60 |
| Mdm4 protein | 370 | 441 EKRPRD | 446 |
| | 371 | 464 ARRLKK | 469 |
| | 372 | 441 EKRPRD | 446 |
| | 373 | 464 ARRLKK | 469 |
| G antigen family D 2 protein | 374 | 87 QKKIRI | 92 |
| | 375 | 87 QKKIRI | 92 |
| NipSnap2 protein | 376 | 153 FRKARS | 158 |
| | 377 | 153 FRKARS | 158 |
| Stannin | 378 | 73 ERKAKL | 78 |
| | 379 | 73 ERKAKL | 78 |
| Sodium bicarbonate cotransporter | 380 | 973 EKKKKKKK | 980 |
| | 381 | 165 LRKHRH | 170 |
| | 382 | 666 LKKFKT | 671 |
| | 383 | 966 DKKKKE | 971 |
| | 384 | 973 EKKKKK | 978 |
| | 385 | 165 LRKHRH | 170 |
| | 386 | 666 LKKFKT | 671 |
| | 387 | 966 DKKKKE | 971 |
| | 388 | 973 EKKKKK | 978 |
| Myosin X | 389 | 683 YKRYKV | 688 |
| | 390 | 828 EKKKRE | 833 |
| | 391 | 1653 LKRIRE | 1658 |
| | 392 | 1676 LKKTKC | 1681 |
| | 393 | 683 YKRYKV | 688 |

TABLE 3-continued

| | SEQ ID NO: | | |
|---|---|---|---|
| | 394 | 828 EKKKRE | 833 |
| | 395 | 1653 LKRIRE | 1658 |
| | 396 | 1676 LKKTKC | 1681 |
| PNAS-20 | 397 | 21 RKRKSVRG | 28 |
| | 398 | 20 ERKRKS | 25 |
| | 399 | 20 ERKRKS | 25 |
| Pellino | 400 | 36 RRKSRF | 41 |
| | 401 | 44 FKRPKA | 49 |
| | 402 | 36 RRKSRF | 41 |
| | 403 | 44 FKRPKA | 49 |
| Hyaluronan mediated motility receptor | 404 | 66 ARKVKS | 71 |
| | 405 | 66 ARKVKS | 71 |
| Short transient receptor potential channel 7 | 406 | 753 FKKTRY | 758 |
| | 407 | 753 FKKTRY | 758 |
| Liprin-alpha2 | 408 | 825 PKKKGIKS | 832 |
| | 409 | 575 IRRPRR | 580 |
| | 410 | 748 LRKHRR | 753 |
| | 411 | 839 GKKEKA | 844 |
| | 412 | 875 DRRLKK | 880 |
| | 413 | 575 IRRPRR | 580 |
| | 414 | 748 LRKHRR | 753 |
| | 415 | 839 GKKEKA | 844 |
| | 416 | 875 DRRLKK | 880 |
| Transcription intermediary factor 1-alpha | 417 | 904 DKRKCERL | 911 |
| | 418 | 1035 PRKKRLKS | 1042 |
| | 419 | 321 NKKGKA | 326 |
| | 420 | 1035 PRKKRL | 1040 |
| | 421 | 321 NKKGKA | 326 |
| | 422 | 1035 PRKKRL | 1040 |
| CARTILAGE INTERMEDIATE LAYER PROTEIN | 423 | 719 QRRNKR | 724 |
| | 424 | 719 QRRNKR | 724 |
| UBX domain-containing protein 1 | 425 | 194 YRKIKL | 199 |
| | 426 | 194 YRKIKL | 199 |
| Arachidonate 12-lipoxygenase, 12R type | 427 | 166 VRRHRN | 171 |
| | 428 | 233 WKRLKD | 238 |
| | 429 | 166 VRRHRN | 171 |
| | 430 | 233 WKRLKD | 238 |
| Hematopoietic PBX-interacting protein | 431 | 159 LRRRGRE | 166 |
| | 432 | 698 LKKRSGKK | 705 |
| | 433 | 159 LRRRG | 164 |
| | 434 | 703 GKKDKH | 708 |
| | 435 | 159 LRRRG | 164 |
| | 436 | 703 GKKDKH | 708 |
| NAG18 | 437 | 28 LKKKKK | 33 |
| | 438 | 28 LKKKKK | 33 |
| POU 5 domain protein | 439 | 222 ARKRKR | 227 |
| | 440 | 222 ARKRKR | 227 |
| NRCAM PROTEIN | 441 | 2 PKKKRL | 7 |
| | 442 | 887 SKRNRR | 892 |
| | 443 | 1185 IRRNKG | 1190 |
| | 444 | 1273 GKKEKE | 1278 |
| | 445 | 2 PKKKRL | 7 |
| | 446 | 887 SKRNRR | 892 |
| | 447 | 1185 IRRNKG | 1190 |
| | 448 | 1273 GKKEKE | 1278 |
| protocadherin gamma cluster | 449 | 11 TRRSRA | 16 |
| | 450 | 11 TRRSRA | 16 |
| SKD1 protein | 451 | 288 IRRRFEKR | 295 |
| | 452 | 251 ARRIKT | 256 |
| | 453 | 362 FKKVRG | 367 |
| | 454 | 251 ARRIKT | 256 |
| | 455 | 362 FKKVRG | 367 |
| ANTI-DEATH PROTEIN | 456 | 58 HRKRSRRV | 65 |
| | 457 | 59 RKRSRR | 64 |
| | 458 | 59 RKRSRR | 64 |
| Centrin 3 | 459 | 14 TKRKKRRE | 21 |
| | 460 | 14 TKRKKR | 19 |
| | 461 | 14 TKRKKR | 19 |
| Ectonucleoside triphosphate diphosphohydrolase 3 | 462 | 512 TRRKRH | 517 |
| | 463 | 512 TRRKRH | 517 |
| Homeobox protein prophet of PIT-1 | 464 | 12 PKKGRV | 17 |
| | 465 | 69 RRRHRT | 74 |
| | 466 | 119 NRRAKQ | 124 |
| | 467 | 12 PKKGRV | 17 |
| | 468 | 69 RRRHRT | 74 |
| | 469 | 119 NRRAKQ | 124 |
| PROSTAGLANDIN EP3 RECEPTOR | 470 | 77 YRRRESKR | 84 |
| | 471 | 389 MRKRRLRE | 396 |
| | 472 | 82 SKRKKS | 87 |
| | 473 | 389 MRKRRL | 394 |
| | 474 | 82 SKRKKS | 87 |
| | 475 | 389 MRKRRL | 394 |
| Pituitary homeobox 3 | 476 | 58 LKKKQRRQ | 65 |
| | 477 | 59 KKKQRR | 64 |
| | 478 | 112 NRRAKW | 117 |
| | 479 | 118 RKRERS | 123 |
| | 480 | 59 KKKQRR | 64 |
| | 481 | 112 NRRAKW | 117 |
| | 482 | 118 RKRERS | 123 |
| HPRL-3 | 483 | 136 KRRGRI | 141 |
| | 484 | 136 KRRGRI | 141 |
| Advillin | 485 | 812 MKKEKG | 817 |
| | 486 | 812 MKKEKG | 817 |
| Nuclear LIM interactor-interacting factor 1 | 487 | 32 GRRARP | 37 |
| | 488 | 109 LKKQRS | 114 |
| | 489 | 32 GRRARP | 37 |
| | 490 | 109 LKKQRS | 114 |
| Core histone macro-H2A.1 | 491 | 5 GKKKSTKT | 12 |
| | 492 | 114 AKKRGSKG | 121 |
| | 493 | 70 NKKGRV | 75 |
| | 494 | 132 AKKAKS | 137 |
| | 495 | 154 ARKSKK | 159 |
| | 496 | 302 DKKLKS | 307 |
| | 497 | 70 NKKGRV | 75 |
| | 498 | 132 AKKAKS | 137 |
| | 499 | 154 ARKSKK | 159 |
| | 500 | 302 DKKLKS | 307 |
| Villin-like protein | 501 | 180 KRRRNQKL | 187 |
| | 502 | 179 EKRRRN | 184 |
| | 503 | 179 EKRRRN | 184 |
| BETA-FILAMIN | 504 | 254 PKKARA | 259 |
| | 505 | 2002 ARRAKV | 2007 |
| | 506 | 254 PKKARA | 259 |
| | 507 | 2002 ARRAKV | 2007 |
| Tripartite motif protein TRIM31 alpha | 508 | 290 LKKFKD | 295 |
| | 509 | 290 LKKFKD | 295 |
| Nuclear receptor co-repressor 1 | 510 | 106 SKRPRL | 111 |
| | 511 | 299 ARKQRE | 304 |
| | 512 | 330 RRKAKE | 335 |
| | 513 | 349 IRKQRE | 354 |
| | 514 | 412 QRRVKF | 417 |

TABLE 3-continued

| | SEQ ID NO: | | |
|---|---|---|---|
| | 515 | 497 | KRRGRN 502 |
| | 516 | 580 | RRKGRI 585 |
| | 517 | 687 | SRKPRE 692 |
| | 518 | 2332 | SRKSKS 2337 |
| | 519 | 106 | SKRPRL 111 |
| | 520 | 299 | ARKQRE 304 |
| | 521 | 330 | RRKAKE 335 |
| | 522 | 349 | IRKQRE 354 |
| | 523 | 412 | QRRVKF 417 |
| | 524 | 497 | KRRGRN 502 |
| | 525 | 580 | RRKGRI 585 |
| | 526 | 687 | SRKPRE 692 |
| | 527 | 2332 | SRKSKS 2337 |
| BRAIN EXPRESSED RING FINGER PROTEIN | 528 | 432 | KRRVKS 437 |
| | 529 | 432 | KRRVKS 437 |
| PB39 | 530 | 231 | TKKIKL 236 |
| | 531 | 231 | TKKIKL 236 |
| Sperm acrosomal protein | 532 | 48 | FRKRMEKE 55 |
| | 533 | 24 | RRKARE 29 |
| | 534 | 135 | KRKLKE 140 |
| | 535 | 213 | KKRLRQ 218 |
| | 536 | 24 | RRKARE 29 |
| | 537 | 135 | KRKLKE 140 |
| | 538 | 213 | KKRLRQ 218 |
| VESICLE TRAFFICKING PROTEIN SEC22B | 539 | 177 | SKKYRQ 182 |
| | 540 | 177 | SKKYRQ 182 |
| Nucleolar transcription factor 1 | 541 | 79 | VRKFRT 84 |
| | 542 | 102 | GKKLKK 107 |
| | 543 | 125 | EKRAKY 130 |
| | 544 | 147 | SKKYKE 152 |
| | 545 | 156 | KKKMKY 161 |
| | 546 | 240 | KKRLKW 245 |
| | 547 | 451 | KKKAKY 456 |
| | 548 | 523 | EKKEKL 528 |
| | 549 | 558 | SKKMKF 563 |
| | 550 | 79 | VRKFRT 84 |
| | 551 | 102 | GKKLKK 107 |
| | 552 | 125 | EKRAKY 130 |
| | 553 | 147 | SKKYKE 152 |
| | 554 | 156 | KKKMKY 161 |
| | 555 | 240 | KKRLKW 245 |
| | 556 | 451 | KKKAKY 456 |
| | 557 | 523 | EKKEKL 528 |
| | 558 | 558 | SKKMKF 563 |
| Plexin-B3 | 559 | 248 | FRRRGARA 255 |
| Junctophilin type3 | 560 | 626 | QKRRYSKG 633 |
| Plaucible mixed-lineage kinase protein | 561 | 773 | YRKKPHRP 780 |
| | 562 | 312 | ERRLKM 317 |
| | 563 | 312 | ERRLKM 317 |
| fatty acid binding protein 4, adipocyte | 564 | 78 | DRKVKS 83 |
| | 565 | 105 | IKRKRE 110 |
| | 566 | 78 | DRKVKS 83 |
| | 567 | 105 | IKRKRE 110 |
| exostoses (multiple) 1 | 568 | 78 | SKKGRK 83 |
| | 569 | 78 | SKKGRK 83 |
| DHHC-domain-containing cysteine-rich protein | 570 | 64 | HRRPRG 69 |
| | 571 | 64 | HRRPRG 69 |
| Myb proto-oncogene protein | 572 | 2 | ARRPRH 7 |
| | 573 | 292 | EKRIKE 297 |
| | 574 | 523 | LKKIKQ 528 |
| | 575 | 2 | ARRPRH 7 |
| | 576 | 292 | EKRIKE 297 |
| | 577 | 523 | LKKIKQ 528 |

TABLE 3-continued

| | SEQ ID NO: | | |
|---|---|---|---|
| Long-chain-fatty-acid--COA ligase 2 | 578 | 259 | RRKPKP 264 |
| | 579 | 259 | RRKPKP 264 |
| syntaxin1B2 | 580 | 260 | ARRKKI 265 |
| | 581 | 260 | ARRKKI 265 |
| Dachshund 2 | 582 | 162 | ARRKRQ 167 |
| | 583 | 516 | QKRLKK 521 |
| | 584 | 522 | EKKTKR 527 |
| | 585 | 162 | ARRKRQ 167 |
| | 586 | 516 | QKRLKK 521 |
| | 587 | 522 | EKKTKR 527 |
| DEAD/DEXH helicase DDX31 | 588 | 344 | EKRKSEKA 351 |
| | 589 | 760 | TRKKRK 765 |
| | 590 | 760 | TRKKRK 765 |
| Androgen receptor | 591 | 628 | ARKLKK 633 |
| | 592 | 628 | ARKLKK 633 |
| Retinoic acid receptor alpha | 593 | 364 | RKRRPSRP 371 |
| | 594 | 163 | NKKKKE 168 |
| | 595 | 363 | VRKRRP 368 |
| | 596 | 163 | NKKKKE 168 |
| | 597 | 363 | VRKRRP 368 |
| Kinesin heavy chain | 598 | 340 | WKKKYEKE 347 |
| | 599 | 605 | VKRCKQ 610 |
| | 600 | 864 | EKRLRA 869 |
| | 601 | 605 | VKRCKQ 610 |
| | 602 | 864 | EKRLRA 869 |
| DIUBIQUITIN | 603 | 30 | VKKIKE 35 |
| | 604 | 30 | VKKIKE 35 |
| BING1 PROTEIN | 605 | 519 | NKKFKM 524 |
| | 606 | 564 | ERRHRL 569 |
| | 607 | 519 | NKKFKM 524 |
| | 608 | 564 | ERRHRL 569 |
| Focal adhesion kinase 1 | 609 | 664 | SRRPRF 669 |
| | 610 | 664 | SRRPRF 669 |
| EBN2 PROTEIN | 611 | 20 | TKRKKPRR 27 |
| | 612 | 13 | PKKDKL 18 |
| | 613 | 20 | TKRKKP 25 |
| | 614 | 47 | NKKNRE 52 |
| | 615 | 64 | LKKSRI 69 |
| | 616 | 76 | PKKPRE 81 |
| | 617 | 493 | SRKQRQ 498 |
| | 618 | 566 | VKRKRK 571 |
| | 619 | 13 | PKKDKL 18 |
| | 620 | 20 | TKRKKP 25 |
| | 621 | 47 | NKKNRE 52 |
| | 622 | 64 | LKKSRI 69 |
| | 623 | 76 | PKKPRE 81 |
| | 624 | 493 | SRKQRQ 498 |
| | 625 | 566 | VKRKRK 571 |
| CO16 PROTEIN | 626 | 33 | ARRLRR 38 |
| | 627 | 115 | PRRCKW 120 |
| | 628 | 33 | ARRLRR 38 |
| | 629 | 115 | PRRCKW 120 |
| KYNURENINE 3-MONOOXYGENASE | 630 | 178 | MKKPRF 183 |
| | 631 | 178 | MKKPRF 183 |
| MLN 51 protein | 632 | 4 | RRRQRA 9 |
| | 633 | 255 | PRRIRK 260 |
| | 634 | 407 | ARRTRT 412 |
| | 635 | 4 | RRRQRA 9 |
| | 636 | 255 | PRRIRK 260 |
| | 637 | 407 | ARRTRT 412 |

TABLE 3-continued

| | SEQ ID NO: | | |
|---|---|---|---|
| MHC class II antigen | 638 | 99 QKRGRV | 104 |
| MHC class II antigen | 639 | 99 QKRGRV | 104 |
| Transforming acidic coiled-coil-containing protein 1 | 640 | 225 SRRSKL | 230 |
| | 641 | 455 PKKAKS | 460 |
| | 642 | 225 SRRSKL | 230 |
| | 643 | 455 PKKAKS | 460 |
| Neuro-endocrine specific protein VGF | 644 | 479 EKRNRK | 484 |
| | 645 | 479 EKRNRK | 484 |
| Organic cation transporter | 646 | 230 GRRYRR | 235 |
| | 647 | 535 PRKNKE | 540 |
| | 648 | 230 GRRYRR | 235 |
| | 649 | 535 PRKNKE | 540 |
| DNA polymerase theta | 650 | 215 KRRKHLKR | 222 |
| | 651 | 214 WKRRKH | 219 |
| | 652 | 220 LKRSRD | 225 |
| | 653 | 1340 GRKLRL | 1345 |
| | 654 | 1689 SRKRKL | 1694 |
| | 655 | 214 WKRRKH | 219 |
| | 656 | 220 LKRSRD | 225 |
| | 657 | 1340 GRKLRL | 1345 |
| | 658 | 1689 SRKRKL | 1694 |
| CDC45-related protein | 659 | 169 MRRRQRRE | 176 |
| | 660 | 155 EKRTRL | 160 |
| | 661 | 170 RRRQRR | 175 |
| | 662 | 483 NRRCKL | 488 |
| | 663 | 155 EKRTRL | 160 |
| | 664 | 170 RRRQRR | 175 |
| | 665 | 483 NRRCKL | 488 |
| Chloride intracellular channel protein 2 | 666 | 197 AKKYRD | 202 |
| | 667 | 197 AKKYRD | 202 |
| Methyl-CpG binding protein | 668 | 85 KRKKPSRP | 92 |
| | 669 | 83 SKKRKK | 88 |
| | 670 | 318 QKRQKC | 323 |
| | 671 | 354 YRRRKR | 359 |
| | 672 | 83 SKKRKK | 88 |
| | 673 | 318 QKRQKC | 323 |
| | 674 | 354 YRRRKR | 359 |
| Protein kinase C, eta type | 675 | 155 RKRQRA | 160 |
| | 676 | 155 RKRQRA | 160 |
| Heterogeneous nuclear ribonucleoprotein H | 677 | 71 LKKDRE | 76 |
| | 678 | 169 LKKHKE | 174 |
| | 679 | 71 LKKDRE | 76 |
| | 680 | 169 LKKHKE | 174 |
| ORF2 | 681 | 11 SRRTRW | 16 |
| | 682 | 155 ERRRKF | 160 |
| | 683 | 185 LRRCRA | 190 |
| | 684 | 530 SRSRS | 535 |
| | 685 | 537 GRRRKS | 542 |
| | 686 | 742 ERRAKQ | 747 |
| | 687 | 11 SRRTRW | 16 |
| | 688 | 155 ERRRKF | 160 |
| | 689 | 185 LRRCRA | 190 |
| | 690 | 530 SRSRS | 535 |
| | 691 | 537 GRRRKS | 542 |
| | 692 | 742 ERRAKQ | 747 |
| F-box only protein 24 | 693 | 9 LRRRVKR | 16 |
| | 694 | 9 LRRRV | 14 |
| | 695 | 29 EKRGKG | 34 |
| | 696 | 9 LRRRV | 14 |
| | 697 | 29 EKRGKG | 34 |
| Leucin rich neuronal protein | 698 | 51 NRRLKH | 56 |
| | 699 | 51 NRRLKH | 56 |

TABLE 3-continued

| | SEQ ID NO: | | |
|---|---|---|---|
| RER1 protein | 700 | 181 KRRYRG | 186 |
| | 701 | 181 KRRYRG | 186 |
| Nephrocystin | 702 | 3 ARRQRD | 8 |
| | 703 | 430 PKKPKT | 435 |
| | 704 | 557 NRRSRN | 562 |
| | 705 | 641 EKRDKE | 646 |
| | 706 | 3 ARRQRD | 8 |
| | 707 | 430 PKKPKT | 435 |
| | 708 | 557 NRRSRN | 562 |
| | 709 | 641 EKRDKE | 646 |
| Adenylate kinase isoenzyme 2, mitochondrial | 710 | 60 GKKLKA | 65 |
| | 711 | 116 KRKEKL | 121 |
| | 712 | 60 GKKLKA | 65 |
| | 713 | 116 KRKEKL | 121 |
| Chlordecone reductase | 714 | 245 AKKHKR | 250 |
| | 715 | 245 AKKHKR | 250 |
| Metaxin 2 | 716 | 166 KRKMKA | 171 |
| | 717 | 166 KRKMKA | 171 |
| Paired mesoderm homeobox protein 1 | 718 | 89 KKKRKQRR | 96 |
| | 719 | 88 EKKKRK | 93 |
| | 720 | 94 QRRNRT | 99 |
| | 721 | 144 NRRAKF | 149 |
| | 722 | 88 EKKKRK | 93 |
| | 723 | 94 QRRNRT | 99 |
| | 724 | 144 NRRAKF | 149 |
| Ring finger protein | 725 | 174 LKRKWIRC | 181 |
| | 726 | 8 TRKIKL | 13 |
| | 727 | 95 MRKQRE | 100 |
| | 728 | 8 TRKIKL | 13 |
| | 729 | 95 MRKQRE | 100 |
| Ataxin 7 | 730 | 55 PRRTRP | 60 |
| | 731 | 377 GRRKRF | 382 |
| | 732 | 704 GKKRKN | 709 |
| | 733 | 834 GKKRKC | 839 |
| | 734 | 55 PRRTRP | 60 |
| | 735 | 377 GRRKRF | 382 |
| | 736 | 704 GKKRKN | 709 |
| | 737 | 834 GKKRKC | 839 |
| Growth-arrest-specific protein 1 SKAP55 protein | 738 | 169 ARRCDRD | 176 |
| | 739 | 115 EKKSKD | 120 |
| | 740 | 115 EKKSKD | 120 |
| Serine palmitoyltransferase 1 | 741 | 232 PRKARV | 237 |
| | 742 | 232 PRKARV | 237 |
| Serine palmitoyltransferase 2 | 743 | 334 KKKYKA | 339 |
| | 744 | 450 RRRLKE | 455 |
| | 745 | 334 KKKYKA | 339 |
| | 746 | 450 RRRLKE | 455 |
| Synaptopodin | 747 | 405 KRRQRD | 410 |
| | 748 | 405 KRRQRD | 410 |
| Alpha-tectorin | 749 | 1446 TRRCRC | 1451 |
| | 750 | 2080 IRRKRL | 2085 |
| | 751 | 1446 TRRCRC | 1451 |
| | 752 | 2080 IRRKRL | 2085 |
| LONG FORM TRANSCRIPTION FACTOR C-MAF | 753 | 291 QKRRTLKN | 298 |
| Usher syndrome type IIa protein | 754 | 1285 MRRLRS | 1290 |
| | 755 | 1285 MRRLRS | 1290 |
| MSin3A associated polypeptide p30 | 756 | 95 QKKVKI | 100 |
| | 757 | 124 NRRKRK | 129 |

TABLE 3-continued

| | SEQ ID NO: | | |
|---|---|---|---|
| | 758 | 158 | LRRYKR 163 |
| | 759 | 95 | QKKVKI 100 |
| | 760 | 124 | NRRKRK 129 |
| | 761 | 158 | LRRYKR 163 |
| Ig delta chain C region | 762 | 142 | KKKEKE 147 |
| | 763 | 142 | KKKEKE 147 |
| THYROID HORMONE RECEPTOR-ASSOCIATED PROTEIN COMPLEX COMPONENT TRAP100 | 764 | 383 | AKRKADRE 390 |
| | 765 | 833 | KKRHRE 838 |
| | 766 | 833 | KKRHRE 838 |
| P60 katanin | 767 | 369 | LRRRLEKR 376 |
| | 768 | 326 | SRRVKA 331 |
| | 769 | 326 | SRRVKA 331 |
| Transcription factor jun-D | 770 | 286 | RKRKLERI 293 |
| | 771 | 273 | RKRLRN 278 |
| | 772 | 285 | CRKRKL 290 |
| | 773 | 273 | RKRLRN 278 |
| | 774 | 285 | CRKRKL 290 |
| Sterol/retinol dehydrogenase | 775 | 152 | VRKARG 157 |
| | 776 | 152 | VRKARG 157 |
| Glycogen [starch] synthase, liver | 777 | 554 | DRRFRS 559 |
| | 778 | 578 | SRRQRI 583 |
| | 779 | 554 | DRRFRS 559 |
| | 780 | 578 | SRRQRI 583 |
| Estrogen-related receptor gamma | 781 | 173 | TKRRRK 178 |
| | 782 | 353 | VKKYKS 358 |
| | 783 | 173 | TKRRRK 178 |
| | 784 | 353 | VKKYKS 358 |
| Neural retina-specific leucine zipper protein | 785 | 162 | QRRTLKN 169 |
| Cytosolic phospholipase A2-gamma | 786 | 514 | NKKKILRE 521 |
| | 787 | 31 | LKKLRI 36 |
| | 788 | 218 | FKKGRL 223 |
| | 789 | 428 | CRRHKI 433 |
| | 790 | 31 | LKKLRI 36 |
| Cytosolic phospholipase A2-gamma | 791 | 218 | FKKGRL 223 |
| | 792 | 428 | CRRHKI 433 |
| GLE1 | 793 | 415 | AKKIKM 420 |
| | 794 | 415 | AKKIKM 420 |
| Multiple exostoses type II protein EXT2.I | 795 | 296 | VRKRCHKH 303 |
| | 796 | 659 | RKKFKC 664 |
| | 797 | 659 | RKKFKC 664 |
| Cyclic-AMP-dependent transcription factor ATF-7 | 798 | 86 | EKKARS 91 |
| | 799 | 332 | GRRRRT 337 |
| | 800 | 344 | ERRQRF 349 |
| | 801 | 86 | EKKARS 91 |
| | 802 | 332 | GRRRRT 337 |
| | 803 | 344 | ERRQRF 349 |
| Protein kinase/endoribonuclease | 804 | 886 | LRKFRT 891 |
| | 805 | 886 | LRKFRT 891 |
| Transcription factor E2F6 | 806 | 23 | RRRCRD 28 |
| | 807 | 59 | VKRPRF 64 |
| | 808 | 98 | VRKRRV 103 |
| | 809 | 117 | EKKSKN 122 |
| | 810 | 23 | RRRCRD 28 |
| | 811 | 59 | VKRPRF 64 |
| | 812 | 98 | VRKRRV 103 |
| | 813 | 117 | EKKSKN 122 |

TABLE 3-continued

| | SEQ ID NO: | | |
|---|---|---|---|
| MAP kinase-activating death domain protein | 814 | 1333 | IRKKVRRL 1340 |
| | 815 | 160 | KRRAKA 165 |
| | 816 | 943 | MKKVRR 948 |
| | 817 | 1034 | DKRKRS 1039 |
| | 818 | 1334 | RKKVRR 1339 |
| | 819 | 1453 | TKKCRE 1458 |
| | 820 | 160 | KRRAKA 165 |
| | 821 | 943 | MKKVRR 948 |
| | 822 | 1034 | DKRKRS 1039 |
| | 823 | 1334 | RKKVRR 1339 |
| | 824 | 1453 | TKKCRE 1458 |
| Orphan nuclear receptor PXR | 825 | 126 | KRKKSERT 133 |
| | 826 | 87 | TRKTRR 92 |
| | 827 | 125 | IKRKKS 130 |
| | 828 | 87 | TRKTRR 92 |
| | 829 | 125 | IKRKKS 130 |
| LENS EPITHELIUM-DERIVED GROWTH FACTOR | 830 | 149 | RKRKAEKQ 156 |
| | 831 | 286 | KKRKGGRN 293 |
| | 832 | 145 | ARRGRK 150 |
| | 833 | 178 | PKRGRP 183 |
| | 834 | 285 | EKKRKG 290 |
| | 835 | 313 | DRRKQ 318 |
| | 836 | 400 | LKKIRR 405 |
| | 837 | 337 | VKKVEKKRE 345 |
| | 838 | 145 | ARRGRK 150 |
| | 839 | 178 | PKRGRP 183 |
| | 840 | 285 | EKKRKG 290 |
| | 841 | 313 | DRRKQ 318 |
| | 842 | 400 | LKKIRR 405 |
| LIM homeobox protein co-factor | 843 | 255 | TKRRRKN 262 |
| | 844 | 255 | TKRRRK 260 |
| | 845 | 255 | TRRRKR 260 |
| MULTIPLE MEMBRANE SPANNING RECEPTOR TRC8 | 846 | 229 | WKRIRF 234 |
| | 847 | 229 | WKRIRF 234 |
| Transcription factor SUPT3H | 848 | 172 | DKKLRRL 179 |
| | 849 | 169 | MRKDKK 174 |
| | 850 | 213 | NKRQKI 218 |
| | 851 | 169 | MRKDKK 174 |
| | 852 | 213 | NKRQKI 218 |
| GEMININ | 853 | 50 | KRKHRN 55 |
| | 854 | 104 | EKRRKA 109 |
| | 855 | 50 | KRKHRN 55 |
| | 856 | 104 | EKRRKA 109 |
| Cell cycle-regulated factor p78 | 857 | 165 | EKKVSKA 172 |
| | 858 | 124 | IKRKKF 129 |
| | 859 | 188 | TKRVKK 193 |
| | 860 | 381 | DRRQKR 386 |
| | 861 | 124 | IKRKKF 129 |
| | 862 | 188 | TKRVKK 193 |
| | 863 | 381 | DRRQKR 386 |
| lymphocyte antigen 6 complex, locus D | 864 | 61 | QRKGRK 66 |
| | 865 | 85 | ARRLRA 90 |
| | 866 | 61 | QRKGRK 66 |
| | 867 | 85 | ARRLRA 90 |
| Delta 1-pyrroline-5-carboxylate synthetase | 868 | 455 | LRRTRI 460 |
| | 869 | 455 | LRRTRI 460 |
| B CELL LINKER PROTEIN BLNK | 870 | 36 | IKKLKV 41 |
| | 871 | 36 | IKKLKV 41 |
| B CELL LINKER PROTEIN BLNK-S | 872 | 36 | IKKLKV 41 |
| | 873 | 36 | IKKLKV 41 |
| fetal Alzheimer antigen | 874 | 5 | ARRRKKR 12 |
| | 875 | 16 | PRRRRRT 23 |

TABLE 3-continued

| | SEQ ID NO: | | |
|---|---|---|---|
| | 876 | 93 | WKKKTSRP 100 |
| | 877 | 5 | ARRRRK 10 |
| | 878 | 16 | PRRRRR 21 |
| | 879 | 26 | PRPRI 31 |
| | 880 | 35 | TRRMRW 40 |
| | 881 | 5 | ARRRRK 10 |
| | 882 | 16 | PRRRRR 21 |
| | 883 | 26 | PRPRI 31 |
| | 884 | 35 | TRRMRW 40 |
| Transient receptor potential channel 4 zeta splice variant | 885 | 505 | CKKKMRRK 512 |
| | 886 | 506 | KKKMRR 511 |
| | 887 | 676 | HRRSKQ 681 |
| | 888 | 506 | KKKMRR 511 |
| | 889 | 676 | HRRSKQ 681 |
| Myofibrillogenesis regulator MR-2 | 890 | 65 | RKRGKN 70 |
| | 891 | 65 | RKRGKN 70 |
| SH2 domain-containing phosphatase anchor protein 2c | 892 | 269 | IKKRSLRS 276 |
| immunoglobulin superfamily, member 3 | 893 | 394 | SKRPKN 399 |
| | 894 | 394 | SKRPKN 399 |
| Meis (mouse) homolog 3 | 895 | 112 | PRRSRR 117 |
| | 896 | 120 | WRRTRG 125 |
| | 897 | 112 | PRRSRR 117 |
| | 898 | 120 | WRRTRG 125 |
| Deleted in azoospermia 2 | 899 | 105 | GKKLKL 110 |
| | 900 | 114 | IRKQKL 119 |
| | 901 | 105 | GKKLKL 110 |
| | 902 | 114 | IRKQKL 119 |
| Centaurin gamma3 | 903 | 543 | NRKKHRRK 550 |
| | 904 | 544 | RKKHRR 549 |
| | 905 | 544 | RKKHRR 549 |
| Pre-B-cell leukemia transcription factor-1 | 906 | 233 | ARRKRR 238 |
| | 907 | 286 | NKRIRY 291 |
| | 908 | 233 | ARRKRR 238 |
| | 909 | 286 | NKRIRY 291 |
| 60S ribosomal protein L13a | 910 | 112 | DKKKRM 117 |
| | 911 | 158 | KRKEKA 163 |
| | 912 | 167 | YRKKQ 172 |
| | 913 | 112 | DKKKRM 117 |
| | 914 | 158 | KRKEKA 163 |
| | 915 | 167 | YRKKQ 172 |
| WD40- and FYVE-domain containing protein 3 | 916 | 388 | IKRLKI 393 |
| | 917 | 388 | IKRLKI 393 |
| LENG1 protein | 918 | 34 | RKRRGLRS 41 |
| | 919 | 84 | SRKKTRRM 91 |
| | 920 | 1 | MRRSRA 6 |
| | 921 | 33 | ERKRRG 38 |
| | 922 | 85 | RKKTRR 90 |
| | 923 | 1 | MRRSRA 6 |
| | 924 | 33 | ERKRRG 38 |
| | 925 | 85 | RKKTRR 90 |
| MRIP2 | 926 | 375 | NKKKHLKK 382 |
| G protein-coupled receptor | 927 | 430 | EKKKLKRH 437 |
| | 928 | 290 | WKKKRA 295 |
| | 929 | 395 | RKKAKF 400 |
| | 930 | 431 | KKKLKR 436 |
| | 931 | 290 | WKKKRA 295 |
| | 932 | 395 | RKKAKF 400 |
| | 933 | 431 | KKKLKR 436 |
| | 934 | 143 | LKKFRQ 148 |
| | 935 | 228 | LRKIRT 233 |
| | 936 | 143 | LKKFRQ 148 |
| | 937 | 228 | LRKIRT 233 |
| | 938 | 232 | QKRRHRA 239 |
| | 939 | 232 | QKRRH 237 |
| | 940 | 232 | QKRRH 237 |
| Sperm ion channel | 941 | 402 | QKRKTGRL 409 |
| A-kinase anchoring protein | 942 | 2232 | KRKKLVRD 2239 |
| | 943 | 2601 | EKRRRERE 2608 |
| | 944 | 2788 | EKKKKNKT 2795 |
| | 945 | 370 | RKKNKG 375 |
| | 946 | 1763 | SKKSKE 1768 |
| | 947 | 2200 | EKKVRL 2205 |
| | 948 | 2231 | LKRKKL 2236 |
| | 949 | 2601 | EKRRRE 2606 |
| | 950 | 2785 | EKKEKK 2790 |
| | 951 | 1992 | QKKDVVKRQ 2000 |
| | 952 | 370 | RKKNKG 375 |
| | 953 | 1763 | SKKSKE 1768 |
| | 954 | 2200 | EKKVRL 2205 |
| | 955 | 2231 | LKRKKL 2236 |
| | 956 | 2601 | EKRRRE 2606 |
| | 957 | 2785 | EKKEKK 2790 |
| Lymphocyte-specific protein LSP1 | 958 | 315 | GKRYKF 320 |
| | 959 | 315 | GKRYKF 320 |
| similar to signaling lymphocytic activation molecule (*H. sapiens*) | 960 | 261 | RRRGKT 266 |
| | 961 | 261 | RRRGKT 266 |
| Dermatan-4-sulfo-transferase-1 | 962 | 242 | VRRYRA 247 |
| | 963 | 242 | VRRYRA 247 |
| Moesin | 964 | 291 | MRRRKP 296 |
| | 965 | 325 | EKKKRE 330 |
| | 966 | 291 | MRRRKP 296 |
| | 967 | 325 | EKKKRE 330 |
| A-Raf proto-oncogene serine/threonine-protein kinase | 968 | 288 | KKKVKN 293 |
| | 969 | 358 | LRKTRH 363 |
| | 970 | 288 | KKKVKN 293 |
| | 971 | 358 | LRKTRH 363 |
| Cytochrome P450 2C18 | 972 | 117 | GKRWKE 122 |
| | 973 | 117 | GKRWKE 122 |
| | 974 | 117 | GKRWKE 122 |
| | 975 | 156 | LRKTKA 161 |
| | 976 | 117 | GKRWKE 122 |
| | 977 | 156 | LRKTKA 161 |
| Protein tyrosine phosphatase, non-receptor type 3 | 978 | 594 | IRRAVRS 601 |
| | 979 | 263 | FKRKKF 268 |
| | 980 | 388 | IRKPRH 393 |
| | 981 | 874 | VRKMRD 879 |
| | 982 | 263 | FKRKKF 268 |
| | 983 | 388 | IRKPRH 393 |
| | 984 | 874 | VRKMRD 879 |
| similar to kallikrein 7 (chymotryptic, stratum corneum) | 985 | 15 | VKKVRL 20 |
| | 986 | 15 | VKKVRL 20 |
| Hormone sensitive lipase | 987 | 703 | ARRLRN 708 |
| | 988 | 703 | ARRLRN 708 |
| 40S ribosomal protein S30 | 989 | 25 | KKKTGRA 32 |
| | 990 | 23 | EKKKKK 28 |
| | 991 | 23 | EKKKKK 28 |
| Zinc finger protein 91 | 992 | 617 | LRRHKR 622 |
| | 993 | 617 | LRRHKR 622 |

TABLE 3-continued

| | SEQ ID NO: | | |
|---|---|---|---|
| NNP-1 protein | 994 | 320 | NRKRLYKV 327 |
| | 995 | 387 | ERKRSRRR 394 |
| | 996 | 432 | QRRRTPRP 439 |
| | 997 | 454 | EKKKKRRE 461 |
| | 998 | 29 | VRKLRK 34 |
| | 999 | 355 | GRRQKK 360 |
| | 1000 | 361 | TKKQKR 366 |
| | 1001 | 388 | RKRSRR 393 |
| | 1002 | 454 | EKKKK 459 |
| | 1003 | 29 | VRKLRK 34 |
| | 1004 | 355 | GRRQKK 360 |
| | 1005 | 361 | TKKQKR 366 |
| | 1006 | 388 | RKRSRR 393 |
| | 1007 | 454 | EKKKK 459 |
| Methionyl-tRNA synthetase | 1008 | 725 | WKRIKG 730 |
| | 1009 | 725 | WKRIKG 730 |
| ELMO2 | 1010 | 560 | NRRRQERF 567 |
| Meningioma-expressed antigen 6/11 | 1011 | 432 | RKRAKD 437 |
| | 1012 | 432 | RKRAKD 437 |
| Inositol polyphosphate 4-phosphatase type I-beta | 1013 | 375 | LRKKLHKF 382 |
| | 1014 | 829 | ARKNKN 834 |
| | 1015 | 829 | ARKNKN 834 |
| | 1016 | 815 | SKKRKN 820 |
| | 1017 | 815 | SKKRKN 820 |
| C7ORF12 | 1018 | 40 | SRRYRG 45 |
| | 1019 | 338 | HRKNKP 343 |
| | 1020 | 40 | SRRYRG 45 |
| | 1021 | 338 | HRKNKP 343 |
| Rap guanine nucleotide exchange factor | 1022 | 138 | SRRFRKI 145 |
| | 1023 | 1071 | QRKKRWRS 1078 |
| | 1024 | 1099 | HKKRARRS 1106 |
| | 1025 | 139 | RRRFRK 144 |
| | 1026 | 661 | SKKVKA 666 |
| | 1027 | 930 | LKRMKI 935 |
| | 1028 | 1071 | QRKKRW 1076 |
| | 1029 | 1100 | KKRARR 1105 |
| | 1030 | 1121 | ARKVKQ 1126 |
| | 1031 | 139 | RRRFRK 144 |
| | 1032 | 661 | SKKVKA 666 |
| | 1033 | 930 | LKRMKI 935 |
| | 1034 | 1071 | QRKKRW 1076 |
| | 1035 | 1100 | KKRARR 1105 |
| | 1036 | 1121 | ARKVKQ 1126 |
| Sigma 1C adaptin | 1037 | 27 | ERKKITRE 34 |
| Alsin | 1038 | 883 | GRKRKE 888 |
| | 1039 | 883 | GRKRKE 888 |
| NOPAR2 | 1040 | 14 | LKRPRL 19 |
| | 1041 | 720 | VKREKP 725 |
| | 1042 | 14 | LKRPRL 19 |
| | 1043 | 720 | VKREKP 725 |
| AT-binding transcription factor 1 | 1044 | 294 | SKRPKT 299 |
| | 1045 | 961 | EKKNKL 966 |
| | 1046 | 1231 | NKRPRT 1236 |
| | 1047 | 1727 | DKRLRT 1732 |
| | 1048 | 2032 | QKRFRT 2037 |
| | 1049 | 2087 | EKKSKL 2092 |
| | 1050 | 2317 | QRKDKD 2322 |
| | 1051 | 2343 | PKKEKG 2348 |
| | 1052 | 294 | SKRPKT 299 |
| | 1053 | 961 | EKKNKL 966 |
| | 1054 | 1231 | NKRPRT 1236 |
| | 1055 | 1727 | DKRLRT 1732 |
| | 1056 | 2032 | QKRFRT 2037 |
| | 1057 | 2087 | EKKSKL 2092 |
| | 1058 | 2317 | QRKDKD 2322 |
| | 1059 | 2343 | PKKEKG 2348 |
| Suppressin | 1060 | 232 | YKRRKK 237 |
| | 1061 | 232 | YKRRKK 237 |
| Midline 1 protein | 1062 | 100 | TRRERA 105 |
| | 1063 | 494 | HRKLKV 499 |
| | 1064 | 100 | TRRERA 105 |
| | 1065 | 494 | HRKLKV 499 |
| High mobility group protein 2a | 1066 | 6 | PKKPKG 11 |
| | 1067 | 84 | GKKKKD 89 |
| | 1068 | 6 | PKKPKG 11 |
| | 1069 | 84 | GKKKKD 89 |

This application claims priority to A 1952/2003 filed on Dec. 4, 2003, the entirety of which is hereby incorporated by reference.

---

The invention claimed is:

1. A modified human Interleukin-8 (IL-8) protein, wherein the modified human Interleukin-8 has one or more amino acid substitutions in SEQ ID NO. 16, wherein the substitutions are selected from the group consisting of:
   (A) Arg, Lys or His substitution at position 70, and
   (B) Arg, Lys or His substitution at position 71.

2. The modified Interleukin-8 of claim 1, wherein the modified human Interleukin-8 has:
   A) Arg, Lys or His substitution at position 70, and
   (B) Arg, Lys or His substitution at position 71.

3. The modified Interleukin-8 of claim 1, wherein the modified human Interleukin-8 has one or more amino acid substitutions selected from the group consisting of:
   (C) Arg, Lys or His substitution at position 17, and
   (D) Arg, Lys or His substitution at position 21.

4. The modified Interleukin-8 of claim 2, wherein the modified human Interleukin-8 has one or more amino acid substitutions selected from the group consisting of:
   (C) Arg, Lys or His substitution at position 17, and
   (D) Arg, Lys or His substitution at position 21.

5. The modified Interleukin-8 of claim 1, wherein the modified human Interleukin-8 has:
   A) Arg, Lys or His substitution at position 17, and
   (B) Arg, Lys or His substitution at position 21.

6. The modified Interleukin-8 of claim 2, wherein the modified human Interleukin-8 has:
   A) Arg, Lys or His substitution at position 17, and
   (B) Arg, Lys or His substitution at position 21.

7. The modified Interleukin-8 of claim 1, wherein the modified human Interleukin-8 is further modified by deletion of amino acids at positions 1 through 6 of SEQ ID NO: 16.

8. The modified Interleukin-8 of claim 2, wherein the modified human Interleukin-8 is further modified by deletion of amino acids at positions 1 through 6 of SEQ ID NO: 16.

9. A modified human Interleukin-8 (IL-8) protein, wherein the modified
   human Interleukin-8 has:
   (I) one or more amino acid substitutions in SEQ ID NO: 16, wherein the substitutions are selected from the group consisting of:
      (A) Arg, Lys or His substitution at position 70,
      (B) Arg, Lys or His substitution at position 71
      (C) Arg, Lys or His substitution at position 17, and
      (D) Arg, Lys or His substitution at position 21; and
   (II) deletion of amino acids at positions 1 through 6 of SEQ ID NO. 16.

10. The modified human Interleukin-8 (IL-8) protein according to claim 9, wherein the modified human Interleukin-8 has:
    (A) Arg, Lys or His substitution at position 70, and
    (B) Arg, Lys or His substitution at position 71.

11. The modified human Interleukin-8 (IL-8) protein according to claim 9, wherein the modified human Interleukin-8 has:
    (A) Arg, Lys or His substitution at position 70,
    (B) Arg, Lys or His substitution at position 71, and
    (C) Arg, Lys or His substitution at position 17.

12. The modified human Interleukin-8 (IL-8) protein according to claim 9, wherein the modified human Interleukin-8 has:
    (A) Arg, Lys or His substitution at position 70,
    (B) Arg, Lys or His substitution at position 71, and
    (C) Arg, Lys or His substitution at position 21.

13. The modified human Interleukin-8 (IL-8) protein, wherein the modified human Interleukin-8 has:

(A) Arg, Lys or His substitution at position 70,
(B) Arg, Lys or His substitution at position 71
(C) Arg, Lys or His substitution at position 17, and
(D) Arg, Lys or His substitution at position 21.

14. The modified Interleukin-8 of claim 13, wherein the modified human Interleukin-8 is further modified by deletion of amino acids at positions 1 through 6 of SEQ ID NO: 16.

15. The modified human Interleukin-8 (IL-8) protein, wherein the modified human Interleukin-8 has:
(A) Arg, Lys or His substitution at position 70, and at least one modification selected from the group consisting of:
(B) Arg, Lys or His substitution at position 17, and
(C) Arg, Lys or His substitution at position 21.

16. The modified human Interleukin-8 (IL-8) protein, wherein the modified human Interleukin-8 has:
(A) Arg, Lys or His substitution at position 71, and at least one modification selected from the group consisting of:
(B) Arg, Lys or His substitution at position 17, and
(C) Arg, Lys or His substitution at position 21.

* * * * *

SEQUENCE LISTING

<160> NUMBER OF SEQ ID NOS: 614

<210> SEQ ID NO 1
<211> LENGTH: 6
<212> TYPE: PRT
<213> ORGANISM: homo sapiens

<400> SEQUENCE: 1

Lys Ser Leu Ser Leu Ser
1               5

<210> SEQ ID NO 2
<211> LENGTH: 6
<212> TYPE: PRT
<213> ORGANISM: artificial
<220> FEATURE:

```
<223> OTHER INFORMATION: Fc part of IgG

<400> SEQUENCE: 2

Lys Ser Lys Lys Leu Ser
1               5

<210> SEQ ID NO 3
<211> LENGTH: 6
<212> TYPE: PRT
<213> ORGANISM: homo sapiens

<400> SEQUENCE: 3

Trp Ile Ala Ser His Thr
1               5

<210> SEQ ID NO 4
<211> LENGTH: 6
<212> TYPE: PRT
<213> ORGANISM: artificial
<220> FEATURE:
<223> OTHER INFORMATION: C3 - complement binding factor

<400> SEQUENCE: 4

Trp Lys Ala Lys His Lys
1               5

<210> SEQ ID NO 5
<211> LENGTH: 8
<212> TYPE: PRT
<213> ORGANISM: homo sapiens

<400> SEQUENCE: 5

Met Leu Asp Ala Glu Arg Leu Lys
1               5

<210> SEQ ID NO 6
<211> LENGTH: 8
<212> TYPE: PRT
<213> ORGANISM: artificial
<220> FEATURE:
<223> OTHER INFORMATION: C4 - complement binding factor

<400> SEQUENCE: 6

Met Lys Lys Ala Lys Arg Leu Lys
1               5

<210> SEQ ID NO 7
<211> LENGTH: 31
<212> TYPE: DNA
<213> ORGANISM: artificial
<220> FEATURE:
<223> OTHER INFORMATION: primer for the mutation D6

<400> SEQUENCE: 7
caccatgtgt cagtgtataa agacatactc c                           31

<210> SEQ ID NO 8
<211> LENGTH: 55
<212> TYPE: DNA
<213> ORGANISM: artificial
<220> FEATURE:
<223> OTHER INFORMATION: primer for the mutation D6 F17R F21R

<400> SEQUENCE: 8
caccatgtgt cagtgtataa agacatactc caaacctagg cacccaaaa ggata    55
```

```
<210> SEQ ID NO 9
<211> LENGTH: 21
<212> TYPE: DNA
<213> ORGANISM: artificial
<220> FEATURE:
<223> OTHER INFORMATION: primer for the mutation E70R

<400> SEQUENCE: 9
ttatgaattc ctagccctct t                                              21

<210> SEQ ID NO 10
<211> LENGTH: 21
<212> TYPE: DNA
<213> ORGANISM: artificial
<220> FEATURE:
<223> OTHER INFORMATION: primer for the mutation E70K

<400> SEQUENCE: 10
ttatgaattc ttagccctct t                                              21

<210> SEQ ID NO 11
<211> LENGTH: 21
<212> TYPE: DNA
<213> ORGANISM: artificial
<220> FEATURE:
<223> OTHER INFORMATION: primer for the mutation N71K

<400> SEQUENCE: 11
ttatgacttc tcagccctct t                                              21

<210> SEQ ID NO 12
<211> LENGTH: 21
<212> TYPE: DNA
<213> ORGANISM: artificial
<220> FEATURE:
<223> OTHER INFORMATION: primer for the mutation E70K N71K

<400> SEQUENCE: 12
ttatgacttc ttagccctct t                                              21

<210> SEQ ID NO 13
<211> LENGTH: 21
<212> TYPE: DNA
<213> ORGANISM: artificial
<220> FEATURE:
<223> OTHER INFORMATION: primer for the mutation E70R N71K

<400> SEQUENCE: 13
ttatgacttc ctagccctct t                                              21

<210> SEQ ID NO 14
<211> LENGTH: 21
<212> TYPE: DNA
<213> ORGANISM: artificial
<220> FEATURE:
<223> OTHER INFORMATION: primer for the mutation E70K N71R

<400> SEQUENCE: 14
ttatgacctc ttagccctct t                                              21

<210> SEQ ID NO 15
<211> LENGTH: 21
<212> TYPE: DNA
<213> ORGANISM: artificial
<220> FEATURE:
<223> OTHER INFORMATION: primer for the mutation E70R N71R
```

<400> SEQUENCE: 15
ttatgacctc ctagccctct t                                             21

<210> SEQ ID NO 16
<211> LENGTH: 72
<212> TYPE: PRT
<213> ORGANISM: homo sapiens

<400> SEQUENCE: 16

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 17
<211> LENGTH: 3
<212> TYPE: PRT
<213> ORGANISM: homo sapiens

<400> SEQUENCE: 17

His Pro Lys
1

<210> SEQ ID NO 18
<211> LENGTH: 9
<212> TYPE: PRT
<213> ORGANISM: homo sapiens

<400> SEQUENCE: 18

Arg Val Val Glu Lys Phe Leu Lys Arg
1               5

<210> SEQ ID NO 19
<211> LENGTH: 73
<212> TYPE: PRT
<213> ORGANISM: homo sapiens

<400> SEQUENCE: 19

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65                  70

<210> SEQ ID NO 20
<211> LENGTH: 3
<212> TYPE: PRT
<213> ORGANISM: homo sapiens

```
<400> SEQUENCE: 20

His Pro Lys
1

<210> SEQ ID NO 21
<211> LENGTH: 4
<212> TYPE: PRT
<213> ORGANISM: homo sapiens

<400> SEQUENCE: 21

Lys Asn Gly Arg
1

<210> SEQ ID NO 22
<211> LENGTH: 9
<212> TYPE: PRT
<213> ORGANISM: homo sapiens

<400> SEQUENCE: 22

Lys Lys Ile Ile Glu Lys Met Leu Lys
1               5

<210> SEQ ID NO 23
<211> LENGTH: 73
<212> TYPE: PRT
<213> ORGANISM: homo sapiens

<400> SEQUENCE: 23

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
                20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70

<210> SEQ ID NO 24
<211> LENGTH: 3
<212> TYPE: PRT
<213> ORGANISM: homo sapiens

<400> SEQUENCE: 24

His Leu Lys
1

<210> SEQ ID NO 25
<211> LENGTH: 9
<212> TYPE: PRT
<213> ORGANISM: homo sapiens

<400> SEQUENCE: 25

Lys Lys Ile Ile Glu Lys Met Leu Lys
1               5

<210> SEQ ID NO 26
<211> LENGTH: 70
<212> TYPE: PRT
<213> ORGANISM: homo sapiens

<400> SEQUENCE: 26
```

```
Ala Glu Leu Arg Cys Leu Cys Ile Lys Thr Thr Ser Gly Ile His Pro
1               5                   10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
65                  70

<210> SEQ ID NO 27
<211> LENGTH: 3
<212> TYPE: PRT
<213> ORGANISM: homo sapiens

<400> SEQUENCE: 27

His Pro Lys
1

<210> SEQ ID NO 28
<211> LENGTH: 4
<212> TYPE: PRT
<213> ORGANISM: homo sapiens

<400> SEQUENCE: 28

Lys Asp Gly Arg
1

<210> SEQ ID NO 29
<211> LENGTH: 6
<212> TYPE: PRT
<213> ORGANISM: homo sapiens

<400> SEQUENCE: 29

Lys Lys Ile Val Gln Lys
1               5

<210> SEQ ID NO 30
<211> LENGTH: 70
<212> TYPE: PRT
<213> ORGANISM: homo sapiens

<400> SEQUENCE: 30

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 31
<211> LENGTH: 4
<212> TYPE: PRT
<213> ORGANISM: homo sapiens

<400> SEQUENCE: 31
```

Arg Pro Arg His
1

<210> SEQ ID NO 32
<211> LENGTH: 4
<212> TYPE: PRT
<213> ORGANISM: homo sapiens

<400> SEQUENCE: 32

Lys Asn Gly Arg
1

<210> SEQ ID NO 33
<211> LENGTH: 6
<212> TYPE: PRT
<213> ORGANISM: homo sapiens

<400> SEQUENCE: 33

Lys Lys Ile Ile Lys Lys
1               5

<210> SEQ ID NO 34
<211> LENGTH: 67
<212> TYPE: PRT
<213> ORGANISM: homo sapiens

<400> SEQUENCE: 34

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 35
<211> LENGTH: 4
<212> TYPE: PRT
<213> ORGANISM: homo sapiens

<400> SEQUENCE: 35

Lys His Leu Lys
1

<210> SEQ ID NO 36
<211> LENGTH: 3
<212> TYPE: PRT
<213> ORGANISM: homo sapiens

<400> SEQUENCE: 36

Arg Leu Lys
1

<210> SEQ ID NO 37
<211> LENGTH: 68
<212> TYPE: PRT
<213> ORGANISM: homo sapiens

<400> SEQUENCE: 37

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 38
<211> LENGTH: 7
<212> TYPE: PRT
<213> ORGANISM: homo sapiens

<400> SEQUENCE: 38

```
Arg Pro Leu Pro Arg Ala His
1               5
```

<210> SEQ ID NO 39
<211> LENGTH: 4
<212> TYPE: PRT
<213> ORGANISM: homo sapiens

<400> SEQUENCE: 39

```
Arg Lys Asn Arg
1
```

<210> SEQ ID NO 40
<211> LENGTH: 76
<212> TYPE: PRT
<213> ORGANISM: homo sapiens

<400> SEQUENCE: 40

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

<210> SEQ ID NO 41
<211> LENGTH: 7
<212> TYPE: PRT
<213> ORGANISM: homo sapiens

<400> SEQUENCE: 41

```
Arg Lys Ile Pro Ile Gln Arg
1               5
```

<210> SEQ ID NO 42
<211> LENGTH: 4
<212> TYPE: PRT
<213> ORGANISM: homo sapiens

<400> SEQUENCE: 42

```
Lys Arg Gly Lys
1

<210> SEQ ID NO 43
<211> LENGTH: 76
<212> TYPE: PRT
<213> ORGANISM: homo sapiens

<400> SEQUENCE: 43

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
        50                  55                  60

Lys His Leu Asp Lys Lys Thr Gln Thr Pro Lys Leu
65                  70                  75

<210> SEQ ID NO 44
<211> LENGTH: 3
<212> TYPE: PRT
<213> ORGANISM: homo sapiens

<400> SEQUENCE: 44

Lys Gln Arg
1

<210> SEQ ID NO 45
<211> LENGTH: 4
<212> TYPE: PRT
<213> ORGANISM: homo sapiens

<400> SEQUENCE: 45

Lys Leu Asp Lys
1

<210> SEQ ID NO 46
<211> LENGTH: 6
<212> TYPE: PRT
<213> ORGANISM: homo sapiens

<400> SEQUENCE: 46

Lys His Leu Asp Lys Lys
1               5

<210> SEQ ID NO 47
<211> LENGTH: 69
<212> TYPE: PRT
<213> ORGANISM: homo sapiens

<400> SEQUENCE: 47

Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
                20                  25                  30

Gln Cys Ser Lys Pro Gly Val Ile Phe Leu Thr Lys Arg Ser Arg Gln
            35                  40                  45

Val Cys Ala Asp Pro Ser Glu Glu Trp Val Gln Lys Tyr Val Ser Asp
        50                  55                  60
```

```
Leu Glu Leu Ser Ala
 65

<210> SEQ ID NO 48
<211> LENGTH: 4
<212> TYPE: PRT
<213> ORGANISM: homo sapiens

<400> SEQUENCE: 48

Lys Arg Ser Arg
1

<210> SEQ ID NO 49
<211> LENGTH: 69
<212> TYPE: PRT
<213> ORGANISM: homo sapiens

<400> SEQUENCE: 49

Ala Pro Met Gly Ser Asp Pro Pro Thr Ala Cys Cys Phe Ser Tyr Thr
1               5                  10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
 65

<210> SEQ ID NO 50
<211> LENGTH: 4
<212> TYPE: PRT
<213> ORGANISM: homo sapiens

<400> SEQUENCE: 50

Lys Arg Ser Lys
1

<210> SEQ ID NO 51
<211> LENGTH: 77
<212> TYPE: PRT
<213> ORGANISM: homo sapiens

<400> SEQUENCE: 51

Met Asp Arg Phe His Ala Thr Ser Ala Asp Cys Cys Ile Ser Tyr Thr
1               5                  10                  15

Pro Arg Ser Ile Pro Cys Ser Leu Leu Glu Ser Tyr Phe Glu Thr Asn
            20                  25                  30

Ser Glu Cys Ser Lys Pro Gly Val Ile Phe Leu Thr Lys Lys Gly Arg
        35                  40                  45

Arg Phe Cys Ala Asn Pro Ser Asp Lys Gln Val Gln Val Cys Met Arg
    50                  55                  60

Met Leu Lys Leu Asp Thr Arg Ile Lys Thr Lys Asn
 65                 70                  75

<210> SEQ ID NO 52
<211> LENGTH: 4
<212> TYPE: PRT
<213> ORGANISM: homo sapiens

<400> SEQUENCE: 52
```

-continued

```
Lys Lys Gly Arg
1

<210> SEQ ID NO 53
<211> LENGTH: 66
<212> TYPE: PRT
<213> ORGANISM: homo sapiens

<400> SEQUENCE: 53

His Phe Ala Ala Asp Cys Cys Thr Ser Tyr Ile Ser Gln Ser Ile Pro
1               5                   10                  15

Cys Ser Leu Met Lys Ser Tyr Phe Glu Thr Ser Ser Glu Cys Ser Lys
            20                  25                  30

Pro Gly Val Ile Phe Leu Thr Lys Lys Gly Arg Gln Val Cys Ala Lys
        35                  40                  45

Pro Ser Gly Pro Gly Val Gln Asp Cys Met Lys Lys Leu Lys Pro Tyr
    50                  55                  60

Ser Ile
65

<210> SEQ ID NO 54
<211> LENGTH: 4
<212> TYPE: PRT
<213> ORGANISM: homo sapiens

<400> SEQUENCE: 54

Lys Lys Gly Arg
1

<210> SEQ ID NO 55
<211> LENGTH: 6
<212> TYPE: PRT
<213> ORGANISM: homo sapiens

<400> SEQUENCE: 55

Thr Arg Arg Ala Lys Glu
1               5

<210> SEQ ID NO 56
<211> LENGTH: 6
<212> TYPE: PRT
<213> ORGANISM: homo sapiens

<400> SEQUENCE: 56

Gln Lys Lys Ile Arg Ser
1               5

<210> SEQ ID NO 57
<211> LENGTH: 6
<212> TYPE: PRT
<213> ORGANISM: homo sapiens

<400> SEQUENCE: 57

Pro Lys Arg Arg Lys Asn
1               5

<210> SEQ ID NO 58
<211> LENGTH: 8
<212> TYPE: PRT
<213> ORGANISM: homo sapiens

<400> SEQUENCE: 58

Ser Lys Arg Arg Gly Lys Lys Val
```

-continued

```
1               5

<210> SEQ ID NO 59
<211> LENGTH: 6
<212> TYPE: PRT
<213> ORGANISM: homo sapiens

<400> SEQUENCE: 59

Glu Arg Arg Leu Lys Met
1               5

<210> SEQ ID NO 60
<211> LENGTH: 6
<212> TYPE: PRT
<213> ORGANISM: homo sapiens

<400> SEQUENCE: 60

Lys Arg Arg Gly Lys Lys
1               5

<210> SEQ ID NO 61
<211> LENGTH: 8
<212> TYPE: PRT
<213> ORGANISM: homo sapiens

<400> SEQUENCE: 61

Glu Lys Arg Arg Arg Ala Arg Ile
1               5

<210> SEQ ID NO 62
<211> LENGTH: 6
<212> TYPE: PRT
<213> ORGANISM: homo sapiens

<400> SEQUENCE: 62

Glu Lys Arg Arg Arg Ala
1               5

<210> SEQ ID NO 63
<211> LENGTH: 8
<212> TYPE: PRT
<213> ORGANISM: homo sapiens

<400> SEQUENCE: 63

Met Lys Lys Lys Lys Lys Lys Lys
1               5

<210> SEQ ID NO 64
<211> LENGTH: 6
<212> TYPE: PRT
<213> ORGANISM: homo sapiens

<400> SEQUENCE: 64

Met Lys Lys Lys Lys Lys
1               5

<210> SEQ ID NO 65
<211> LENGTH: 6
<212> TYPE: PRT
<213> ORGANISM: homo sapiens

<400> SEQUENCE: 65

Arg Arg Arg Leu Arg Ser
1               5
```

```
<210> SEQ ID NO 66
<211> LENGTH: 6
<212> TYPE: PRT
<213> ORGANISM: homo sapiens

<400> SEQUENCE: 66

Val Arg Lys Leu Lys Gly
1               5

<210> SEQ ID NO 67
<211> LENGTH: 6
<212> TYPE: PRT
<213> ORGANISM: homo sapiens

<400> SEQUENCE: 67

Leu Arg Lys Ala Arg Asp
1               5

<210> SEQ ID NO 68
<211> LENGTH: 6
<212> TYPE: PRT
<213> ORGANISM: homo sapiens

<400> SEQUENCE: 68

Arg Arg Lys Leu Arg Glu
1               5

<210> SEQ ID NO 69
<211> LENGTH: 6
<212> TYPE: PRT
<213> ORGANISM: homo sapiens

<400> SEQUENCE: 69

Ala Lys Lys Gly Lys Gly
1               5

<210> SEQ ID NO 70
<211> LENGTH: 6
<212> TYPE: PRT
<213> ORGANISM: homo sapiens

<400> SEQUENCE: 70

Ala Lys Lys Leu Arg Glu
1               5

<210> SEQ ID NO 71
<211> LENGTH: 6
<212> TYPE: PRT
<213> ORGANISM: homo sapiens

<400> SEQUENCE: 71

Glu Lys Arg Thr Lys Asp
1               5

<210> SEQ ID NO 72
<211> LENGTH: 6
<212> TYPE: PRT
<213> ORGANISM: homo sapiens

<400> SEQUENCE: 72

Thr Lys Arg Lys Arg Val
1               5

<210> SEQ ID NO 73
```

```
<211> LENGTH: 6
<212> TYPE: PRT
<213> ORGANISM: homo sapiens

<400> SEQUENCE: 73

Trp Lys Lys Lys Lys Val
1               5

<210> SEQ ID NO 74
<211> LENGTH: 6
<212> TYPE: PRT
<213> ORGANISM: homo sapiens

<400> SEQUENCE: 74

Pro Arg Arg Ile Lys Ala
1               5

<210> SEQ ID NO 75
<211> LENGTH: 6
<212> TYPE: PRT
<213> ORGANISM: homo sapiens

<400> SEQUENCE: 75

Lys Arg Arg Thr Arg Val
1               5

<210> SEQ ID NO 76
<211> LENGTH: 8
<212> TYPE: PRT
<213> ORGANISM: homo sapiens

<400> SEQUENCE: 76

Thr Lys Lys Lys Thr Arg Arg Arg
1               5

<210> SEQ ID NO 77
<211> LENGTH: 8
<212> TYPE: PRT
<213> ORGANISM: homo sapiens

<400> SEQUENCE: 77

Gly Lys Arg Arg Arg Arg Arg Gly
1               5

<210> SEQ ID NO 78
<211> LENGTH: 6
<212> TYPE: PRT
<213> ORGANISM: homo sapiens

<400> SEQUENCE: 78

Ala Arg Lys Gly Lys Arg
1               5

<210> SEQ ID NO 79
<211> LENGTH: 6
<212> TYPE: PRT
<213> ORGANISM: homo sapiens

<400> SEQUENCE: 79

Gly Lys Lys Thr Lys Lys
1               5

<210> SEQ ID NO 80
<211> LENGTH: 6
<212> TYPE: PRT
```

<213> ORGANISM: homo sapiens

<400> SEQUENCE: 80

Thr Arg Arg Arg Arg Ala
1               5

<210> SEQ ID NO 81
<211> LENGTH: 6
<212> TYPE: PRT
<213> ORGANISM: homo sapiens

<400> SEQUENCE: 81

Gly Lys Arg Arg Arg Arg
1               5

<210> SEQ ID NO 82
<211> LENGTH: 6
<212> TYPE: PRT
<213> ORGANISM: homo sapiens

<400> SEQUENCE: 82

Ala Arg Lys Gln Lys Ala
1               5

<210> SEQ ID NO 83
<211> LENGTH: 6
<212> TYPE: PRT
<213> ORGANISM: homo sapiens

<400> SEQUENCE: 83

Lys Lys Lys Ile Lys Glu
1               5

<210> SEQ ID NO 84
<211> LENGTH: 6
<212> TYPE: PRT
<213> ORGANISM: homo sapiens

<400> SEQUENCE: 84

Val Arg Arg Cys Lys Ile
1               5

<210> SEQ ID NO 85
<211> LENGTH: 6
<212> TYPE: PRT
<213> ORGANISM: homo sapiens

<400> SEQUENCE: 85

Glu Arg Arg Ala Arg Leu
1               5

<210> SEQ ID NO 86
<211> LENGTH: 6
<212> TYPE: PRT
<213> ORGANISM: homo sapiens

<400> SEQUENCE: 86

Met Lys Arg Leu Lys Val
1               5

<210> SEQ ID NO 87
<211> LENGTH: 6
<212> TYPE: PRT
<213> ORGANISM: homo sapiens

```
<400> SEQUENCE: 87

Leu Lys Arg Pro Lys Asp
1               5

<210> SEQ ID NO 88
<211> LENGTH: 6
<212> TYPE: PRT
<213> ORGANISM: homo sapiens

<400> SEQUENCE: 88

Gln Arg Lys Ser Lys Pro
1               5

<210> SEQ ID NO 89
<211> LENGTH: 8
<212> TYPE: PRT
<213> ORGANISM: homo sapiens

<400> SEQUENCE: 89

Leu Lys Arg Lys Met Phe Lys Met
1               5

<210> SEQ ID NO 90
<211> LENGTH: 6
<212> TYPE: PRT
<213> ORGANISM: homo sapiens

<400> SEQUENCE: 90

Leu Lys Lys Leu Lys Thr
1               5

<210> SEQ ID NO 91
<211> LENGTH: 6
<212> TYPE: PRT
<213> ORGANISM: homo sapiens

<400> SEQUENCE: 91

Val Lys Lys Glu Lys Leu
1               5

<210> SEQ ID NO 92
<211> LENGTH: 6
<212> TYPE: PRT
<213> ORGANISM: homo sapiens

<400> SEQUENCE: 92

Glu Lys Arg Glu Arg Thr
1               5

<210> SEQ ID NO 93
<211> LENGTH: 6
<212> TYPE: PRT
<213> ORGANISM: homo sapiens

<400> SEQUENCE: 93

Leu Lys Arg Val Arg Glu
1               5

<210> SEQ ID NO 94
<211> LENGTH: 6
<212> TYPE: PRT
<213> ORGANISM: homo sapiens

<400> SEQUENCE: 94
```

```
Val Arg Arg Gly Arg Ile
1               5

<210> SEQ ID NO 95
<211> LENGTH: 6
<212> TYPE: PRT
<213> ORGANISM: homo sapiens

<400> SEQUENCE: 95

Leu Lys Lys Pro Arg Lys
1               5

<210> SEQ ID NO 96
<211> LENGTH: 6
<212> TYPE: PRT
<213> ORGANISM: homo sapiens

<400> SEQUENCE: 96

Asn Arg Arg Thr Lys Trp
1               5

<210> SEQ ID NO 97
<211> LENGTH: 8
<212> TYPE: PRT
<213> ORGANISM: homo sapiens

<400> SEQUENCE: 97

Ser Arg Lys Lys Arg Glu Arg Asp
1               5

<210> SEQ ID NO 98
<211> LENGTH: 8
<212> TYPE: PRT
<213> ORGANISM: homo sapiens

<400> SEQUENCE: 98

Gly Lys Arg Lys Ala Gly Lys Lys
1               5

<210> SEQ ID NO 99
<211> LENGTH: 6
<212> TYPE: PRT
<213> ORGANISM: homo sapiens

<400> SEQUENCE: 99

Met Arg Lys Val Lys Phe
1               5

<210> SEQ ID NO 100
<211> LENGTH: 6
<212> TYPE: PRT
<213> ORGANISM: homo sapiens

<400> SEQUENCE: 100

Ile Lys Arg Gln Lys Gln
1               5

<210> SEQ ID NO 101
<211> LENGTH: 6
<212> TYPE: PRT
<213> ORGANISM: homo sapiens

<400> SEQUENCE: 101

Ala Arg Arg Lys Arg Met
1               5
```

```
<210> SEQ ID NO 102
<211> LENGTH: 6
<212> TYPE: PRT
<213> ORGANISM: homo sapiens

<400> SEQUENCE: 102

Ser Arg Lys Lys Arg Glu
1               5

<210> SEQ ID NO 103
<211> LENGTH: 6
<212> TYPE: PRT
<213> ORGANISM: homo sapiens

<400> SEQUENCE: 103

Lys Lys Lys Leu Lys Ile
1               5

<210> SEQ ID NO 104
<211> LENGTH: 6
<212> TYPE: PRT
<213> ORGANISM: homo sapiens

<400> SEQUENCE: 104

Ala Arg Arg Ser Arg Ser
1               5

<210> SEQ ID NO 105
<211> LENGTH: 6
<212> TYPE: PRT
<213> ORGANISM: homo sapiens

<400> SEQUENCE: 105

Thr Arg Lys Arg Lys Arg
1               5

<210> SEQ ID NO 106
<211> LENGTH: 6
<212> TYPE: PRT
<213> ORGANISM: homo sapiens

<400> SEQUENCE: 106

Val Lys Lys Ala Lys Thr
1               5

<210> SEQ ID NO 107
<211> LENGTH: 6
<212> TYPE: PRT
<213> ORGANISM: homo sapiens

<400> SEQUENCE: 107

Gly Lys Lys Asp Arg Arg
1               5

<210> SEQ ID NO 108
<211> LENGTH: 6
<212> TYPE: PRT
<213> ORGANISM: homo sapiens

<400> SEQUENCE: 108

Arg Arg Arg Pro Lys Thr
1               5
```

```
<210> SEQ ID NO 109
<211> LENGTH: 6
<212> TYPE: PRT
<213> ORGANISM: homo sapiens

<400> SEQUENCE: 109

Glu Arg Lys Arg Lys Ala
1               5

<210> SEQ ID NO 110
<211> LENGTH: 6
<212> TYPE: PRT
<213> ORGANISM: homo sapiens

<400> SEQUENCE: 110

Pro Lys Lys Ser Lys Ser
1               5

<210> SEQ ID NO 111
<211> LENGTH: 6
<212> TYPE: PRT
<213> ORGANISM: homo sapiens

<400> SEQUENCE: 111

Glu Lys Lys Pro Arg Arg
1               5

<210> SEQ ID NO 112
<211> LENGTH: 6
<212> TYPE: PRT
<213> ORGANISM: homo sapiens

<400> SEQUENCE: 112

Glu Lys Lys Gly Arg Lys
1               5

<210> SEQ ID NO 113
<211> LENGTH: 6
<212> TYPE: PRT
<213> ORGANISM: homo sapiens

<400> SEQUENCE: 113

Glu Arg Lys Phe Lys Ala
1               5

<210> SEQ ID NO 114
<211> LENGTH: 6
<212> TYPE: PRT
<213> ORGANISM: homo sapiens

<400> SEQUENCE: 114

Val Lys Lys Asn Lys Gln
1               5

<210> SEQ ID NO 115
<211> LENGTH: 6
<212> TYPE: PRT
<213> ORGANISM: homo sapiens

<400> SEQUENCE: 115

Val Arg Arg Asp Arg Val
1               5

<210> SEQ ID NO 116
<211> LENGTH: 6
```

```
<212> TYPE: PRT
<213> ORGANISM: homo sapiens

<400> SEQUENCE: 116

Pro Arg Lys Val Lys Ser
1               5

<210> SEQ ID NO 117
<211> LENGTH: 6
<212> TYPE: PRT
<213> ORGANISM: homo sapiens

<400> SEQUENCE: 117

Val Arg Lys Asp Lys Leu
1               5

<210> SEQ ID NO 118
<211> LENGTH: 8
<212> TYPE: PRT
<213> ORGANISM: homo sapiens

<400> SEQUENCE: 118

Gly Arg Lys Lys Cys Glu Arg Tyr
1               5

<210> SEQ ID NO 119
<211> LENGTH: 6
<212> TYPE: PRT
<213> ORGANISM: homo sapiens

<400> SEQUENCE: 119

Val Lys Lys Asn Arg Tyr
1               5

<210> SEQ ID NO 120
<211> LENGTH: 6
<212> TYPE: PRT
<213> ORGANISM: homo sapiens

<400> SEQUENCE: 120

Val Arg Lys Ile Arg Phe
1               5

<210> SEQ ID NO 121
<211> LENGTH: 8
<212> TYPE: PRT
<213> ORGANISM: homo sapiens

<400> SEQUENCE: 121

Ser Arg Lys Arg Gln Thr Arg Arg
1               5

<210> SEQ ID NO 122
<211> LENGTH: 6
<212> TYPE: PRT
<213> ORGANISM: homo sapiens

<400> SEQUENCE: 122

Thr Arg Arg Arg Arg Asn
1               5

<210> SEQ ID NO 123
<211> LENGTH: 8
<212> TYPE: PRT
<213> ORGANISM: homo sapiens
```

```
<400> SEQUENCE: 123

Ala Arg Arg Lys Gly Arg Arg Gly
1               5

<210> SEQ ID NO 124
<211> LENGTH: 8
<212> TYPE: PRT
<213> ORGANISM: homo sapiens

<400> SEQUENCE: 124

Glu Lys Lys Arg His Ser Lys Val
1               5

<210> SEQ ID NO 125
<211> LENGTH: 6
<212> TYPE: PRT
<213> ORGANISM: homo sapiens

<400> SEQUENCE: 125

Arg Arg Lys Gly Arg Arg
1               5

<210> SEQ ID NO 126
<211> LENGTH: 8
<212> TYPE: PRT
<213> ORGANISM: homo sapiens

<400> SEQUENCE: 126

Pro Lys Arg Lys Asn Lys Lys Ser
1               5

<210> SEQ ID NO 127
<211> LENGTH: 6
<212> TYPE: PRT
<213> ORGANISM: homo sapiens

<400> SEQUENCE: 127

Asp Lys Lys Leu Arg Glu
1               5

<210> SEQ ID NO 128
<211> LENGTH: 6
<212> TYPE: PRT
<213> ORGANISM: homo sapiens

<400> SEQUENCE: 128

Lys Arg Lys Asn Lys Lys
1               5

<210> SEQ ID NO 129
<211> LENGTH: 6
<212> TYPE: PRT
<213> ORGANISM: homo sapiens

<400> SEQUENCE: 129

Val Lys Arg Leu Lys Ser
1               5

<210> SEQ ID NO 130
<211> LENGTH: 8
<212> TYPE: PRT
<213> ORGANISM: homo sapiens

<400> SEQUENCE: 130
```

```
Ala Lys Lys Lys Thr Lys Lys Arg
1               5

<210> SEQ ID NO 131
<211> LENGTH: 6
<212> TYPE: PRT
<213> ORGANISM: homo sapiens

<400> SEQUENCE: 131

Lys Lys Lys Thr Lys Lys
1               5

<210> SEQ ID NO 132
<211> LENGTH: 6
<212> TYPE: PRT
<213> ORGANISM: homo sapiens

<400> SEQUENCE: 132

Glu Arg Arg Arg Arg Glu
1               5

<210> SEQ ID NO 133
<211> LENGTH: 6
<212> TYPE: PRT
<213> ORGANISM: homo sapiens

<400> SEQUENCE: 133

Arg Lys Arg Gln Arg Glu
1               5

<210> SEQ ID NO 134
<211> LENGTH: 6
<212> TYPE: PRT
<213> ORGANISM: homo sapiens

<400> SEQUENCE: 134

Arg Arg Lys Trp Lys Glu
1               5

<210> SEQ ID NO 135
<211> LENGTH: 6
<212> TYPE: PRT
<213> ORGANISM: homo sapiens

<400> SEQUENCE: 135

Glu Lys Arg Lys Arg Lys
1               5

<210> SEQ ID NO 136
<211> LENGTH: 6
<212> TYPE: PRT
<213> ORGANISM: homo sapiens

<400> SEQUENCE: 136

Asp Lys Arg Glu Lys Ala
1               5

<210> SEQ ID NO 137
<211> LENGTH: 6
<212> TYPE: PRT
<213> ORGANISM: homo sapiens

<400> SEQUENCE: 137

Arg Arg Arg Gln Lys Glu
```

```
<210> SEQ ID NO 138
<211> LENGTH: 6
<212> TYPE: PRT
<213> ORGANISM: homo sapiens

<400> SEQUENCE: 138

Met Lys Lys Glu Lys Asp
1               5

<210> SEQ ID NO 139
<211> LENGTH: 6
<212> TYPE: PRT
<213> ORGANISM: homo sapiens

<400> SEQUENCE: 139

Val Lys Arg Asp Arg Ile
1               5

<210> SEQ ID NO 140
<211> LENGTH: 9
<212> TYPE: PRT
<213> ORGANISM: homo sapiens

<400> SEQUENCE: 140

Ala Lys Lys Lys Thr Lys Lys Arg Asp
1               5

<210> SEQ ID NO 141
<211> LENGTH: 6
<212> TYPE: PRT
<213> ORGANISM: homo sapiens

<400> SEQUENCE: 141

Ala Arg Arg Thr Arg Ser
1               5

<210> SEQ ID NO 142
<211> LENGTH: 6
<212> TYPE: PRT
<213> ORGANISM: homo sapiens

<400> SEQUENCE: 142

Lys Arg Lys Ile Arg Asp
1               5

<210> SEQ ID NO 143
<211> LENGTH: 6
<212> TYPE: PRT
<213> ORGANISM: homo sapiens

<400> SEQUENCE: 143

Glu Lys Lys Ala Arg Lys
1               5

<210> SEQ ID NO 144
<211> LENGTH: 6
<212> TYPE: PRT
<213> ORGANISM: homo sapiens

<400> SEQUENCE: 144

Ile Arg Lys Ser Lys Asn
1               5
```

```
<210> SEQ ID NO 145
<211> LENGTH: 6
<212> TYPE: PRT
<213> ORGANISM: homo sapiens

<400> SEQUENCE: 145

Ala Arg Lys Glu Arg Glu
1               5

<210> SEQ ID NO 146
<211> LENGTH: 6
<212> TYPE: PRT
<213> ORGANISM: homo sapiens

<400> SEQUENCE: 146

Leu Lys Arg Asp Arg Phe
1               5

<210> SEQ ID NO 147
<211> LENGTH: 6
<212> TYPE: PRT
<213> ORGANISM: homo sapiens

<400> SEQUENCE: 147

His Arg Arg Pro Arg Glu
1               5

<210> SEQ ID NO 148
<211> LENGTH: 6
<212> TYPE: PRT
<213> ORGANISM: homo sapiens

<400> SEQUENCE: 148

Pro Arg Lys Lys Arg Pro
1               5

<210> SEQ ID NO 149
<211> LENGTH: 6
<212> TYPE: PRT
<213> ORGANISM: homo sapiens

<400> SEQUENCE: 149

Asp Arg Lys Gln Lys Val
1               5

<210> SEQ ID NO 150
<211> LENGTH: 8
<212> TYPE: PRT
<213> ORGANISM: homo sapiens

<400> SEQUENCE: 150

Ser Arg Arg Lys Arg Leu Arg His
1               5

<210> SEQ ID NO 151
<211> LENGTH: 6
<212> TYPE: PRT
<213> ORGANISM: homo sapiens

<400> SEQUENCE: 151

Ser Arg Arg Lys Arg Leu
1               5

<210> SEQ ID NO 152
```

```
<211> LENGTH: 6
<212> TYPE: PRT
<213> ORGANISM: homo sapiens

<400> SEQUENCE: 152

Gly Lys Lys Val Arg Val
1               5

<210> SEQ ID NO 153
<211> LENGTH: 6
<212> TYPE: PRT
<213> ORGANISM: homo sapiens

<400> SEQUENCE: 153

Ala Arg Lys Arg Arg Leu
1               5

<210> SEQ ID NO 154
<211> LENGTH: 6
<212> TYPE: PRT
<213> ORGANISM: homo sapiens

<400> SEQUENCE: 154

Gly Lys Arg Met Arg Thr
1               5

<210> SEQ ID NO 155
<211> LENGTH: 6
<212> TYPE: PRT
<213> ORGANISM: homo sapiens

<400> SEQUENCE: 155

Asn Arg Arg Val Lys His
1               5

<210> SEQ ID NO 156
<211> LENGTH: 6
<212> TYPE: PRT
<213> ORGANISM: homo sapiens

<400> SEQUENCE: 156

Ala Arg Arg Met Lys Glu
1               5

<210> SEQ ID NO 157
<211> LENGTH: 6
<212> TYPE: PRT
<213> ORGANISM: homo sapiens

<400> SEQUENCE: 157

His Arg Lys Lys Arg Leu
1               5

<210> SEQ ID NO 158
<211> LENGTH: 6
<212> TYPE: PRT
<213> ORGANISM: homo sapiens

<400> SEQUENCE: 158

Ser Lys Lys Glu Lys Val
1               5

<210> SEQ ID NO 159
<211> LENGTH: 6
<212> TYPE: PRT
```

<213> ORGANISM: homo sapiens

<400> SEQUENCE: 159

Ser Lys Arg Cys Lys Lys
1               5

<210> SEQ ID NO 160
<211> LENGTH: 6
<212> TYPE: PRT
<213> ORGANISM: homo sapiens

<400> SEQUENCE: 160

Leu Lys Lys Tyr Lys Glu
1               5

<210> SEQ ID NO 161
<211> LENGTH: 6
<212> TYPE: PRT
<213> ORGANISM: homo sapiens

<400> SEQUENCE: 161

Ile Lys Arg Leu Lys Glu
1               5

<210> SEQ ID NO 162
<211> LENGTH: 9
<212> TYPE: PRT
<213> ORGANISM: homo sapiens

<400> SEQUENCE: 162

Leu Lys Lys Tyr Lys Glu Lys Arg Thr
1               5

<210> SEQ ID NO 163
<211> LENGTH: 6
<212> TYPE: PRT
<213> ORGANISM: homo sapiens

<400> SEQUENCE: 163

Ala Arg Lys Ile Arg Thr
1               5

<210> SEQ ID NO 164
<211> LENGTH: 6
<212> TYPE: PRT
<213> ORGANISM: homo sapiens

<400> SEQUENCE: 164

Asp Arg Arg Val Arg Ser
1               5

<210> SEQ ID NO 165
<211> LENGTH: 6
<212> TYPE: PRT
<213> ORGANISM: homo sapiens

<400> SEQUENCE: 165

Pro Arg Lys Cys Arg Gln
1               5

<210> SEQ ID NO 166
<211> LENGTH: 6
<212> TYPE: PRT
<213> ORGANISM: homo sapiens

```
<400> SEQUENCE: 166

His Arg Arg His Arg His
1               5

<210> SEQ ID NO 167
<211> LENGTH: 6
<212> TYPE: PRT
<213> ORGANISM: homo sapiens

<400> SEQUENCE: 167

Arg Lys Arg Asp Arg Glu
1               5

<210> SEQ ID NO 168
<211> LENGTH: 6
<212> TYPE: PRT
<213> ORGANISM: homo sapiens

<400> SEQUENCE: 168

Ser Lys Lys Lys Lys Leu
1               5

<210> SEQ ID NO 169
<211> LENGTH: 8
<212> TYPE: PRT
<213> ORGANISM: homo sapiens

<400> SEQUENCE: 169

Leu Lys Lys Lys Glu Glu Arg Leu
1               5

<210> SEQ ID NO 170
<211> LENGTH: 6
<212> TYPE: PRT
<213> ORGANISM: homo sapiens

<400> SEQUENCE: 170

Glu Lys Lys Gln Arg Arg
1               5

<210> SEQ ID NO 171
<211> LENGTH: 6
<212> TYPE: PRT
<213> ORGANISM: homo sapiens

<400> SEQUENCE: 171

Ala Lys Lys Met Arg Pro
1               5

<210> SEQ ID NO 172
<211> LENGTH: 6
<212> TYPE: PRT
<213> ORGANISM: homo sapiens

<400> SEQUENCE: 172

Met Arg Lys Gly Lys Gln
1               5

<210> SEQ ID NO 173
<211> LENGTH: 8
<212> TYPE: PRT
<213> ORGANISM: homo sapiens

<400> SEQUENCE: 173
```

```
Glu Arg Arg Arg Arg Pro Arg Asp
1               5
```

<210> SEQ ID NO 174
<211> LENGTH: 6
<212> TYPE: PRT
<213> ORGANISM: homo sapiens

<400> SEQUENCE: 174

```
Ser Arg Lys Trp Arg Pro
1               5
```

<210> SEQ ID NO 175
<211> LENGTH: 6
<212> TYPE: PRT
<213> ORGANISM: homo sapiens

<400> SEQUENCE: 175

```
Glu Arg Arg Arg Arg Pro
1               5
```

<210> SEQ ID NO 176
<211> LENGTH: 8
<212> TYPE: PRT
<213> ORGANISM: homo sapiens

<400> SEQUENCE: 176

```
Gly Lys Lys Lys Arg Lys Arg
1               5
```

<210> SEQ ID NO 177
<211> LENGTH: 6
<212> TYPE: PRT
<213> ORGANISM: homo sapiens

<400> SEQUENCE: 177

```
Ala Arg Lys Glu Arg Gln
1               5
```

<210> SEQ ID NO 178
<211> LENGTH: 6
<212> TYPE: PRT
<213> ORGANISM: homo sapiens

<400> SEQUENCE: 178

```
Gly Lys Lys Lys Lys Arg
1               5
```

<210> SEQ ID NO 179
<211> LENGTH: 9
<212> TYPE: PRT
<213> ORGANISM: homo sapiens

<400> SEQUENCE: 179

```
Gly Lys Lys Lys Lys Arg Lys Arg Glu
1               5
```

<210> SEQ ID NO 180
<211> LENGTH: 6
<212> TYPE: PRT
<213> ORGANISM: homo sapiens

<400> SEQUENCE: 180

```
Val Arg Arg Tyr Arg Glu
1               5
```

```
<210> SEQ ID NO 181
<211> LENGTH: 6
<212> TYPE: PRT
<213> ORGANISM: homo sapiens

<400> SEQUENCE: 181

Asn Lys Lys Glu Lys Met
1               5

<210> SEQ ID NO 182
<211> LENGTH: 6
<212> TYPE: PRT
<213> ORGANISM: homo sapiens

<400> SEQUENCE: 182

Lys Lys Arg Glu Lys Glu
1               5

<210> SEQ ID NO 183
<211> LENGTH: 6
<212> TYPE: PRT
<213> ORGANISM: homo sapiens

<400> SEQUENCE: 183

Lys Lys Lys Phe Lys Leu
1               5

<210> SEQ ID NO 184
<211> LENGTH: 6
<212> TYPE: PRT
<213> ORGANISM: homo sapiens

<400> SEQUENCE: 184

Leu Lys Lys Leu Lys Lys
1               5

<210> SEQ ID NO 185
<211> LENGTH: 6
<212> TYPE: PRT
<213> ORGANISM: homo sapiens

<400> SEQUENCE: 185

Arg Lys Lys Phe Lys Tyr
1               5

<210> SEQ ID NO 186
<211> LENGTH: 6
<212> TYPE: PRT
<213> ORGANISM: homo sapiens

<400> SEQUENCE: 186

Gly Lys Lys Gln Lys Thr
1               5

<210> SEQ ID NO 187
<211> LENGTH: 8
<212> TYPE: PRT
<213> ORGANISM: homo sapiens

<400> SEQUENCE: 187

Leu Arg Arg Arg Lys Gly Lys Arg
1               5
```

```
<210> SEQ ID NO 188
<211> LENGTH: 6
<212> TYPE: PRT
<213> ORGANISM: homo sapiens

<400> SEQUENCE: 188

Leu Arg Arg Trp Arg Arg
1               5

<210> SEQ ID NO 189
<211> LENGTH: 6
<212> TYPE: PRT
<213> ORGANISM: homo sapiens

<400> SEQUENCE: 189

Leu Arg Arg Arg Lys Gly
1               5

<210> SEQ ID NO 190
<211> LENGTH: 6
<212> TYPE: PRT
<213> ORGANISM: homo sapiens

<400> SEQUENCE: 190

Asp Lys Lys Ala Lys Tyr
1               5

<210> SEQ ID NO 191
<211> LENGTH: 6
<212> TYPE: PRT
<213> ORGANISM: homo sapiens

<400> SEQUENCE: 191

Gly Arg Arg Glu Lys Arg
1               5

<210> SEQ ID NO 192
<211> LENGTH: 6
<212> TYPE: PRT
<213> ORGANISM: homo sapiens

<400> SEQUENCE: 192

Ala Lys Arg Gln Arg Leu
1               5

<210> SEQ ID NO 193
<211> LENGTH: 6
<212> TYPE: PRT
<213> ORGANISM: homo sapiens

<400> SEQUENCE: 193

Glu Lys Arg Ala Arg Ile
1               5

<210> SEQ ID NO 194
<211> LENGTH: 6
<212> TYPE: PRT
<213> ORGANISM: homo sapiens

<400> SEQUENCE: 194

Arg Lys Lys Ala Lys Ile
1               5

<210> SEQ ID NO 195
<211> LENGTH: 6
```

```
<212> TYPE: PRT
<213> ORGANISM: homo sapiens

<400> SEQUENCE: 195

Val Arg Arg Ile Arg Asp
1               5

<210> SEQ ID NO 196
<211> LENGTH: 6
<212> TYPE: PRT
<213> ORGANISM: homo sapiens

<400> SEQUENCE: 196

Leu Arg Lys Arg Arg Lys
1               5

<210> SEQ ID NO 197
<211> LENGTH: 6
<212> TYPE: PRT
<213> ORGANISM: homo sapiens

<400> SEQUENCE: 197

Asp Arg Arg Glu Arg Glu
1               5

<210> SEQ ID NO 198
<211> LENGTH: 8
<212> TYPE: PRT
<213> ORGANISM: homo sapiens

<400> SEQUENCE: 198

Lys Lys Lys Lys Ser Ser Arg Leu
1               5

<210> SEQ ID NO 199
<211> LENGTH: 6
<212> TYPE: PRT
<213> ORGANISM: homo sapiens

<400> SEQUENCE: 199

Thr Lys Lys Lys Lys Ser
1               5

<210> SEQ ID NO 200
<211> LENGTH: 6
<212> TYPE: PRT
<213> ORGANISM: homo sapiens

<400> SEQUENCE: 200

Gln Lys Arg Val Lys Glu
1               5

<210> SEQ ID NO 201
<211> LENGTH: 6
<212> TYPE: PRT
<213> ORGANISM: homo sapiens

<400> SEQUENCE: 201

Gly Lys Arg Ser Arg Thr
1               5

<210> SEQ ID NO 202
<211> LENGTH: 6
<212> TYPE: PRT
<213> ORGANISM: homo sapiens
```

```
<400> SEQUENCE: 202

Pro Lys Arg Lys Lys Ala
1               5

<210> SEQ ID NO 203
<211> LENGTH: 6
<212> TYPE: PRT
<213> ORGANISM: homo sapiens

<400> SEQUENCE: 203

Gly Lys Arg Glu Lys Ser
1               5

<210> SEQ ID NO 204
<211> LENGTH: 6
<212> TYPE: PRT
<213> ORGANISM: homo sapiens

<400> SEQUENCE: 204

His Lys Lys His Lys Lys
1               5

<210> SEQ ID NO 205
<211> LENGTH: 6
<212> TYPE: PRT
<213> ORGANISM: homo sapiens

<400> SEQUENCE: 205

Lys Lys Lys Val Lys Asp
1               5

<210> SEQ ID NO 206
<211> LENGTH: 6
<212> TYPE: PRT
<213> ORGANISM: homo sapiens

<400> SEQUENCE: 206

Glu Arg Lys Glu Arg Glu
1               5

<210> SEQ ID NO 207
<211> LENGTH: 6
<212> TYPE: PRT
<213> ORGANISM: homo sapiens

<400> SEQUENCE: 207

Ser Arg Lys Asn Arg Thr
1               5

<210> SEQ ID NO 208
<211> LENGTH: 6
<212> TYPE: PRT
<213> ORGANISM: homo sapiens

<400> SEQUENCE: 208

Gly Arg Arg Lys Arg Asn
1               5

<210> SEQ ID NO 209
<211> LENGTH: 6
<212> TYPE: PRT
<213> ORGANISM: homo sapiens

<400> SEQUENCE: 209
```

Ala Arg Arg Gln Arg Arg
1               5

<210> SEQ ID NO 210
<211> LENGTH: 6
<212> TYPE: PRT
<213> ORGANISM: homo sapiens

<400> SEQUENCE: 210

Cys Lys Arg Leu Lys Ser
1               5

<210> SEQ ID NO 211
<211> LENGTH: 6
<212> TYPE: PRT
<213> ORGANISM: homo sapiens

<400> SEQUENCE: 211

His Lys Arg Leu Arg Gln
1               5

<210> SEQ ID NO 212
<211> LENGTH: 8
<212> TYPE: PRT
<213> ORGANISM: homo sapiens

<400> SEQUENCE: 212

Pro Arg Lys Arg Leu Thr Lys Gly
1               5

<210> SEQ ID NO 213
<211> LENGTH: 8
<212> TYPE: PRT
<213> ORGANISM: homo sapiens

<400> SEQUENCE: 213

Arg Lys Arg Arg Lys Glu Lys Ser
1               5

<210> SEQ ID NO 214
<211> LENGTH: 8
<212> TYPE: PRT
<213> ORGANISM: homo sapiens

<400> SEQUENCE: 214

Pro Lys Lys Lys Arg Leu Arg Leu
1               5

<210> SEQ ID NO 215
<211> LENGTH: 6
<212> TYPE: PRT
<213> ORGANISM: homo sapiens

<400> SEQUENCE: 215

His Lys Lys Glu Arg Lys
1               5

<210> SEQ ID NO 216
<211> LENGTH: 6
<212> TYPE: PRT
<213> ORGANISM: homo sapiens

<400> SEQUENCE: 216

Thr Lys Lys Thr Lys Lys

```
1               5

<210> SEQ ID NO 217
<211> LENGTH: 6
<212> TYPE: PRT
<213> ORGANISM: homo sapiens

<400> SEQUENCE: 217

Pro Lys Lys Lys Arg Leu
1               5

<210> SEQ ID NO 218
<211> LENGTH: 6
<212> TYPE: PRT
<213> ORGANISM: homo sapiens

<400> SEQUENCE: 218

Ser Arg Lys Pro Arg Met
1               5

<210> SEQ ID NO 219
<211> LENGTH: 6
<212> TYPE: PRT
<213> ORGANISM: homo sapiens

<400> SEQUENCE: 219

Ser Lys Arg Lys Lys Ala
1               5

<210> SEQ ID NO 220
<211> LENGTH: 6
<212> TYPE: PRT
<213> ORGANISM: homo sapiens

<400> SEQUENCE: 220

Ile Lys Lys Ala Arg Ala
1               5

<210> SEQ ID NO 221
<211> LENGTH: 8
<212> TYPE: PRT
<213> ORGANISM: homo sapiens

<400> SEQUENCE: 221

Arg Lys Lys Arg Ser Gln Arg Pro
1               5

<210> SEQ ID NO 222
<211> LENGTH: 6
<212> TYPE: PRT
<213> ORGANISM: homo sapiens

<400> SEQUENCE: 222

Phe Arg Lys Lys Arg Ser
1               5

<210> SEQ ID NO 223
<211> LENGTH: 8
<212> TYPE: PRT
<213> ORGANISM: homo sapiens

<400> SEQUENCE: 223

Leu Lys Arg Lys Leu Ile Arg Leu
1               5
```

```
<210> SEQ ID NO 224
<211> LENGTH: 8
<212> TYPE: PRT
<213> ORGANISM: homo sapiens

<400> SEQUENCE: 224

Arg Lys Lys Arg Arg Ala Arg Leu
1               5

<210> SEQ ID NO 225
<211> LENGTH: 6
<212> TYPE: PRT
<213> ORGANISM: homo sapiens

<400> SEQUENCE: 225

Ala Arg Arg Leu Arg Glu
1               5

<210> SEQ ID NO 226
<211> LENGTH: 6
<212> TYPE: PRT
<213> ORGANISM: homo sapiens

<400> SEQUENCE: 226

Glu Arg Lys Lys Arg Arg
1               5

<210> SEQ ID NO 227
<211> LENGTH: 6
<212> TYPE: PRT
<213> ORGANISM: homo sapiens

<400> SEQUENCE: 227

Cys Lys Lys Ser Arg Lys
1               5

<210> SEQ ID NO 228
<211> LENGTH: 6
<212> TYPE: PRT
<213> ORGANISM: homo sapiens

<400> SEQUENCE: 228

His Lys Arg Met Lys Val
1               5

<210> SEQ ID NO 229
<211> LENGTH: 6
<212> TYPE: PRT
<213> ORGANISM: homo sapiens

<400> SEQUENCE: 229

Leu Lys Arg Phe Lys Tyr
1               5

<210> SEQ ID NO 230
<211> LENGTH: 6
<212> TYPE: PRT
<213> ORGANISM: homo sapiens

<400> SEQUENCE: 230

His Arg Lys Pro Lys Leu
1               5

<210> SEQ ID NO 231
```

```
<211> LENGTH: 6
<212> TYPE: PRT
<213> ORGANISM: homo sapiens

<400> SEQUENCE: 231

Leu Lys Arg Ser Arg Pro
1               5

<210> SEQ ID NO 232
<211> LENGTH: 6
<212> TYPE: PRT
<213> ORGANISM: homo sapiens

<400> SEQUENCE: 232

Pro Arg Lys Ser Arg Arg
1               5

<210> SEQ ID NO 233
<211> LENGTH: 6
<212> TYPE: PRT
<213> ORGANISM: homo sapiens

<400> SEQUENCE: 233

Asp Arg Arg Thr Arg Leu
1               5

<210> SEQ ID NO 234
<211> LENGTH: 8
<212> TYPE: PRT
<213> ORGANISM: homo sapiens

<400> SEQUENCE: 234

Gly Arg Arg Lys Ser Glu Arg Gln
1               5

<210> SEQ ID NO 235
<211> LENGTH: 6
<212> TYPE: PRT
<213> ORGANISM: homo sapiens

<400> SEQUENCE: 235

Ser Arg Arg Phe Arg Cys
1               5

<210> SEQ ID NO 236
<211> LENGTH: 6
<212> TYPE: PRT
<213> ORGANISM: homo sapiens

<400> SEQUENCE: 236

Asn Lys Lys Arg Arg Gln
1               5

<210> SEQ ID NO 237
<211> LENGTH: 6
<212> TYPE: PRT
<213> ORGANISM: homo sapiens

<400> SEQUENCE: 237

Glu Lys Arg Pro Arg Asp
1               5

<210> SEQ ID NO 238
<211> LENGTH: 6
<212> TYPE: PRT
```

<213> ORGANISM: homo sapiens

<400> SEQUENCE: 238

Ala Arg Arg Leu Lys Lys
1               5

<210> SEQ ID NO 239
<211> LENGTH: 6
<212> TYPE: PRT
<213> ORGANISM: homo sapiens

<400> SEQUENCE: 239

Gln Lys Lys Ile Arg Ile
1               5

<210> SEQ ID NO 240
<211> LENGTH: 6
<212> TYPE: PRT
<213> ORGANISM: homo sapiens

<400> SEQUENCE: 240

Phe Arg Lys Ala Arg Ser
1               5

<210> SEQ ID NO 241
<211> LENGTH: 6
<212> TYPE: PRT
<213> ORGANISM: homo sapiens

<400> SEQUENCE: 241

Glu Arg Lys Ala Lys Leu
1               5

<210> SEQ ID NO 242
<211> LENGTH: 8
<212> TYPE: PRT
<213> ORGANISM: homo sapiens

<400> SEQUENCE: 242

Glu Lys Lys Lys Lys Lys Lys Lys
1               5

<210> SEQ ID NO 243
<211> LENGTH: 6
<212> TYPE: PRT
<213> ORGANISM: homo sapiens

<400> SEQUENCE: 243

Leu Arg Lys His Arg His
1               5

<210> SEQ ID NO 244
<211> LENGTH: 6
<212> TYPE: PRT
<213> ORGANISM: homo sapiens

<400> SEQUENCE: 244

Leu Lys Lys Phe Lys Thr
1               5

<210> SEQ ID NO 245
<211> LENGTH: 6
<212> TYPE: PRT
<213> ORGANISM: homo sapiens

```
<400> SEQUENCE: 245

Asp Lys Lys Lys Lys Glu
1               5

<210> SEQ ID NO 246
<211> LENGTH: 6
<212> TYPE: PRT
<213> ORGANISM: homo sapiens

<400> SEQUENCE: 246

Glu Lys Lys Lys Lys Lys
1               5

<210> SEQ ID NO 247
<211> LENGTH: 6
<212> TYPE: PRT
<213> ORGANISM: homo sapiens

<400> SEQUENCE: 247

Tyr Lys Arg Tyr Lys Val
1               5

<210> SEQ ID NO 248
<211> LENGTH: 6
<212> TYPE: PRT
<213> ORGANISM: homo sapiens

<400> SEQUENCE: 248

Glu Lys Lys Lys Arg Glu
1               5

<210> SEQ ID NO 249
<211> LENGTH: 6
<212> TYPE: PRT
<213> ORGANISM: homo sapiens

<400> SEQUENCE: 249

Leu Lys Arg Ile Arg Glu
1               5

<210> SEQ ID NO 250
<211> LENGTH: 6
<212> TYPE: PRT
<213> ORGANISM: homo sapiens

<400> SEQUENCE: 250

Leu Lys Lys Thr Lys Cys
1               5

<210> SEQ ID NO 251
<211> LENGTH: 8
<212> TYPE: PRT
<213> ORGANISM: homo sapiens

<400> SEQUENCE: 251

Arg Lys Arg Lys Ser Val Arg Gly
1               5

<210> SEQ ID NO 252
<211> LENGTH: 6
<212> TYPE: PRT
<213> ORGANISM: homo sapiens

<400> SEQUENCE: 252
```

```
Glu Arg Lys Arg Lys Ser
1               5

<210> SEQ ID NO 253
<211> LENGTH: 6
<212> TYPE: PRT
<213> ORGANISM: homo sapiens

<400> SEQUENCE: 253

Arg Arg Lys Ser Arg Phe
1               5

<210> SEQ ID NO 254
<211> LENGTH: 6
<212> TYPE: PRT
<213> ORGANISM: homo sapiens

<400> SEQUENCE: 254

Phe Lys Arg Pro Lys Ala
1               5

<210> SEQ ID NO 255
<211> LENGTH: 6
<212> TYPE: PRT
<213> ORGANISM: homo sapiens

<400> SEQUENCE: 255

Ala Arg Lys Val Lys Ser
1               5

<210> SEQ ID NO 256
<211> LENGTH: 6
<212> TYPE: PRT
<213> ORGANISM: homo sapiens

<400> SEQUENCE: 256

Phe Lys Lys Thr Arg Tyr
1               5

<210> SEQ ID NO 257
<211> LENGTH: 8
<212> TYPE: PRT
<213> ORGANISM: homo sapiens

<400> SEQUENCE: 257

Pro Lys Lys Lys Gly Ile Lys Ser
1               5

<210> SEQ ID NO 258
<211> LENGTH: 6
<212> TYPE: PRT
<213> ORGANISM: homo sapiens

<400> SEQUENCE: 258

Ile Arg Arg Pro Arg Arg
1               5

<210> SEQ ID NO 259
<211> LENGTH: 6
<212> TYPE: PRT
<213> ORGANISM: homo sapiens

<400> SEQUENCE: 259

Leu Arg Lys His Arg Arg
1               5
```

-continued

```
<210> SEQ ID NO 260
<211> LENGTH: 6
<212> TYPE: PRT
<213> ORGANISM: homo sapiens

<400> SEQUENCE: 260

Gly Lys Lys Glu Lys Ala
1               5

<210> SEQ ID NO 261
<211> LENGTH: 6
<212> TYPE: PRT
<213> ORGANISM: homo sapiens

<400> SEQUENCE: 261

Asp Arg Arg Leu Lys Lys
1               5

<210> SEQ ID NO 262
<211> LENGTH: 8
<212> TYPE: PRT
<213> ORGANISM: homo sapiens

<400> SEQUENCE: 262

Asp Lys Arg Lys Cys Glu Arg Leu
1               5

<210> SEQ ID NO 263
<211> LENGTH: 8
<212> TYPE: PRT
<213> ORGANISM: homo sapiens

<400> SEQUENCE: 263

Pro Arg Lys Lys Arg Leu Lys Ser
1               5

<210> SEQ ID NO 264
<211> LENGTH: 6
<212> TYPE: PRT
<213> ORGANISM: homo sapiens

<400> SEQUENCE: 264

Asn Lys Lys Gly Lys Ala
1               5

<210> SEQ ID NO 265
<211> LENGTH: 6
<212> TYPE: PRT
<213> ORGANISM: homo sapiens

<400> SEQUENCE: 265

Pro Arg Lys Lys Arg Leu
1               5

<210> SEQ ID NO 266
<211> LENGTH: 6
<212> TYPE: PRT
<213> ORGANISM: homo sapiens

<400> SEQUENCE: 266

Gln Arg Arg Asn Lys Arg
1               5
```

```
<210> SEQ ID NO 267
<211> LENGTH: 6
<212> TYPE: PRT
<213> ORGANISM: homo sapiens

<400> SEQUENCE: 267

Tyr Arg Lys Ile Lys Leu
1               5

<210> SEQ ID NO 268
<211> LENGTH: 6
<212> TYPE: PRT
<213> ORGANISM: homo sapiens

<400> SEQUENCE: 268

Val Arg Arg His Arg Asn
1               5

<210> SEQ ID NO 269
<211> LENGTH: 6
<212> TYPE: PRT
<213> ORGANISM: homo sapiens

<400> SEQUENCE: 269

Trp Lys Arg Leu Lys Asp
1               5

<210> SEQ ID NO 270
<211> LENGTH: 8
<212> TYPE: PRT
<213> ORGANISM: homo sapiens

<400> SEQUENCE: 270

Leu Arg Arg Arg Arg Gly Arg Glu
1               5

<210> SEQ ID NO 271
<211> LENGTH: 8
<212> TYPE: PRT
<213> ORGANISM: homo sapiens

<400> SEQUENCE: 271

Leu Lys Lys Arg Ser Gly Lys Lys
1               5

<210> SEQ ID NO 272
<211> LENGTH: 6
<212> TYPE: PRT
<213> ORGANISM: homo sapiens

<400> SEQUENCE: 272

Leu Arg Arg Arg Arg Gly
1               5

<210> SEQ ID NO 273
<211> LENGTH: 6
<212> TYPE: PRT
<213> ORGANISM: homo sapiens

<400> SEQUENCE: 273

Gly Lys Lys Asp Lys His
1               5

<210> SEQ ID NO 274
<211> LENGTH: 6
```

```
<212> TYPE: PRT
<213> ORGANISM: homo sapiens

<400> SEQUENCE: 274

Leu Lys Lys Lys Lys Lys
1               5

<210> SEQ ID NO 275
<211> LENGTH: 6
<212> TYPE: PRT
<213> ORGANISM: homo sapiens

<400> SEQUENCE: 275

Ala Arg Lys Arg Lys Arg
1               5

<210> SEQ ID NO 276
<211> LENGTH: 6
<212> TYPE: PRT
<213> ORGANISM: homo sapiens

<400> SEQUENCE: 276

Ser Lys Arg Asn Arg Arg
1               5

<210> SEQ ID NO 277
<211> LENGTH: 6
<212> TYPE: PRT
<213> ORGANISM: homo sapiens

<400> SEQUENCE: 277

Ile Arg Arg Asn Lys Gly
1               5

<210> SEQ ID NO 278
<211> LENGTH: 6
<212> TYPE: PRT
<213> ORGANISM: homo sapiens

<400> SEQUENCE: 278

Gly Lys Lys Glu Lys Glu
1               5

<210> SEQ ID NO 279
<211> LENGTH: 6
<212> TYPE: PRT
<213> ORGANISM: homo sapiens

<400> SEQUENCE: 279

Thr Arg Arg Ser Arg Ala
1               5

<210> SEQ ID NO 280
<211> LENGTH: 8
<212> TYPE: PRT
<213> ORGANISM: homo sapiens

<400> SEQUENCE: 280

Ile Arg Arg Arg Phe Glu Lys Arg
1               5

<210> SEQ ID NO 281
<211> LENGTH: 6
<212> TYPE: PRT
<213> ORGANISM: homo sapiens
```

```
<400> SEQUENCE: 281

Ala Arg Arg Ile Lys Thr
1               5

<210> SEQ ID NO 282
<211> LENGTH: 6
<212> TYPE: PRT
<213> ORGANISM: homo sapiens

<400> SEQUENCE: 282

Phe Lys Lys Val Arg Gly
1               5

<210> SEQ ID NO 283
<211> LENGTH: 8
<212> TYPE: PRT
<213> ORGANISM: homo sapiens

<400> SEQUENCE: 283

His Arg Lys Arg Ser Arg Arg Val
1               5

<210> SEQ ID NO 284
<211> LENGTH: 6
<212> TYPE: PRT
<213> ORGANISM: homo sapiens

<400> SEQUENCE: 284

Arg Lys Arg Ser Arg Arg
1               5

<210> SEQ ID NO 285
<211> LENGTH: 8
<212> TYPE: PRT
<213> ORGANISM: homo sapiens

<400> SEQUENCE: 285

Thr Lys Arg Lys Lys Arg Arg Glu
1               5

<210> SEQ ID NO 286
<211> LENGTH: 6
<212> TYPE: PRT
<213> ORGANISM: homo sapiens

<400> SEQUENCE: 286

Thr Lys Arg Lys Lys Arg
1               5

<210> SEQ ID NO 287
<211> LENGTH: 6
<212> TYPE: PRT
<213> ORGANISM: homo sapiens

<400> SEQUENCE: 287

Thr Arg Arg Lys Arg His
1               5

<210> SEQ ID NO 288
<211> LENGTH: 6
<212> TYPE: PRT
<213> ORGANISM: homo sapiens

<400> SEQUENCE: 288
```

```
Pro Lys Lys Gly Arg Val
1               5

<210> SEQ ID NO 289
<211> LENGTH: 6
<212> TYPE: PRT
<213> ORGANISM: homo sapiens

<400> SEQUENCE: 289

Arg Arg Arg His Arg Thr
1               5

<210> SEQ ID NO 290
<211> LENGTH: 6
<212> TYPE: PRT
<213> ORGANISM: homo sapiens

<400> SEQUENCE: 290

Asn Arg Arg Ala Lys Gln
1               5

<210> SEQ ID NO 291
<211> LENGTH: 8
<212> TYPE: PRT
<213> ORGANISM: homo sapiens

<400> SEQUENCE: 291

Tyr Arg Arg Arg Glu Ser Lys Arg
1               5

<210> SEQ ID NO 292
<211> LENGTH: 8
<212> TYPE: PRT
<213> ORGANISM: homo sapiens

<400> SEQUENCE: 292

Met Arg Lys Arg Arg Leu Arg Glu
1               5

<210> SEQ ID NO 293
<211> LENGTH: 6
<212> TYPE: PRT
<213> ORGANISM: homo sapiens

<400> SEQUENCE: 293

Ser Lys Arg Lys Lys Ser
1               5

<210> SEQ ID NO 294
<211> LENGTH: 6
<212> TYPE: PRT
<213> ORGANISM: homo sapiens

<400> SEQUENCE: 294

Met Arg Lys Arg Arg Leu
1               5

<210> SEQ ID NO 295
<211> LENGTH: 6
<212> TYPE: PRT
<213> ORGANISM: homo sapiens

<400> SEQUENCE: 295

Lys Lys Lys Gln Arg Arg
```

```
<210> SEQ ID NO 296
<211> LENGTH: 6
<212> TYPE: PRT
<213> ORGANISM: homo sapiens

<400> SEQUENCE: 296

Asn Arg Arg Ala Lys Trp
1               5

<210> SEQ ID NO 297
<211> LENGTH: 6
<212> TYPE: PRT
<213> ORGANISM: homo sapiens

<400> SEQUENCE: 297

Arg Lys Arg Glu Arg Ser
1               5

<210> SEQ ID NO 298
<211> LENGTH: 6
<212> TYPE: PRT
<213> ORGANISM: homo sapiens

<400> SEQUENCE: 298

Lys Arg Arg Gly Arg Ile
1               5

<210> SEQ ID NO 299
<211> LENGTH: 6
<212> TYPE: PRT
<213> ORGANISM: homo sapiens

<400> SEQUENCE: 299

Met Lys Lys Glu Lys Gly
1               5

<210> SEQ ID NO 300
<211> LENGTH: 6
<212> TYPE: PRT
<213> ORGANISM: homo sapiens

<400> SEQUENCE: 300

Gly Arg Arg Ala Arg Pro
1               5

<210> SEQ ID NO 301
<211> LENGTH: 6
<212> TYPE: PRT
<213> ORGANISM: homo sapiens

<400> SEQUENCE: 301

Leu Lys Lys Gln Arg Ser
1               5

<210> SEQ ID NO 302
<211> LENGTH: 8
<212> TYPE: PRT
<213> ORGANISM: homo sapiens

<400> SEQUENCE: 302

Gly Lys Lys Lys Ser Thr Lys Thr
1               5
```

```
<210> SEQ ID NO 303
<211> LENGTH: 8
<212> TYPE: PRT
<213> ORGANISM: homo sapiens

<400> SEQUENCE: 303

Ala Lys Lys Arg Gly Ser Lys Gly
1               5

<210> SEQ ID NO 304
<211> LENGTH: 6
<212> TYPE: PRT
<213> ORGANISM: homo sapiens

<400> SEQUENCE: 304

Asn Lys Lys Gly Arg Val
1               5

<210> SEQ ID NO 305
<211> LENGTH: 6
<212> TYPE: PRT
<213> ORGANISM: homo sapiens

<400> SEQUENCE: 305

Ala Lys Lys Ala Lys Ser
1               5

<210> SEQ ID NO 306
<211> LENGTH: 6
<212> TYPE: PRT
<213> ORGANISM: homo sapiens

<400> SEQUENCE: 306

Ala Arg Lys Ser Lys Lys
1               5

<210> SEQ ID NO 307
<211> LENGTH: 6
<212> TYPE: PRT
<213> ORGANISM: homo sapiens

<400> SEQUENCE: 307

Asp Lys Lys Leu Lys Ser
1               5

<210> SEQ ID NO 308
<211> LENGTH: 8
<212> TYPE: PRT
<213> ORGANISM: homo sapiens

<400> SEQUENCE: 308

Lys Arg Arg Arg Asn Gln Lys Leu
1               5

<210> SEQ ID NO 309
<211> LENGTH: 6
<212> TYPE: PRT
<213> ORGANISM: homo sapiens

<400> SEQUENCE: 309

Glu Lys Arg Arg Arg Asn
1               5

<210> SEQ ID NO 310
```

```
<211> LENGTH: 6
<212> TYPE: PRT
<213> ORGANISM: homo sapiens

<400> SEQUENCE: 310

Pro Lys Lys Ala Arg Ala
1               5

<210> SEQ ID NO 311
<211> LENGTH: 6
<212> TYPE: PRT
<213> ORGANISM: homo sapiens

<400> SEQUENCE: 311

Ala Arg Arg Ala Lys Val
1               5

<210> SEQ ID NO 312
<211> LENGTH: 6
<212> TYPE: PRT
<213> ORGANISM: homo sapiens

<400> SEQUENCE: 312

Leu Lys Lys Phe Lys Asp
1               5

<210> SEQ ID NO 313
<211> LENGTH: 6
<212> TYPE: PRT
<213> ORGANISM: homo sapiens

<400> SEQUENCE: 313

Ser Lys Arg Pro Arg Leu
1               5

<210> SEQ ID NO 314
<211> LENGTH: 6
<212> TYPE: PRT
<213> ORGANISM: homo sapiens

<400> SEQUENCE: 314

Ala Arg Lys Gln Arg Glu
1               5

<210> SEQ ID NO 315
<211> LENGTH: 6
<212> TYPE: PRT
<213> ORGANISM: homo sapiens

<400> SEQUENCE: 315

Arg Arg Lys Ala Lys Glu
1               5

<210> SEQ ID NO 316
<211> LENGTH: 6
<212> TYPE: PRT
<213> ORGANISM: homo sapiens

<400> SEQUENCE: 316

Ile Arg Lys Gln Arg Glu
1               5

<210> SEQ ID NO 317
<211> LENGTH: 6
<212> TYPE: PRT
```

```
<213> ORGANISM: homo sapiens

<400> SEQUENCE: 317

Gln Arg Arg Val Lys Phe
1               5

<210> SEQ ID NO 318
<211> LENGTH: 6
<212> TYPE: PRT
<213> ORGANISM: homo sapiens

<400> SEQUENCE: 318

Lys Arg Arg Gly Arg Asn
1               5

<210> SEQ ID NO 319
<211> LENGTH: 6
<212> TYPE: PRT
<213> ORGANISM: homo sapiens

<400> SEQUENCE: 319

Arg Arg Lys Gly Arg Ile
1               5

<210> SEQ ID NO 320
<211> LENGTH: 6
<212> TYPE: PRT
<213> ORGANISM: homo sapiens

<400> SEQUENCE: 320

Ser Arg Lys Pro Arg Glu
1               5

<210> SEQ ID NO 321
<211> LENGTH: 6
<212> TYPE: PRT
<213> ORGANISM: homo sapiens

<400> SEQUENCE: 321

Ser Arg Lys Ser Lys Ser
1               5

<210> SEQ ID NO 322
<211> LENGTH: 6
<212> TYPE: PRT
<213> ORGANISM: homo sapiens

<400> SEQUENCE: 322

Lys Arg Arg Val Lys Ser
1               5

<210> SEQ ID NO 323
<211> LENGTH: 6
<212> TYPE: PRT
<213> ORGANISM: homo sapiens

<400> SEQUENCE: 323

Thr Lys Lys Ile Lys Leu
1               5

<210> SEQ ID NO 324
<211> LENGTH: 8
<212> TYPE: PRT
<213> ORGANISM: homo sapiens
```

```
<400> SEQUENCE: 324

Phe Arg Lys Arg Met Glu Lys Glu
1               5

<210> SEQ ID NO 325
<211> LENGTH: 6
<212> TYPE: PRT
<213> ORGANISM: homo sapiens

<400> SEQUENCE: 325

Arg Arg Lys Ala Arg Glu
1               5

<210> SEQ ID NO 326
<211> LENGTH: 6
<212> TYPE: PRT
<213> ORGANISM: homo sapiens

<400> SEQUENCE: 326

Lys Arg Lys Leu Lys Glu
1               5

<210> SEQ ID NO 327
<211> LENGTH: 6
<212> TYPE: PRT
<213> ORGANISM: homo sapiens

<400> SEQUENCE: 327

Lys Lys Arg Leu Arg Gln
1               5

<210> SEQ ID NO 328
<211> LENGTH: 6
<212> TYPE: PRT
<213> ORGANISM: homo sapiens

<400> SEQUENCE: 328

Ser Lys Lys Tyr Arg Gln
1               5

<210> SEQ ID NO 329
<211> LENGTH: 6
<212> TYPE: PRT
<213> ORGANISM: homo sapiens

<400> SEQUENCE: 329

Val Arg Lys Phe Arg Thr
1               5

<210> SEQ ID NO 330
<211> LENGTH: 6
<212> TYPE: PRT
<213> ORGANISM: homo sapiens

<400> SEQUENCE: 330

Gly Lys Lys Leu Lys Lys
1               5

<210> SEQ ID NO 331
<211> LENGTH: 6
<212> TYPE: PRT
<213> ORGANISM: homo sapiens

<400> SEQUENCE: 331
```

```
Glu Lys Arg Ala Lys Tyr
1               5

<210> SEQ ID NO 332
<211> LENGTH: 6
<212> TYPE: PRT
<213> ORGANISM: homo sapiens

<400> SEQUENCE: 332

Ser Lys Lys Tyr Lys Glu
1               5

<210> SEQ ID NO 333
<211> LENGTH: 6
<212> TYPE: PRT
<213> ORGANISM: homo sapiens

<400> SEQUENCE: 333

Lys Lys Lys Met Lys Tyr
1               5

<210> SEQ ID NO 334
<211> LENGTH: 6
<212> TYPE: PRT
<213> ORGANISM: homo sapiens

<400> SEQUENCE: 334

Lys Lys Arg Leu Lys Trp
1               5

<210> SEQ ID NO 335
<211> LENGTH: 6
<212> TYPE: PRT
<213> ORGANISM: homo sapiens

<400> SEQUENCE: 335

Lys Lys Lys Ala Lys Tyr
1               5

<210> SEQ ID NO 336
<211> LENGTH: 6
<212> TYPE: PRT
<213> ORGANISM: homo sapiens

<400> SEQUENCE: 336

Glu Lys Lys Glu Lys Leu
1               5

<210> SEQ ID NO 337
<211> LENGTH: 6
<212> TYPE: PRT
<213> ORGANISM: homo sapiens

<400> SEQUENCE: 337

Ser Lys Lys Met Lys Phe
1               5

<210> SEQ ID NO 338
<211> LENGTH: 8
<212> TYPE: PRT
<213> ORGANISM: homo sapiens

<400> SEQUENCE: 338

Phe Arg Arg Arg Gly Ala Arg Ala
1               5
```

<210> SEQ ID NO 339
<211> LENGTH: 8
<212> TYPE: PRT
<213> ORGANISM: homo sapiens

<400> SEQUENCE: 339

Gln Lys Arg Arg Tyr Ser Lys Gly
1               5

<210> SEQ ID NO 340
<211> LENGTH: 8
<212> TYPE: PRT
<213> ORGANISM: homo sapiens

<400> SEQUENCE: 340

Tyr Arg Lys Lys Pro His Arg Pro
1               5

<210> SEQ ID NO 341
<211> LENGTH: 6
<212> TYPE: PRT
<213> ORGANISM: homo sapiens

<400> SEQUENCE: 341

Asp Arg Lys Val Lys Ser
1               5

<210> SEQ ID NO 342
<211> LENGTH: 6
<212> TYPE: PRT
<213> ORGANISM: homo sapiens

<400> SEQUENCE: 342

Ile Lys Arg Lys Arg Glu
1               5

<210> SEQ ID NO 343
<211> LENGTH: 6
<212> TYPE: PRT
<213> ORGANISM: homo sapiens

<400> SEQUENCE: 343

Ser Lys Lys Gly Arg Lys
1               5

<210> SEQ ID NO 344
<211> LENGTH: 6
<212> TYPE: PRT
<213> ORGANISM: homo sapiens

<400> SEQUENCE: 344

His Arg Arg Pro Arg Gly
1               5

<210> SEQ ID NO 345
<211> LENGTH: 6
<212> TYPE: PRT
<213> ORGANISM: homo sapiens

<400> SEQUENCE: 345

Ala Arg Arg Pro Arg His
1               5

```
<210> SEQ ID NO 346
<211> LENGTH: 6
<212> TYPE: PRT
<213> ORGANISM: homo sapiens

<400> SEQUENCE: 346

Glu Lys Arg Ile Lys Glu
1               5

<210> SEQ ID NO 347
<211> LENGTH: 6
<212> TYPE: PRT
<213> ORGANISM: homo sapiens

<400> SEQUENCE: 347

Leu Lys Lys Ile Lys Gln
1               5

<210> SEQ ID NO 348
<211> LENGTH: 6
<212> TYPE: PRT
<213> ORGANISM: homo sapiens

<400> SEQUENCE: 348

Arg Arg Lys Pro Lys Pro
1               5

<210> SEQ ID NO 349
<211> LENGTH: 6
<212> TYPE: PRT
<213> ORGANISM: homo sapiens

<400> SEQUENCE: 349

Ala Arg Arg Lys Lys Ile
1               5

<210> SEQ ID NO 350
<211> LENGTH: 6
<212> TYPE: PRT
<213> ORGANISM: homo sapiens

<400> SEQUENCE: 350

Ala Arg Arg Lys Arg Gln
1               5

<210> SEQ ID NO 351
<211> LENGTH: 6
<212> TYPE: PRT
<213> ORGANISM: homo sapiens

<400> SEQUENCE: 351

Gln Lys Arg Leu Lys Lys
1               5

<210> SEQ ID NO 352
<211> LENGTH: 6
<212> TYPE: PRT
<213> ORGANISM: homo sapiens

<400> SEQUENCE: 352

Glu Lys Lys Thr Lys Arg
1               5

<210> SEQ ID NO 353
<211> LENGTH: 8
```

```
<212> TYPE: PRT
<213> ORGANISM: homo sapiens

<400> SEQUENCE: 353

Glu Lys Arg Lys Ser Glu Lys Ala
1               5

<210> SEQ ID NO 354
<211> LENGTH: 6
<212> TYPE: PRT
<213> ORGANISM: homo sapiens

<400> SEQUENCE: 354

Thr Arg Lys Lys Arg Lys
1               5

<210> SEQ ID NO 355
<211> LENGTH: 6
<212> TYPE: PRT
<213> ORGANISM: homo sapiens

<400> SEQUENCE: 355

Ala Arg Lys Leu Lys Lys
1               5

<210> SEQ ID NO 356
<211> LENGTH: 8
<212> TYPE: PRT
<213> ORGANISM: homo sapiens

<400> SEQUENCE: 356

Arg Lys Arg Arg Pro Ser Arg Pro
1               5

<210> SEQ ID NO 357
<211> LENGTH: 6
<212> TYPE: PRT
<213> ORGANISM: homo sapiens

<400> SEQUENCE: 357

Asn Lys Lys Lys Lys Glu
1               5

<210> SEQ ID NO 358
<211> LENGTH: 6
<212> TYPE: PRT
<213> ORGANISM: homo sapiens

<400> SEQUENCE: 358

Val Arg Lys Arg Arg Pro
1               5

<210> SEQ ID NO 359
<211> LENGTH: 8
<212> TYPE: PRT
<213> ORGANISM: homo sapiens

<400> SEQUENCE: 359

Trp Lys Lys Lys Tyr Glu Lys Glu
1               5

<210> SEQ ID NO 360
<211> LENGTH: 6
<212> TYPE: PRT
<213> ORGANISM: homo sapiens
```

-continued

```
<400> SEQUENCE: 360

Val Lys Arg Cys Lys Gln
1               5

<210> SEQ ID NO 361
<211> LENGTH: 6
<212> TYPE: PRT
<213> ORGANISM: homo sapiens

<400> SEQUENCE: 361

Glu Lys Arg Leu Arg Ala
1               5

<210> SEQ ID NO 362
<211> LENGTH: 6
<212> TYPE: PRT
<213> ORGANISM: homo sapiens

<400> SEQUENCE: 362

Val Lys Lys Ile Lys Glu
1               5

<210> SEQ ID NO 363
<211> LENGTH: 6
<212> TYPE: PRT
<213> ORGANISM: homo sapiens

<400> SEQUENCE: 363

Asn Lys Lys Phe Lys Met
1               5

<210> SEQ ID NO 364
<211> LENGTH: 6
<212> TYPE: PRT
<213> ORGANISM: homo sapiens

<400> SEQUENCE: 364

Glu Arg Arg His Arg Leu
1               5

<210> SEQ ID NO 365
<211> LENGTH: 6
<212> TYPE: PRT
<213> ORGANISM: homo sapiens

<400> SEQUENCE: 365

Ser Arg Arg Pro Arg Phe
1               5

<210> SEQ ID NO 366
<211> LENGTH: 8
<212> TYPE: PRT
<213> ORGANISM: homo sapiens

<400> SEQUENCE: 366

Thr Lys Arg Lys Lys Pro Arg Arg
1               5

<210> SEQ ID NO 367
<211> LENGTH: 6
<212> TYPE: PRT
<213> ORGANISM: homo sapiens

<400> SEQUENCE: 367
```

```
Pro Lys Lys Asp Lys Leu
1               5
```

<210> SEQ ID NO 368
<211> LENGTH: 6
<212> TYPE: PRT
<213> ORGANISM: homo sapiens

<400> SEQUENCE: 368

```
Thr Lys Arg Lys Lys Pro
1               5
```

<210> SEQ ID NO 369
<211> LENGTH: 6
<212> TYPE: PRT
<213> ORGANISM: homo sapiens

<400> SEQUENCE: 369

```
Asn Lys Lys Asn Arg Glu
1               5
```

<210> SEQ ID NO 370
<211> LENGTH: 6
<212> TYPE: PRT
<213> ORGANISM: homo sapiens

<400> SEQUENCE: 370

```
Leu Lys Lys Ser Arg Ile
1               5
```

<210> SEQ ID NO 371
<211> LENGTH: 6
<212> TYPE: PRT
<213> ORGANISM: homo sapiens

<400> SEQUENCE: 371

```
Pro Lys Lys Pro Arg Glu
1               5
```

<210> SEQ ID NO 372
<211> LENGTH: 6
<212> TYPE: PRT
<213> ORGANISM: homo sapiens

<400> SEQUENCE: 372

```
Ser Arg Lys Gln Arg Gln
1               5
```

<210> SEQ ID NO 373
<211> LENGTH: 6
<212> TYPE: PRT
<213> ORGANISM: homo sapiens

<400> SEQUENCE: 373

```
Val Lys Arg Lys Arg Lys
1               5
```

<210> SEQ ID NO 374
<211> LENGTH: 6
<212> TYPE: PRT
<213> ORGANISM: homo sapiens

<400> SEQUENCE: 374

```
Ala Arg Arg Leu Arg Arg
```

-continued

```
1               5

<210> SEQ ID NO 375
<211> LENGTH: 6
<212> TYPE: PRT
<213> ORGANISM: homo sapiens

<400> SEQUENCE: 375

Pro Arg Arg Cys Lys Trp
1               5

<210> SEQ ID NO 376
<211> LENGTH: 6
<212> TYPE: PRT
<213> ORGANISM: homo sapiens

<400> SEQUENCE: 376

Met Lys Lys Pro Arg Phe
1               5

<210> SEQ ID NO 377
<211> LENGTH: 6
<212> TYPE: PRT
<213> ORGANISM: homo sapiens

<400> SEQUENCE: 377

Arg Arg Arg Gln Arg Ala
1               5

<210> SEQ ID NO 378
<211> LENGTH: 6
<212> TYPE: PRT
<213> ORGANISM: homo sapiens

<400> SEQUENCE: 378

Pro Arg Arg Ile Arg Lys
1               5

<210> SEQ ID NO 379
<211> LENGTH: 6
<212> TYPE: PRT
<213> ORGANISM: homo sapiens

<400> SEQUENCE: 379

Ala Arg Arg Thr Arg Thr
1               5

<210> SEQ ID NO 380
<211> LENGTH: 6
<212> TYPE: PRT
<213> ORGANISM: homo sapiens

<400> SEQUENCE: 380

Gln Lys Arg Gly Arg Val
1               5

<210> SEQ ID NO 381
<211> LENGTH: 6
<212> TYPE: PRT
<213> ORGANISM: homo sapiens

<400> SEQUENCE: 381

Ser Arg Arg Ser Lys Leu
1               5
```

```
<210> SEQ ID NO 382
<211> LENGTH: 6
<212> TYPE: PRT
<213> ORGANISM: homo sapiens

<400> SEQUENCE: 382

Pro Lys Lys Ala Lys Ser
1               5

<210> SEQ ID NO 383
<211> LENGTH: 6
<212> TYPE: PRT
<213> ORGANISM: homo sapiens

<400> SEQUENCE: 383

Glu Lys Arg Asn Arg Lys
1               5

<210> SEQ ID NO 384
<211> LENGTH: 6
<212> TYPE: PRT
<213> ORGANISM: homo sapiens

<400> SEQUENCE: 384

Gly Arg Arg Tyr Arg Arg
1               5

<210> SEQ ID NO 385
<211> LENGTH: 6
<212> TYPE: PRT
<213> ORGANISM: homo sapiens

<400> SEQUENCE: 385

Pro Arg Lys Asn Lys Glu
1               5

<210> SEQ ID NO 386
<211> LENGTH: 8
<212> TYPE: PRT
<213> ORGANISM: homo sapiens

<400> SEQUENCE: 386

Lys Arg Arg Lys His Leu Lys Arg
1               5

<210> SEQ ID NO 387
<211> LENGTH: 6
<212> TYPE: PRT
<213> ORGANISM: homo sapiens

<400> SEQUENCE: 387

Trp Lys Arg Arg Lys His
1               5

<210> SEQ ID NO 388
<211> LENGTH: 6
<212> TYPE: PRT
<213> ORGANISM: homo sapiens

<400> SEQUENCE: 388

Leu Lys Arg Ser Arg Asp
1               5

<210> SEQ ID NO 389
```

```
<211> LENGTH: 6
<212> TYPE: PRT
<213> ORGANISM: homo sapiens

<400> SEQUENCE: 389

Gly Arg Lys Leu Arg Leu
1               5

<210> SEQ ID NO 390
<211> LENGTH: 6
<212> TYPE: PRT
<213> ORGANISM: homo sapiens

<400> SEQUENCE: 390

Ser Arg Lys Arg Lys Leu
1               5

<210> SEQ ID NO 391
<211> LENGTH: 8
<212> TYPE: PRT
<213> ORGANISM: homo sapiens

<400> SEQUENCE: 391

Met Arg Arg Arg Gln Arg Arg Glu
1               5

<210> SEQ ID NO 392
<211> LENGTH: 6
<212> TYPE: PRT
<213> ORGANISM: homo sapiens

<400> SEQUENCE: 392

Glu Lys Arg Thr Arg Leu
1               5

<210> SEQ ID NO 393
<211> LENGTH: 6
<212> TYPE: PRT
<213> ORGANISM: homo sapiens

<400> SEQUENCE: 393

Arg Arg Arg Gln Arg Arg
1               5

<210> SEQ ID NO 394
<211> LENGTH: 6
<212> TYPE: PRT
<213> ORGANISM: homo sapiens

<400> SEQUENCE: 394

Asn Arg Arg Cys Lys Leu
1               5

<210> SEQ ID NO 395
<211> LENGTH: 6
<212> TYPE: PRT
<213> ORGANISM: homo sapiens

<400> SEQUENCE: 395

Ala Lys Lys Tyr Arg Asp
1               5

<210> SEQ ID NO 396
<211> LENGTH: 8
<212> TYPE: PRT
```

<213> ORGANISM: homo sapiens

<400> SEQUENCE: 396

Lys Arg Lys Lys Pro Ser Arg Pro
1               5

<210> SEQ ID NO 397
<211> LENGTH: 6
<212> TYPE: PRT
<213> ORGANISM: homo sapiens

<400> SEQUENCE: 397

Ser Lys Lys Arg Lys Lys
1               5

<210> SEQ ID NO 398
<211> LENGTH: 6
<212> TYPE: PRT
<213> ORGANISM: homo sapiens

<400> SEQUENCE: 398

Gln Lys Arg Gln Lys Cys
1               5

<210> SEQ ID NO 399
<211> LENGTH: 6
<212> TYPE: PRT
<213> ORGANISM: homo sapiens

<400> SEQUENCE: 399

Tyr Arg Arg Arg Lys Arg
1               5

<210> SEQ ID NO 400
<211> LENGTH: 6
<212> TYPE: PRT
<213> ORGANISM: homo sapiens

<400> SEQUENCE: 400

Leu Lys Lys Asp Arg Glu
1               5

<210> SEQ ID NO 401
<211> LENGTH: 6
<212> TYPE: PRT
<213> ORGANISM: homo sapiens

<400> SEQUENCE: 401

Leu Lys Lys His Lys Glu
1               5

<210> SEQ ID NO 402
<211> LENGTH: 6
<212> TYPE: PRT
<213> ORGANISM: homo sapiens

<400> SEQUENCE: 402

Ser Arg Arg Thr Arg Trp
1               5

<210> SEQ ID NO 403
<211> LENGTH: 6
<212> TYPE: PRT
<213> ORGANISM: homo sapiens

```
<400> SEQUENCE: 403

Glu Arg Arg Arg Lys Phe
1               5

<210> SEQ ID NO 404
<211> LENGTH: 6
<212> TYPE: PRT
<213> ORGANISM: homo sapiens

<400> SEQUENCE: 404

Leu Arg Arg Cys Arg Ala
1               5

<210> SEQ ID NO 405
<211> LENGTH: 6
<212> TYPE: PRT
<213> ORGANISM: homo sapiens

<400> SEQUENCE: 405

Ser Arg Arg Ser Arg Ser
1               5

<210> SEQ ID NO 406
<211> LENGTH: 6
<212> TYPE: PRT
<213> ORGANISM: homo sapiens

<400> SEQUENCE: 406

Gly Arg Arg Arg Lys Ser
1               5

<210> SEQ ID NO 407
<211> LENGTH: 6
<212> TYPE: PRT
<213> ORGANISM: homo sapiens

<400> SEQUENCE: 407

Glu Arg Arg Ala Lys Gln
1               5

<210> SEQ ID NO 408
<211> LENGTH: 8
<212> TYPE: PRT
<213> ORGANISM: homo sapiens

<400> SEQUENCE: 408

Leu Arg Arg Arg Arg Val Lys Arg
1               5

<210> SEQ ID NO 409
<211> LENGTH: 6
<212> TYPE: PRT
<213> ORGANISM: homo sapiens

<400> SEQUENCE: 409

Leu Arg Arg Arg Arg Val
1               5

<210> SEQ ID NO 410
<211> LENGTH: 6
<212> TYPE: PRT
<213> ORGANISM: homo sapiens

<400> SEQUENCE: 410
```

```
Glu Lys Arg Gly Lys Gly
1               5

<210> SEQ ID NO 411
<211> LENGTH: 6
<212> TYPE: PRT
<213> ORGANISM: homo sapiens

<400> SEQUENCE: 411

Asn Arg Arg Leu Lys His
1               5

<210> SEQ ID NO 412
<211> LENGTH: 6
<212> TYPE: PRT
<213> ORGANISM: homo sapiens

<400> SEQUENCE: 412

Lys Arg Arg Tyr Arg Gly
1               5

<210> SEQ ID NO 413
<211> LENGTH: 6
<212> TYPE: PRT
<213> ORGANISM: homo sapiens

<400> SEQUENCE: 413

Ala Arg Arg Gln Arg Asp
1               5

<210> SEQ ID NO 414
<211> LENGTH: 6
<212> TYPE: PRT
<213> ORGANISM: homo sapiens

<400> SEQUENCE: 414

Pro Lys Lys Pro Lys Thr
1               5

<210> SEQ ID NO 415
<211> LENGTH: 6
<212> TYPE: PRT
<213> ORGANISM: homo sapiens

<400> SEQUENCE: 415

Asn Arg Arg Ser Arg Asn
1               5

<210> SEQ ID NO 416
<211> LENGTH: 6
<212> TYPE: PRT
<213> ORGANISM: homo sapiens

<400> SEQUENCE: 416

Glu Lys Arg Asp Lys Glu
1               5

<210> SEQ ID NO 417
<211> LENGTH: 6
<212> TYPE: PRT
<213> ORGANISM: homo sapiens

<400> SEQUENCE: 417

Gly Lys Lys Leu Lys Ala
1               5
```

```
<210> SEQ ID NO 418
<211> LENGTH: 6
<212> TYPE: PRT
<213> ORGANISM: homo sapiens

<400> SEQUENCE: 418

Lys Arg Lys Glu Lys Leu
1               5

<210> SEQ ID NO 419
<211> LENGTH: 6
<212> TYPE: PRT
<213> ORGANISM: homo sapiens

<400> SEQUENCE: 419

Ala Lys Lys His Lys Arg
1               5

<210> SEQ ID NO 420
<211> LENGTH: 6
<212> TYPE: PRT
<213> ORGANISM: homo sapiens

<400> SEQUENCE: 420

Lys Arg Lys Met Lys Ala
1               5

<210> SEQ ID NO 421
<211> LENGTH: 8
<212> TYPE: PRT
<213> ORGANISM: homo sapiens

<400> SEQUENCE: 421

Lys Lys Lys Arg Lys Gln Arg Arg
1               5

<210> SEQ ID NO 422
<211> LENGTH: 6
<212> TYPE: PRT
<213> ORGANISM: homo sapiens

<400> SEQUENCE: 422

Glu Lys Lys Lys Arg Lys
1               5

<210> SEQ ID NO 423
<211> LENGTH: 6
<212> TYPE: PRT
<213> ORGANISM: homo sapiens

<400> SEQUENCE: 423

Gln Arg Arg Asn Arg Thr
1               5

<210> SEQ ID NO 424
<211> LENGTH: 6
<212> TYPE: PRT
<213> ORGANISM: homo sapiens

<400> SEQUENCE: 424

Asn Arg Arg Ala Lys Phe
1               5
```

```
<210> SEQ ID NO 425
<211> LENGTH: 8
<212> TYPE: PRT
<213> ORGANISM: homo sapiens

<400> SEQUENCE: 425

Leu Lys Arg Lys Trp Ile Arg Cys
1               5

<210> SEQ ID NO 426
<211> LENGTH: 6
<212> TYPE: PRT
<213> ORGANISM: homo sapiens

<400> SEQUENCE: 426

Thr Arg Lys Ile Lys Leu
1               5

<210> SEQ ID NO 427
<211> LENGTH: 6
<212> TYPE: PRT
<213> ORGANISM: homo sapiens

<400> SEQUENCE: 427

Met Arg Lys Gln Arg Glu
1               5

<210> SEQ ID NO 428
<211> LENGTH: 6
<212> TYPE: PRT
<213> ORGANISM: homo sapiens

<400> SEQUENCE: 428

Pro Arg Arg Thr Arg Pro
1               5

<210> SEQ ID NO 429
<211> LENGTH: 6
<212> TYPE: PRT
<213> ORGANISM: homo sapiens

<400> SEQUENCE: 429

Gly Arg Arg Lys Arg Phe
1               5

<210> SEQ ID NO 430
<211> LENGTH: 6
<212> TYPE: PRT
<213> ORGANISM: homo sapiens

<400> SEQUENCE: 430

Gly Lys Lys Arg Lys Asn
1               5

<210> SEQ ID NO 431
<211> LENGTH: 6
<212> TYPE: PRT
<213> ORGANISM: homo sapiens

<400> SEQUENCE: 431

Gly Lys Lys Arg Lys Cys
1               5

<210> SEQ ID NO 432
<211> LENGTH: 8
```

```
<212> TYPE: PRT
<213> ORGANISM: homo sapiens

<400> SEQUENCE: 432

Ala Arg Arg Arg Cys Asp Arg Asp
1               5

<210> SEQ ID NO 433
<211> LENGTH: 6
<212> TYPE: PRT
<213> ORGANISM: homo sapiens

<400> SEQUENCE: 433

Glu Lys Lys Ser Lys Asp
1               5

<210> SEQ ID NO 434
<211> LENGTH: 6
<212> TYPE: PRT
<213> ORGANISM: homo sapiens

<400> SEQUENCE: 434

Pro Arg Lys Ala Arg Val
1               5

<210> SEQ ID NO 435
<211> LENGTH: 6
<212> TYPE: PRT
<213> ORGANISM: homo sapiens

<400> SEQUENCE: 435

Lys Lys Lys Tyr Lys Ala
1               5

<210> SEQ ID NO 436
<211> LENGTH: 6
<212> TYPE: PRT
<213> ORGANISM: homo sapiens

<400> SEQUENCE: 436

Arg Arg Arg Leu Lys Glu
1               5

<210> SEQ ID NO 437
<211> LENGTH: 6
<212> TYPE: PRT
<213> ORGANISM: homo sapiens

<400> SEQUENCE: 437

Lys Arg Arg Gln Arg Asp
1               5

<210> SEQ ID NO 438
<211> LENGTH: 6
<212> TYPE: PRT
<213> ORGANISM: homo sapiens

<400> SEQUENCE: 438

Thr Arg Arg Cys Arg Cys
1               5

<210> SEQ ID NO 439
<211> LENGTH: 6
<212> TYPE: PRT
<213> ORGANISM: homo sapiens
```

```
<400> SEQUENCE: 439

Ile Arg Arg Lys Arg Leu
1               5

<210> SEQ ID NO 440
<211> LENGTH: 8
<212> TYPE: PRT
<213> ORGANISM: homo sapiens

<400> SEQUENCE: 440

Gln Lys Arg Arg Thr Leu Lys Asn
1               5

<210> SEQ ID NO 441
<211> LENGTH: 6
<212> TYPE: PRT
<213> ORGANISM: homo sapiens

<400> SEQUENCE: 441

Met Arg Arg Leu Arg Ser
1               5

<210> SEQ ID NO 442
<211> LENGTH: 6
<212> TYPE: PRT
<213> ORGANISM: homo sapiens

<400> SEQUENCE: 442

Gln Lys Lys Val Lys Ile
1               5

<210> SEQ ID NO 443
<211> LENGTH: 6
<212> TYPE: PRT
<213> ORGANISM: homo sapiens

<400> SEQUENCE: 443

Asn Arg Arg Lys Arg Lys
1               5

<210> SEQ ID NO 444
<211> LENGTH: 6
<212> TYPE: PRT
<213> ORGANISM: homo sapiens

<400> SEQUENCE: 444

Leu Arg Arg Tyr Lys Arg
1               5

<210> SEQ ID NO 445
<211> LENGTH: 6
<212> TYPE: PRT
<213> ORGANISM: homo sapiens

<400> SEQUENCE: 445

Lys Lys Lys Glu Lys Glu
1               5

<210> SEQ ID NO 446
<211> LENGTH: 8
<212> TYPE: PRT
<213> ORGANISM: homo sapiens

<400> SEQUENCE: 446
```

```
Ala Lys Arg Lys Ala Asp Arg Glu
1               5

<210> SEQ ID NO 447
<211> LENGTH: 6
<212> TYPE: PRT
<213> ORGANISM: homo sapiens

<400> SEQUENCE: 447

Lys Lys Arg His Arg Glu
1               5

<210> SEQ ID NO 448
<211> LENGTH: 8
<212> TYPE: PRT
<213> ORGANISM: homo sapiens

<400> SEQUENCE: 448

Leu Arg Arg Arg Leu Glu Lys Arg
1               5

<210> SEQ ID NO 449
<211> LENGTH: 6
<212> TYPE: PRT
<213> ORGANISM: homo sapiens

<400> SEQUENCE: 449

Ser Arg Arg Val Lys Ala
1               5

<210> SEQ ID NO 450
<211> LENGTH: 8
<212> TYPE: PRT
<213> ORGANISM: homo sapiens

<400> SEQUENCE: 450

Arg Lys Arg Lys Leu Glu Arg Ile
1               5

<210> SEQ ID NO 451
<211> LENGTH: 6
<212> TYPE: PRT
<213> ORGANISM: homo sapiens

<400> SEQUENCE: 451

Arg Lys Arg Leu Arg Asn
1               5

<210> SEQ ID NO 452
<211> LENGTH: 6
<212> TYPE: PRT
<213> ORGANISM: homo sapiens

<400> SEQUENCE: 452

Cys Arg Lys Arg Lys Leu
1               5

<210> SEQ ID NO 453
<211> LENGTH: 6
<212> TYPE: PRT
<213> ORGANISM: homo sapiens

<400> SEQUENCE: 453

Val Arg Lys Ala Arg Gly
```

```
1               5

<210> SEQ ID NO 454
<211> LENGTH: 6
<212> TYPE: PRT
<213> ORGANISM: homo sapiens

<400> SEQUENCE: 454

Asp Arg Arg Phe Arg Ser
1               5

<210> SEQ ID NO 455
<211> LENGTH: 6
<212> TYPE: PRT
<213> ORGANISM: homo sapiens

<400> SEQUENCE: 455

Ser Arg Arg Gln Arg Ile
1               5

<210> SEQ ID NO 456
<211> LENGTH: 6
<212> TYPE: PRT
<213> ORGANISM: homo sapiens

<400> SEQUENCE: 456

Thr Lys Arg Arg Arg Lys
1               5

<210> SEQ ID NO 457
<211> LENGTH: 6
<212> TYPE: PRT
<213> ORGANISM: homo sapiens

<400> SEQUENCE: 457

Val Lys Lys Tyr Lys Ser
1               5

<210> SEQ ID NO 458
<211> LENGTH: 8
<212> TYPE: PRT
<213> ORGANISM: homo sapiens

<400> SEQUENCE: 458

Gln Arg Arg Arg Thr Leu Lys Asn
1               5

<210> SEQ ID NO 459
<211> LENGTH: 8
<212> TYPE: PRT
<213> ORGANISM: homo sapiens

<400> SEQUENCE: 459

Asn Lys Lys Lys Ile Leu Arg Glu
1               5

<210> SEQ ID NO 460
<211> LENGTH: 6
<212> TYPE: PRT
<213> ORGANISM: homo sapiens

<400> SEQUENCE: 460

Leu Lys Lys Leu Arg Ile
1               5
```

```
<210> SEQ ID NO 461
<211> LENGTH: 6
<212> TYPE: PRT
<213> ORGANISM: homo sapiens

<400> SEQUENCE: 461

Phe Lys Lys Gly Arg Leu
1               5

<210> SEQ ID NO 462
<211> LENGTH: 6
<212> TYPE: PRT
<213> ORGANISM: homo sapiens

<400> SEQUENCE: 462

Cys Arg Arg His Lys Ile
1               5

<210> SEQ ID NO 463
<211> LENGTH: 6
<212> TYPE: PRT
<213> ORGANISM: homo sapiens

<400> SEQUENCE: 463

Ala Lys Lys Ile Lys Met
1               5

<210> SEQ ID NO 464
<211> LENGTH: 8
<212> TYPE: PRT
<213> ORGANISM: homo sapiens

<400> SEQUENCE: 464

Val Arg Lys Arg Cys His Lys His
1               5

<210> SEQ ID NO 465
<211> LENGTH: 6
<212> TYPE: PRT
<213> ORGANISM: homo sapiens

<400> SEQUENCE: 465

Arg Lys Lys Phe Lys Cys
1               5

<210> SEQ ID NO 466
<211> LENGTH: 6
<212> TYPE: PRT
<213> ORGANISM: homo sapiens

<400> SEQUENCE: 466

Glu Lys Lys Ala Arg Ser
1               5

<210> SEQ ID NO 467
<211> LENGTH: 6
<212> TYPE: PRT
<213> ORGANISM: homo sapiens

<400> SEQUENCE: 467

Gly Arg Arg Arg Arg Thr
1               5

<210> SEQ ID NO 468
```

```
<211> LENGTH: 6
<212> TYPE: PRT
<213> ORGANISM: homo sapiens

<400> SEQUENCE: 468

Glu Arg Arg Gln Arg Phe
1               5

<210> SEQ ID NO 469
<211> LENGTH: 6
<212> TYPE: PRT
<213> ORGANISM: homo sapiens

<400> SEQUENCE: 469

Leu Arg Lys Phe Arg Thr
1               5

<210> SEQ ID NO 470
<211> LENGTH: 6
<212> TYPE: PRT
<213> ORGANISM: homo sapiens

<400> SEQUENCE: 470

Arg Arg Arg Cys Arg Asp
1               5

<210> SEQ ID NO 471
<211> LENGTH: 6
<212> TYPE: PRT
<213> ORGANISM: homo sapiens

<400> SEQUENCE: 471

Val Lys Arg Pro Arg Phe
1               5

<210> SEQ ID NO 472
<211> LENGTH: 6
<212> TYPE: PRT
<213> ORGANISM: homo sapiens

<400> SEQUENCE: 472

Val Arg Lys Arg Arg Val
1               5

<210> SEQ ID NO 473
<211> LENGTH: 6
<212> TYPE: PRT
<213> ORGANISM: homo sapiens

<400> SEQUENCE: 473

Glu Lys Lys Ser Lys Asn
1               5

<210> SEQ ID NO 474
<211> LENGTH: 8
<212> TYPE: PRT
<213> ORGANISM: homo sapiens

<400> SEQUENCE: 474

Ile Arg Lys Lys Val Arg Arg Leu
1               5

<210> SEQ ID NO 475
<211> LENGTH: 6
<212> TYPE: PRT
```

<213> ORGANISM: homo sapiens

<400> SEQUENCE: 475

Lys Arg Arg Ala Lys Ala
1               5

<210> SEQ ID NO 476
<211> LENGTH: 6
<212> TYPE: PRT
<213> ORGANISM: homo sapiens

<400> SEQUENCE: 476

Met Lys Lys Val Arg Arg
1               5

<210> SEQ ID NO 477
<211> LENGTH: 6
<212> TYPE: PRT
<213> ORGANISM: homo sapiens

<400> SEQUENCE: 477

Asp Lys Arg Lys Arg Ser
1               5

<210> SEQ ID NO 478
<211> LENGTH: 6
<212> TYPE: PRT
<213> ORGANISM: homo sapiens

<400> SEQUENCE: 478

Arg Lys Lys Val Arg Arg
1               5

<210> SEQ ID NO 479
<211> LENGTH: 6
<212> TYPE: PRT
<213> ORGANISM: homo sapiens

<400> SEQUENCE: 479

Thr Lys Lys Cys Arg Glu
1               5

<210> SEQ ID NO 480
<211> LENGTH: 8
<212> TYPE: PRT
<213> ORGANISM: homo sapiens

<400> SEQUENCE: 480

Lys Arg Lys Lys Ser Glu Arg Thr
1               5

<210> SEQ ID NO 481
<211> LENGTH: 6
<212> TYPE: PRT
<213> ORGANISM: homo sapiens

<400> SEQUENCE: 481

Thr Arg Lys Thr Arg Arg
1               5

<210> SEQ ID NO 482
<211> LENGTH: 6
<212> TYPE: PRT
<213> ORGANISM: homo sapiens

```
<400> SEQUENCE: 482

Ile Lys Arg Lys Lys Ser
1               5

<210> SEQ ID NO 483
<211> LENGTH: 8
<212> TYPE: PRT
<213> ORGANISM: homo sapiens

<400> SEQUENCE: 483

Arg Lys Arg Lys Ala Glu Lys Gln
1               5

<210> SEQ ID NO 484
<211> LENGTH: 8
<212> TYPE: PRT
<213> ORGANISM: homo sapiens

<400> SEQUENCE: 484

Lys Lys Arg Lys Gly Gly Arg Asn
1               5

<210> SEQ ID NO 485
<211> LENGTH: 6
<212> TYPE: PRT
<213> ORGANISM: homo sapiens

<400> SEQUENCE: 485

Ala Arg Arg Gly Arg Lys
1               5

<210> SEQ ID NO 486
<211> LENGTH: 6
<212> TYPE: PRT
<213> ORGANISM: homo sapiens

<400> SEQUENCE: 486

Pro Lys Arg Gly Arg Pro
1               5

<210> SEQ ID NO 487
<211> LENGTH: 6
<212> TYPE: PRT
<213> ORGANISM: homo sapiens

<400> SEQUENCE: 487

Glu Lys Lys Arg Lys Gly
1               5

<210> SEQ ID NO 488
<211> LENGTH: 6
<212> TYPE: PRT
<213> ORGANISM: homo sapiens

<400> SEQUENCE: 488

Asp Arg Lys Arg Lys Gln
1               5

<210> SEQ ID NO 489
<211> LENGTH: 6
<212> TYPE: PRT
<213> ORGANISM: homo sapiens

<400> SEQUENCE: 489
```

```
Leu Lys Lys Ile Arg Arg
1               5

<210> SEQ ID NO 490
<211> LENGTH: 9
<212> TYPE: PRT
<213> ORGANISM: homo sapiens

<400> SEQUENCE: 490

Val Lys Lys Val Glu Lys Lys Arg Glu
1               5

<210> SEQ ID NO 491
<211> LENGTH: 8
<212> TYPE: PRT
<213> ORGANISM: homo sapiens

<400> SEQUENCE: 491

Thr Lys Arg Arg Lys Arg Lys Asn
1               5

<210> SEQ ID NO 492
<211> LENGTH: 6
<212> TYPE: PRT
<213> ORGANISM: homo sapiens

<400> SEQUENCE: 492

Thr Lys Arg Arg Lys Arg
1               5

<210> SEQ ID NO 493
<211> LENGTH: 6
<212> TYPE: PRT
<213> ORGANISM: homo sapiens

<400> SEQUENCE: 493

Trp Lys Arg Ile Arg Phe
1               5

<210> SEQ ID NO 494
<211> LENGTH: 8
<212> TYPE: PRT
<213> ORGANISM: homo sapiens

<400> SEQUENCE: 494

Asp Lys Lys Lys Leu Arg Arg Leu
1               5

<210> SEQ ID NO 495
<211> LENGTH: 6
<212> TYPE: PRT
<213> ORGANISM: homo sapiens

<400> SEQUENCE: 495

Met Arg Lys Asp Lys Lys
1               5

<210> SEQ ID NO 496
<211> LENGTH: 6
<212> TYPE: PRT
<213> ORGANISM: homo sapiens

<400> SEQUENCE: 496

Asn Lys Arg Gln Lys Ile
1               5
```

<210> SEQ ID NO 497
<211> LENGTH: 6
<212> TYPE: PRT
<213> ORGANISM: homo sapiens

<400> SEQUENCE: 497

Lys Arg Lys His Arg Asn
1               5

<210> SEQ ID NO 498
<211> LENGTH: 6
<212> TYPE: PRT
<213> ORGANISM: homo sapiens

<400> SEQUENCE: 498

Glu Lys Arg Arg Lys Ala
1               5

<210> SEQ ID NO 499
<211> LENGTH: 8
<212> TYPE: PRT
<213> ORGANISM: homo sapiens

<400> SEQUENCE: 499

Glu Lys Lys Lys Val Ser Lys Ala
1               5

<210> SEQ ID NO 500
<211> LENGTH: 6
<212> TYPE: PRT
<213> ORGANISM: homo sapiens

<400> SEQUENCE: 500

Ile Lys Arg Lys Lys Phe
1               5

<210> SEQ ID NO 501
<211> LENGTH: 6
<212> TYPE: PRT
<213> ORGANISM: homo sapiens

<400> SEQUENCE: 501

Thr Lys Arg Val Lys Lys
1               5

<210> SEQ ID NO 502
<211> LENGTH: 6
<212> TYPE: PRT
<213> ORGANISM: homo sapiens

<400> SEQUENCE: 502

Asp Arg Arg Gln Lys Arg
1               5

<210> SEQ ID NO 503
<211> LENGTH: 6
<212> TYPE: PRT
<213> ORGANISM: homo sapiens

<400> SEQUENCE: 503

Gln Arg Lys Gly Arg Lys
1               5

-continued

```
<210> SEQ ID NO 504
<211> LENGTH: 6
<212> TYPE: PRT
<213> ORGANISM: homo sapiens

<400> SEQUENCE: 504

Ala Arg Arg Leu Arg Ala
1               5

<210> SEQ ID NO 505
<211> LENGTH: 6
<212> TYPE: PRT
<213> ORGANISM: homo sapiens

<400> SEQUENCE: 505

Leu Arg Arg Thr Arg Ile
1               5

<210> SEQ ID NO 506
<211> LENGTH: 6
<212> TYPE: PRT
<213> ORGANISM: homo sapiens

<400> SEQUENCE: 506

Ile Lys Lys Leu Lys Val
1               5

<210> SEQ ID NO 507
<211> LENGTH: 8
<212> TYPE: PRT
<213> ORGANISM: homo sapiens

<400> SEQUENCE: 507

Ala Arg Arg Arg Arg Lys Arg Arg
1               5

<210> SEQ ID NO 508
<211> LENGTH: 8
<212> TYPE: PRT
<213> ORGANISM: homo sapiens

<400> SEQUENCE: 508

Pro Arg Arg Arg Arg Arg Arg Thr
1               5

<210> SEQ ID NO 509
<211> LENGTH: 8
<212> TYPE: PRT
<213> ORGANISM: homo sapiens

<400> SEQUENCE: 509

Trp Lys Lys Lys Thr Ser Arg Pro
1               5

<210> SEQ ID NO 510
<211> LENGTH: 6
<212> TYPE: PRT
<213> ORGANISM: homo sapiens

<400> SEQUENCE: 510

Ala Arg Arg Arg Arg Lys
1               5

<210> SEQ ID NO 511
<211> LENGTH: 6
```

```
<212> TYPE: PRT
<213> ORGANISM: homo sapiens

<400> SEQUENCE: 511

Pro Arg Arg Arg Arg
1               5

<210> SEQ ID NO 512
<211> LENGTH: 6
<212> TYPE: PRT
<213> ORGANISM: homo sapiens

<400> SEQUENCE: 512

Pro Arg Arg Pro Arg Ile
1               5

<210> SEQ ID NO 513
<211> LENGTH: 6
<212> TYPE: PRT
<213> ORGANISM: homo sapiens

<400> SEQUENCE: 513

Thr Arg Arg Met Arg Trp
1               5

<210> SEQ ID NO 514
<211> LENGTH: 8
<212> TYPE: PRT
<213> ORGANISM: homo sapiens

<400> SEQUENCE: 514

Cys Lys Lys Lys Met Arg Arg Lys
1               5

<210> SEQ ID NO 515
<211> LENGTH: 6
<212> TYPE: PRT
<213> ORGANISM: homo sapiens

<400> SEQUENCE: 515

Lys Lys Lys Met Arg Arg
1               5

<210> SEQ ID NO 516
<211> LENGTH: 6
<212> TYPE: PRT
<213> ORGANISM: homo sapiens

<400> SEQUENCE: 516

His Arg Arg Ser Lys Gln
1               5

<210> SEQ ID NO 517
<211> LENGTH: 6
<212> TYPE: PRT
<213> ORGANISM: homo sapiens

<400> SEQUENCE: 517

Arg Lys Arg Gly Lys Asn
1               5

<210> SEQ ID NO 518
<211> LENGTH: 8
<212> TYPE: PRT
<213> ORGANISM: homo sapiens
```

```
<400> SEQUENCE: 518

Ile Lys Lys Arg Ser Leu Arg Ser
1               5

<210> SEQ ID NO 519
<211> LENGTH: 6
<212> TYPE: PRT
<213> ORGANISM: homo sapiens

<400> SEQUENCE: 519

Ser Lys Arg Pro Lys Asn
1               5

<210> SEQ ID NO 520
<211> LENGTH: 6
<212> TYPE: PRT
<213> ORGANISM: homo sapiens

<400> SEQUENCE: 520

Pro Arg Arg Ser Arg Arg
1               5

<210> SEQ ID NO 521
<211> LENGTH: 6
<212> TYPE: PRT
<213> ORGANISM: homo sapiens

<400> SEQUENCE: 521

Trp Arg Arg Thr Arg Gly
1               5

<210> SEQ ID NO 522
<211> LENGTH: 6
<212> TYPE: PRT
<213> ORGANISM: homo sapiens

<400> SEQUENCE: 522

Gly Lys Lys Leu Lys Leu
1               5

<210> SEQ ID NO 523
<211> LENGTH: 6
<212> TYPE: PRT
<213> ORGANISM: homo sapiens

<400> SEQUENCE: 523

Ile Arg Lys Gln Lys Leu
1               5

<210> SEQ ID NO 524
<211> LENGTH: 8
<212> TYPE: PRT
<213> ORGANISM: homo sapiens

<400> SEQUENCE: 524

Asn Arg Lys Lys His Arg Arg Lys
1               5

<210> SEQ ID NO 525
<211> LENGTH: 6
<212> TYPE: PRT
<213> ORGANISM: homo sapiens

<400> SEQUENCE: 525
```

-continued

```
Arg Lys Lys His Arg Arg
1               5

<210> SEQ ID NO 526
<211> LENGTH: 6
<212> TYPE: PRT
<213> ORGANISM: homo sapiens

<400> SEQUENCE: 526

Ala Arg Arg Lys Arg Arg
1               5

<210> SEQ ID NO 527
<211> LENGTH: 6
<212> TYPE: PRT
<213> ORGANISM: homo sapiens

<400> SEQUENCE: 527

Asn Lys Arg Ile Arg Tyr
1               5

<210> SEQ ID NO 528
<211> LENGTH: 6
<212> TYPE: PRT
<213> ORGANISM: homo sapiens

<400> SEQUENCE: 528

Asp Lys Lys Lys Arg Met
1               5

<210> SEQ ID NO 529
<211> LENGTH: 6
<212> TYPE: PRT
<213> ORGANISM: homo sapiens

<400> SEQUENCE: 529

Lys Arg Lys Glu Lys Ala
1               5

<210> SEQ ID NO 530
<211> LENGTH: 6
<212> TYPE: PRT
<213> ORGANISM: homo sapiens

<400> SEQUENCE: 530

Tyr Arg Lys Lys Lys Gln
1               5

<210> SEQ ID NO 531
<211> LENGTH: 6
<212> TYPE: PRT
<213> ORGANISM: homo sapiens

<400> SEQUENCE: 531

Ile Lys Arg Leu Lys Ile
1               5

<210> SEQ ID NO 532
<211> LENGTH: 8
<212> TYPE: PRT
<213> ORGANISM: homo sapiens

<400> SEQUENCE: 532

Arg Lys Arg Arg Gly Leu Arg Ser
```

```
1               5

<210> SEQ ID NO 533
<211> LENGTH: 8
<212> TYPE: PRT
<213> ORGANISM: homo sapiens

<400> SEQUENCE: 533

Ser Arg Lys Lys Thr Arg Arg Met
1               5

<210> SEQ ID NO 534
<211> LENGTH: 6
<212> TYPE: PRT
<213> ORGANISM: homo sapiens

<400> SEQUENCE: 534

Met Arg Arg Ser Arg Ala
1               5

<210> SEQ ID NO 535
<211> LENGTH: 6
<212> TYPE: PRT
<213> ORGANISM: homo sapiens

<400> SEQUENCE: 535

Glu Arg Lys Arg Arg Gly
1               5

<210> SEQ ID NO 536
<211> LENGTH: 6
<212> TYPE: PRT
<213> ORGANISM: homo sapiens

<400> SEQUENCE: 536

Arg Lys Lys Thr Arg Arg
1               5

<210> SEQ ID NO 537
<211> LENGTH: 8
<212> TYPE: PRT
<213> ORGANISM: homo sapiens

<400> SEQUENCE: 537

Asn Lys Lys Lys His Leu Lys Lys
1               5

<210> SEQ ID NO 538
<211> LENGTH: 8
<212> TYPE: PRT
<213> ORGANISM: homo sapiens

<400> SEQUENCE: 538

Glu Lys Lys Lys Leu Lys Arg His
1               5

<210> SEQ ID NO 539
<211> LENGTH: 6
<212> TYPE: PRT
<213> ORGANISM: homo sapiens

<400> SEQUENCE: 539

Trp Lys Lys Lys Arg Ala
1               5
```

```
<210> SEQ ID NO 540
<211> LENGTH: 6
<212> TYPE: PRT
<213> ORGANISM: homo sapiens

<400> SEQUENCE: 540

Arg Lys Lys Ala Lys Phe
1               5

<210> SEQ ID NO 541
<211> LENGTH: 6
<212> TYPE: PRT
<213> ORGANISM: homo sapiens

<400> SEQUENCE: 541

Lys Lys Lys Leu Lys Arg
1               5

<210> SEQ ID NO 542
<211> LENGTH: 6
<212> TYPE: PRT
<213> ORGANISM: homo sapiens

<400> SEQUENCE: 542

Leu Lys Lys Phe Arg Gln
1               5

<210> SEQ ID NO 543
<211> LENGTH: 6
<212> TYPE: PRT
<213> ORGANISM: homo sapiens

<400> SEQUENCE: 543

Leu Arg Lys Ile Arg Thr
1               5

<210> SEQ ID NO 544
<211> LENGTH: 8
<212> TYPE: PRT
<213> ORGANISM: homo sapiens

<400> SEQUENCE: 544

Gln Lys Arg Arg Arg His Arg Ala
1               5

<210> SEQ ID NO 545
<211> LENGTH: 6
<212> TYPE: PRT
<213> ORGANISM: homo sapiens

<400> SEQUENCE: 545

Gln Lys Arg Arg Arg His
1               5

<210> SEQ ID NO 546
<211> LENGTH: 8
<212> TYPE: PRT
<213> ORGANISM: homo sapiens

<400> SEQUENCE: 546

Gln Lys Arg Lys Thr Gly Arg Leu
1               5

<210> SEQ ID NO 547
```

```
<211> LENGTH: 8
<212> TYPE: PRT
<213> ORGANISM: homo sapiens

<400> SEQUENCE: 547

Lys Arg Lys Lys Leu Val Arg Asp
1               5

<210> SEQ ID NO 548
<211> LENGTH: 8
<212> TYPE: PRT
<213> ORGANISM: homo sapiens

<400> SEQUENCE: 548

Glu Lys Arg Arg Arg Glu Arg Glu
1               5

<210> SEQ ID NO 549
<211> LENGTH: 8
<212> TYPE: PRT
<213> ORGANISM: homo sapiens

<400> SEQUENCE: 549

Glu Lys Lys Lys Lys Asn Lys Thr
1               5

<210> SEQ ID NO 550
<211> LENGTH: 6
<212> TYPE: PRT
<213> ORGANISM: homo sapiens

<400> SEQUENCE: 550

Arg Lys Lys Asn Lys Gly
1               5

<210> SEQ ID NO 551
<211> LENGTH: 6
<212> TYPE: PRT
<213> ORGANISM: homo sapiens

<400> SEQUENCE: 551

Ser Lys Lys Ser Lys Glu
1               5

<210> SEQ ID NO 552
<211> LENGTH: 6
<212> TYPE: PRT
<213> ORGANISM: homo sapiens

<400> SEQUENCE: 552

Glu Lys Lys Val Arg Leu
1               5

<210> SEQ ID NO 553
<211> LENGTH: 6
<212> TYPE: PRT
<213> ORGANISM: homo sapiens

<400> SEQUENCE: 553

Leu Lys Arg Lys Lys Leu
1               5

<210> SEQ ID NO 554
<211> LENGTH: 6
<212> TYPE: PRT
```

<213> ORGANISM: homo sapiens

<400> SEQUENCE: 554

Glu Lys Arg Arg Arg Glu
1               5

<210> SEQ ID NO 555
<211> LENGTH: 6
<212> TYPE: PRT
<213> ORGANISM: homo sapiens

<400> SEQUENCE: 555

Glu Lys Lys Glu Lys Lys
1               5

<210> SEQ ID NO 556
<211> LENGTH: 9
<212> TYPE: PRT
<213> ORGANISM: homo sapiens

<400> SEQUENCE: 556

Gln Lys Lys Asp Val Val Lys Arg Gln
1               5

<210> SEQ ID NO 557
<211> LENGTH: 6
<212> TYPE: PRT
<213> ORGANISM: homo sapiens

<400> SEQUENCE: 557

Gly Lys Arg Tyr Lys Phe
1               5

<210> SEQ ID NO 558
<211> LENGTH: 6
<212> TYPE: PRT
<213> ORGANISM: homo sapiens

<400> SEQUENCE: 558

Arg Arg Arg Gly Lys Thr
1               5

<210> SEQ ID NO 559
<211> LENGTH: 6
<212> TYPE: PRT
<213> ORGANISM: homo sapiens

<400> SEQUENCE: 559

Val Arg Arg Tyr Arg Ala
1               5

<210> SEQ ID NO 560
<211> LENGTH: 6
<212> TYPE: PRT
<213> ORGANISM: homo sapiens

<400> SEQUENCE: 560

Met Arg Arg Arg Lys Pro
1               5

<210> SEQ ID NO 561
<211> LENGTH: 6
<212> TYPE: PRT
<213> ORGANISM: homo sapiens

```
<400> SEQUENCE: 561

Lys Lys Lys Val Lys Asn
1               5

<210> SEQ ID NO 562
<211> LENGTH: 6
<212> TYPE: PRT
<213> ORGANISM: homo sapiens

<400> SEQUENCE: 562

Leu Arg Lys Thr Arg His
1               5

<210> SEQ ID NO 563
<211> LENGTH: 6
<212> TYPE: PRT
<213> ORGANISM: homo sapiens

<400> SEQUENCE: 563

Gly Lys Arg Trp Lys Glu
1               5

<210> SEQ ID NO 564
<211> LENGTH: 6
<212> TYPE: PRT
<213> ORGANISM: homo sapiens

<400> SEQUENCE: 564

Leu Arg Lys Thr Lys Ala
1               5

<210> SEQ ID NO 565
<211> LENGTH: 8
<212> TYPE: PRT
<213> ORGANISM: homo sapiens

<400> SEQUENCE: 565

Ile Arg Arg Arg Ala Val Arg Ser
1               5

<210> SEQ ID NO 566
<211> LENGTH: 6
<212> TYPE: PRT
<213> ORGANISM: homo sapiens

<400> SEQUENCE: 566

Phe Lys Arg Lys Lys Phe
1               5

<210> SEQ ID NO 567
<211> LENGTH: 6
<212> TYPE: PRT
<213> ORGANISM: homo sapiens

<400> SEQUENCE: 567

Ile Arg Lys Pro Arg His
1               5

<210> SEQ ID NO 568
<211> LENGTH: 6
<212> TYPE: PRT
<213> ORGANISM: homo sapiens

<400> SEQUENCE: 568
```

```
Val Arg Lys Met Arg Asp
1               5

<210> SEQ ID NO 569
<211> LENGTH: 6
<212> TYPE: PRT
<213> ORGANISM: homo sapiens

<400> SEQUENCE: 569

Val Lys Lys Val Arg Leu
1               5

<210> SEQ ID NO 570
<211> LENGTH: 6
<212> TYPE: PRT
<213> ORGANISM: homo sapiens

<400> SEQUENCE: 570

Ala Arg Arg Leu Arg Asn
1               5

<210> SEQ ID NO 571
<211> LENGTH: 8
<212> TYPE: PRT
<213> ORGANISM: homo sapiens

<400> SEQUENCE: 571

Lys Lys Lys Lys Thr Gly Arg Ala
1               5

<210> SEQ ID NO 572
<211> LENGTH: 6
<212> TYPE: PRT
<213> ORGANISM: homo sapiens

<400> SEQUENCE: 572

Leu Arg Arg His Lys Arg
1               5

<210> SEQ ID NO 573
<211> LENGTH: 8
<212> TYPE: PRT
<213> ORGANISM: homo sapiens

<400> SEQUENCE: 573

Asn Arg Lys Arg Leu Tyr Lys Val
1               5

<210> SEQ ID NO 574
<211> LENGTH: 8
<212> TYPE: PRT
<213> ORGANISM: homo sapiens

<400> SEQUENCE: 574

Glu Arg Lys Arg Ser Arg Arg Arg
1               5

<210> SEQ ID NO 575
<211> LENGTH: 8
<212> TYPE: PRT
<213> ORGANISM: homo sapiens

<400> SEQUENCE: 575

Gln Arg Arg Arg Thr Pro Arg Pro
1               5
```

```
<210> SEQ ID NO 576
<211> LENGTH: 8
<212> TYPE: PRT
<213> ORGANISM: homo sapiens

<400> SEQUENCE: 576

Glu Lys Lys Lys Lys Arg Arg Glu
1               5

<210> SEQ ID NO 577
<211> LENGTH: 6
<212> TYPE: PRT
<213> ORGANISM: homo sapiens

<400> SEQUENCE: 577

Val Arg Lys Leu Arg Lys
1               5

<210> SEQ ID NO 578
<211> LENGTH: 6
<212> TYPE: PRT
<213> ORGANISM: homo sapiens

<400> SEQUENCE: 578

Gly Arg Arg Gln Lys Lys
1               5

<210> SEQ ID NO 579
<211> LENGTH: 6
<212> TYPE: PRT
<213> ORGANISM: homo sapiens

<400> SEQUENCE: 579

Thr Lys Lys Gln Lys Arg
1               5

<210> SEQ ID NO 580
<211> LENGTH: 6
<212> TYPE: PRT
<213> ORGANISM: homo sapiens

<400> SEQUENCE: 580

Glu Lys Lys Lys Lys Arg
1               5

<210> SEQ ID NO 581
<211> LENGTH: 6
<212> TYPE: PRT
<213> ORGANISM: homo sapiens

<400> SEQUENCE: 581

Trp Lys Arg Ile Lys Gly
1               5

<210> SEQ ID NO 582
<211> LENGTH: 8
<212> TYPE: PRT
<213> ORGANISM: homo sapiens

<400> SEQUENCE: 582

Asn Arg Arg Arg Gln Glu Arg Phe
1               5
```

```
<210> SEQ ID NO 583
<211> LENGTH: 6
<212> TYPE: PRT
<213> ORGANISM: homo sapiens

<400> SEQUENCE: 583

Arg Lys Arg Ala Lys Asp
1               5

<210> SEQ ID NO 584
<211> LENGTH: 8
<212> TYPE: PRT
<213> ORGANISM: homo sapiens

<400> SEQUENCE: 584

Leu Arg Lys Lys Leu His Lys Phe
1               5

<210> SEQ ID NO 585
<211> LENGTH: 6
<212> TYPE: PRT
<213> ORGANISM: homo sapiens

<400> SEQUENCE: 585

Ala Arg Lys Asn Lys Asn
1               5

<210> SEQ ID NO 586
<211> LENGTH: 6
<212> TYPE: PRT
<213> ORGANISM: homo sapiens

<400> SEQUENCE: 586

Ser Lys Lys Arg Lys Asn
1               5

<210> SEQ ID NO 587
<211> LENGTH: 6
<212> TYPE: PRT
<213> ORGANISM: homo sapiens

<400> SEQUENCE: 587

Ser Arg Arg Tyr Arg Gly
1               5

<210> SEQ ID NO 588
<211> LENGTH: 6
<212> TYPE: PRT
<213> ORGANISM: homo sapiens

<400> SEQUENCE: 588

His Arg Lys Asn Lys Pro
1               5

<210> SEQ ID NO 589
<211> LENGTH: 8
<212> TYPE: PRT
<213> ORGANISM: homo sapiens

<400> SEQUENCE: 589

Ser Arg Arg Arg Phe Arg Lys Ile
1               5

<210> SEQ ID NO 590
<211> LENGTH: 8
```

```
<212> TYPE: PRT
<213> ORGANISM: homo sapiens

<400> SEQUENCE: 590

Gln Arg Lys Lys Arg Trp Arg Ser
1               5

<210> SEQ ID NO 591
<211> LENGTH: 8
<212> TYPE: PRT
<213> ORGANISM: homo sapiens

<400> SEQUENCE: 591

His Lys Lys Arg Ala Arg Arg Ser
1               5

<210> SEQ ID NO 592
<211> LENGTH: 6
<212> TYPE: PRT
<213> ORGANISM: homo sapiens

<400> SEQUENCE: 592

Arg Arg Arg Phe Arg Lys
1               5

<210> SEQ ID NO 593
<211> LENGTH: 6
<212> TYPE: PRT
<213> ORGANISM: homo sapiens

<400> SEQUENCE: 593

Ser Lys Lys Val Lys Ala
1               5

<210> SEQ ID NO 594
<211> LENGTH: 6
<212> TYPE: PRT
<213> ORGANISM: homo sapiens

<400> SEQUENCE: 594

Leu Lys Arg Met Lys Ile
1               5

<210> SEQ ID NO 595
<211> LENGTH: 6
<212> TYPE: PRT
<213> ORGANISM: homo sapiens

<400> SEQUENCE: 595

Gln Arg Lys Lys Arg Trp
1               5

<210> SEQ ID NO 596
<211> LENGTH: 6
<212> TYPE: PRT
<213> ORGANISM: homo sapiens

<400> SEQUENCE: 596

Lys Lys Arg Ala Arg Arg
1               5

<210> SEQ ID NO 597
<211> LENGTH: 6
<212> TYPE: PRT
<213> ORGANISM: homo sapiens
```

```
<400> SEQUENCE: 597

Ala Arg Lys Val Lys Gln
1               5

<210> SEQ ID NO 598
<211> LENGTH: 8
<212> TYPE: PRT
<213> ORGANISM: homo sapiens

<400> SEQUENCE: 598

Glu Arg Lys Lys Ile Thr Arg Glu
1               5

<210> SEQ ID NO 599
<211> LENGTH: 6
<212> TYPE: PRT
<213> ORGANISM: homo sapiens

<400> SEQUENCE: 599

Gly Arg Lys Arg Lys Glu
1               5

<210> SEQ ID NO 600
<211> LENGTH: 6
<212> TYPE: PRT
<213> ORGANISM: homo sapiens

<400> SEQUENCE: 600

Leu Lys Arg Pro Arg Leu
1               5

<210> SEQ ID NO 601
<211> LENGTH: 6
<212> TYPE: PRT
<213> ORGANISM: homo sapiens

<400> SEQUENCE: 601

Val Lys Arg Glu Lys Pro
1               5

<210> SEQ ID NO 602
<211> LENGTH: 6
<212> TYPE: PRT
<213> ORGANISM: homo sapiens

<400> SEQUENCE: 602

Ser Lys Arg Pro Lys Thr
1               5

<210> SEQ ID NO 603
<211> LENGTH: 6
<212> TYPE: PRT
<213> ORGANISM: homo sapiens

<400> SEQUENCE: 603

Glu Lys Lys Asn Lys Leu
1               5

<210> SEQ ID NO 604
<211> LENGTH: 6
<212> TYPE: PRT
<213> ORGANISM: homo sapiens

<400> SEQUENCE: 604
```

Asn Lys Arg Pro Arg Thr
1               5

<210> SEQ ID NO 605
<211> LENGTH: 6
<212> TYPE: PRT
<213> ORGANISM: homo sapiens

<400> SEQUENCE: 605

Asp Lys Arg Leu Arg Thr
1               5

<210> SEQ ID NO 606
<211> LENGTH: 6
<212> TYPE: PRT
<213> ORGANISM: homo sapiens

<400> SEQUENCE: 606

Gln Lys Arg Phe Arg Thr
1               5

<210> SEQ ID NO 607
<211> LENGTH: 6
<212> TYPE: PRT
<213> ORGANISM: homo sapiens

<400> SEQUENCE: 607

Glu Lys Lys Ser Lys Leu
1               5

<210> SEQ ID NO 608
<211> LENGTH: 6
<212> TYPE: PRT
<213> ORGANISM: homo sapiens

<400> SEQUENCE: 608

Gln Arg Lys Asp Lys Asp
1               5

<210> SEQ ID NO 609
<211> LENGTH: 6
<212> TYPE: PRT
<213> ORGANISM: homo sapiens

<400> SEQUENCE: 609

Pro Lys Lys Glu Lys Gly
1               5

<210> SEQ ID NO 610
<211> LENGTH: 6
<212> TYPE: PRT
<213> ORGANISM: homo sapiens

<400> SEQUENCE: 610

Tyr Lys Arg Arg Lys Lys
1               5

<210> SEQ ID NO 611
<211> LENGTH: 6
<212> TYPE: PRT
<213> ORGANISM: homo sapiens

<400> SEQUENCE: 611

Thr Arg Arg Glu Arg Ala

```
<210> SEQ ID NO 612
<211> LENGTH: 6
<212> TYPE: PRT
<213> ORGANISM: homo sapiens

<400> SEQUENCE: 612

His Arg Lys Leu Lys Val
1               5

<210> SEQ ID NO 613
<211> LENGTH: 6
<212> TYPE: PRT
<213> ORGANISM: homo sapiens

<400> SEQUENCE: 613

Pro Lys Lys Pro Lys Gly
1               5

<210> SEQ ID NO 614
<211> LENGTH: 6
<212> TYPE: PRT
<213> ORGANISM: homo sapiens

<400> SEQUENCE: 614

Gly Lys Lys Lys Lys Asp
1               5
```